US006734001B1

(12) United States Patent
Alessi

(10) Patent No.: US 6,734,001 B1
(45) Date of Patent: May 11, 2004

(54) 3-PHOSPHOINOSITIDE-DEPENDENT PROTEIN KINASE

(75) Inventor: Dario Renato Alessi, Dundee (GB)

(73) Assignee: Medical Research Council (GB)

( * ) Notice: Subject to any disclaimer, the term of this patent is extended or adjusted under 35 U.S.C. 154(b) by 0 days.

(21) Appl. No.: 08/943,667

(22) Filed: Oct. 3, 1997

(30) Foreign Application Priority Data

Mar. 17, 1997 (GB) .............................................. 9705462
Jun. 19, 1997 (GB) .............................................. 9712826
Aug. 15, 1997 (GB) .............................................. 9717253

(51) Int. Cl.[7] .......................... C12N 9/12; C12Q 1/48; C07K 17/00; A61K 38/53
(52) U.S. Cl. ........................ 435/194; 435/15; 435/69.1; 530/350; 424/94.5
(58) Field of Search ........................ 435/194, 15, 69.1; 424/94.5; 530/350

(56) References Cited

FOREIGN PATENT DOCUMENTS

WO      WO 99/16887      4/1999

OTHER PUBLICATIONS

Stephens et al., Science, 279:710–714, 1998.*
Broun et al., Science 282:1315–1317, 1998.*
Bork, Genome Research, 10:398–4000, 2000.*
Van de Loo et al., Proc. Natl. Acad. Sci. 92:6743–6747, 1995.*
Stokoe et al., "Phosphatidylinositol (3,4,5) triphosphate plays a dual role in the activation of the PH domain–containing protein kinase, PKB", Abstract from Cell Sign Mech FEBS 97 Special Meeting, Amsterdam Jun. 29–Jul. 3, 1997.
Alessi et al., Curr Bio 7:261–269 (1997).
Dudek et al., Science 275:661–664 (1997).
Franke et al., Science 275:665–668 (1997).
Kauffmann–Zeh et al., Nature 385:554–548 (1997).
Jones et al., Proc Natl Acad Sci USA 88:4171–4175 (1991).
Cross et al., Nature 378:785–789 (1995).
Welsh et al., Biochem J 303:15–20 (1994).
Konishi et al., Biochem Biophys Res Commun 216:526–534 (1995).
Alessi et al., EMBO J 15:6541–6551 (1996).
James et al., Biochem J 315:709–713 (1996).
Klippel et al., Mol Cell Biol 17:338–344 (1997).
Andjelkovic et al., Proc Natl Acad Sci USA 93:5699–5704 (1996).
Frech et al., J Biol Chem 272:8474–8481 (1997).
Kohn et al., EMBO J 14:4288–4295 (1995).
Kohn et al., J Biol Chem 271:21920–21926 (1996).
Alessi et al., FEBS Letters 399:333–338 (1996).
Hemming, Science 275:628–630 (1997).
Stokoe et al., Science 277:567–570 (1997).
Kohn et al., J Biol Chem 271:31372–31378 (1996).
Cheng et al., Proc Natl Acad Sci USA 93:3636–3641 (1996).

* cited by examiner

*Primary Examiner*—Rebecca E. Prouty
*Assistant Examiner*—Delia Ramirez
(74) *Attorney, Agent, or Firm*—Rogalskyj & Weyand, LLP

(57) ABSTRACT

A substantially pure 3-phosphoinositide dependent protein kinase that phosphorylates and activates protein kinase Bα. A recombinant polynucleotide encoding a protein kinase as defined. Uses of the protein kinase and polynucleotide, especially in screening for new drugs.

14 Claims, 21 Drawing Sheets

Figure 1:
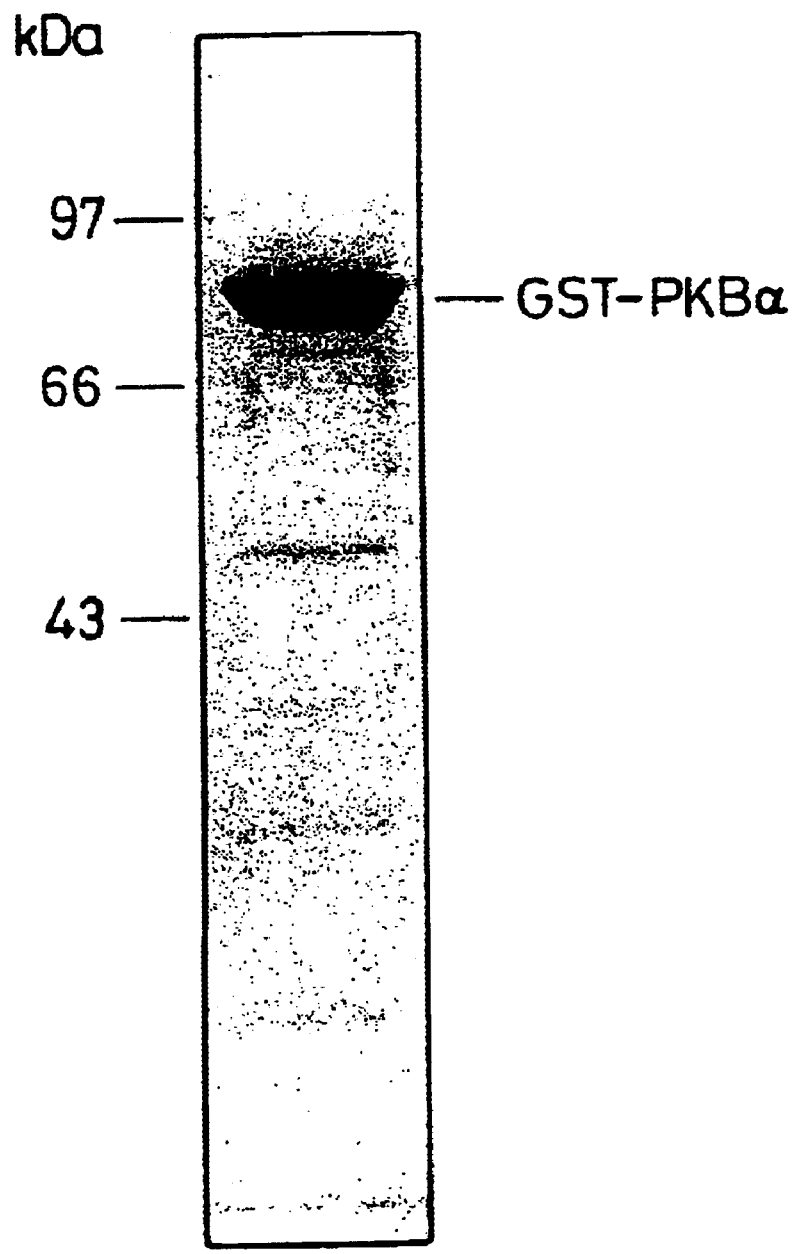

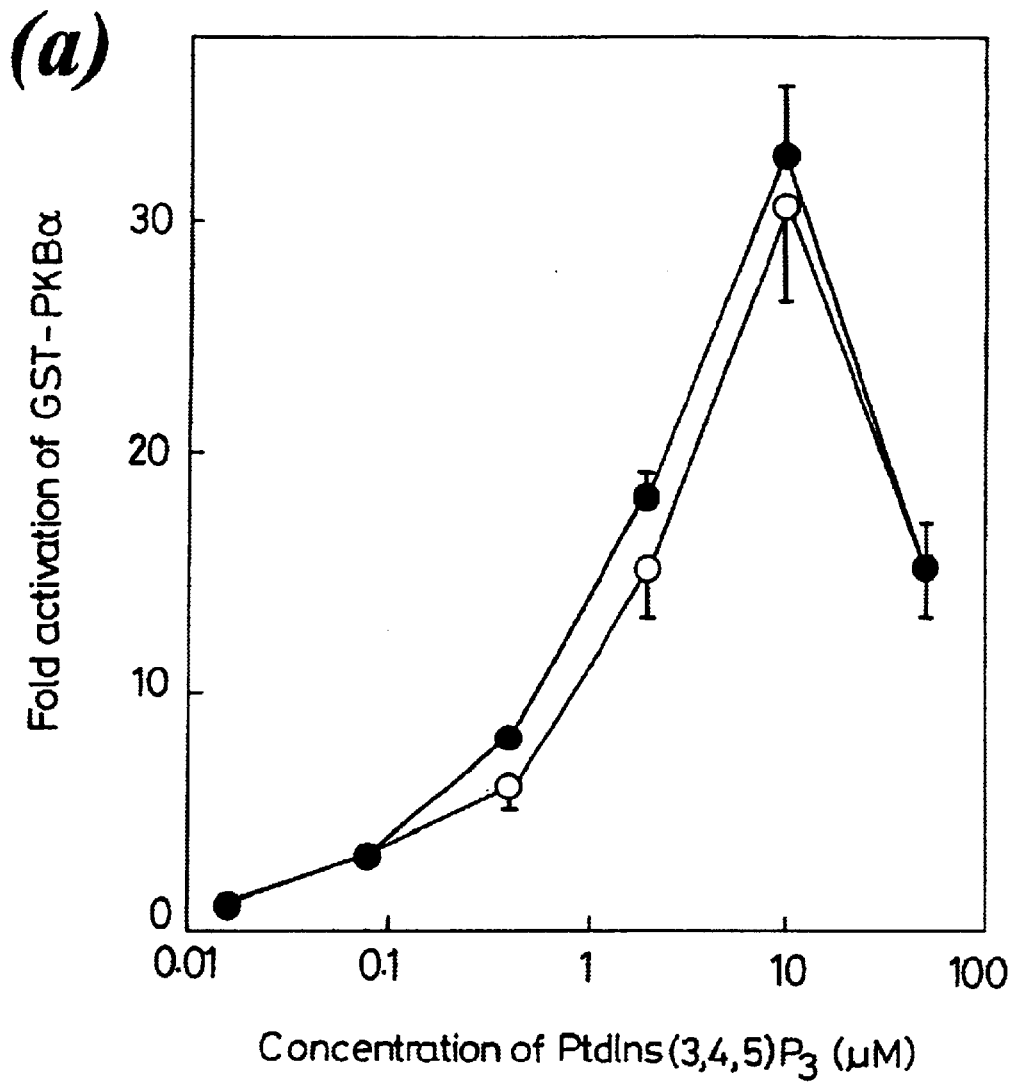
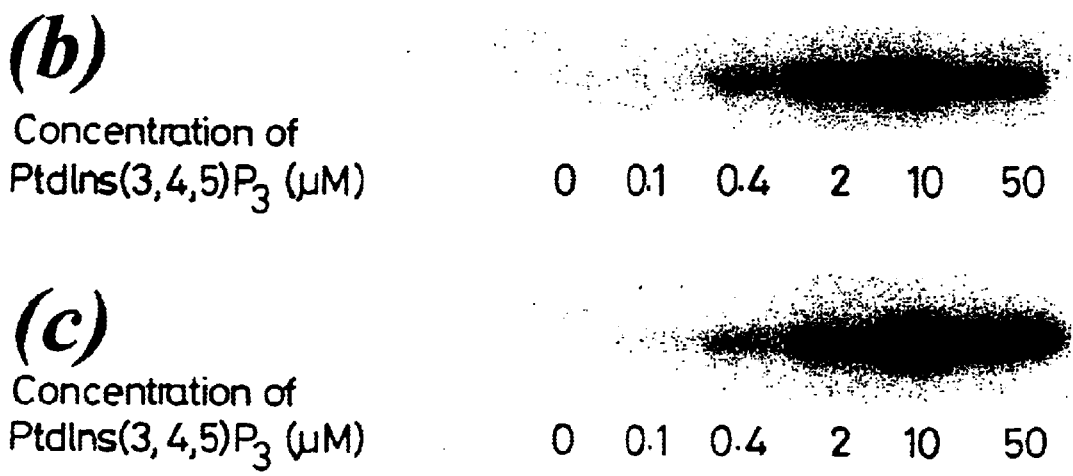
Fig. 4

| NCBI Entrez | DOCUMENT REPORTS | BLAST | Entrez |

Views: | Report | Fasta | Graphic | Save As... |

```
LOCUS       AA121994      419 bp      mRNA           EST        19-NOV-1996
DEFINITION  zm24d12.r1 Stratagene pancreas (#937208) Homo sapiens cDNA clone
            526583 5' similar to TR:G927730 G927730 D8035.10P. ;.
ACCESSION   AA121994
NID         g1677930
KEYWORDS    EST.
SOURCE      human.
  ORGANISM  Homo sapiens
            Eukaryotae; mitochondrial eukaryotes; Metazoa; Chordata;
            Vertebrata; Eutheria; Primates; Catarrhini; Hominidae; Homo.
REFERENCE   1  (bases 1 to 419)
  AUTHORS   Hillier,L., Clark,N., Dubuque,T., Elliston,K., Hawkins,M.,
            Holman,M., Hultman,M., Kucaba,T., Le,M., Lennon,G., Marra,M.,
            Parsons,J., Rifkin,L., Rohlfing,T., Tan,F., Trevaskis,E.,
            Waterston,R., Williamson,A., Wohldmann,P. and Wilson,R.
  TITLE     WashU-Merck EST Project
  JOURNAL   Unpublished (1995)
COMMENT
            Contact: Wilson RK
            WashU-Merck EST Project
            Washington University School of Medicine
            4444 Forest Park Parkway, Box 8501, St. Louis, MO 63108
            Tel: 314 286 1800
            Fax: 314 286 1810
            Email: est@watson.wustl.edu
            This clone is available royalty-free through LLNL ; contact the
            IMAGE Consortium (info@image.llnl.gov) for further information.
            Seq primer: -28M13 rev2 from Amersham
            High quality sequence stop: 343.
FEATURES            Location/Qualifiers
     source         1..419
                    /organism="Homo sapiens"
                    /note="Organ: pancreas; Vector: pBluescript SK-; Site_1:
                    EcoRI; Site_2: XhoI; Cloned unidirectionally. Primer:
                    Oligo dT. Pancreatic adenocarcinoma cell line. Average
                    insert size: 1.0 kb; Uni-ZAP XR Vector; ~5' adaptor
                    sequence: 5' GAATTCGGCACGAG 3' -3' adaptor sequence: 5'
                    CTCGAGTTTTTTTTTTTTTTTTT 3'"
                    /clone="526583"
                    /clone_lib="Stratagene pancreas (#937208)"
                    /lab_host="SOLR cells (kanamycin resistant)"
     mRNA           <1..>419
BASE COUNT        107 a    105 c    107 g     92 t        8 others
ORIGIN
        1 tgagtccagc acgcccctg nattcctgg tggcagcagg cangggccg catggacggc
       61 actgcagccg agcctcgncc agggccggca tcccatgcag catgccagcc tccgccgcag
      121 ctcggaagaa gcggcctgag gacttcaagt tgggaaaac cctggggaag gctctttcnc
      181 acggttgtct ggctcgagaa ctgcaacct ccagagaata cgcgattaaa atnctggaga
      241 agcgacacat cataaaagag aacaaggtcc ctatgtaacc agagantggg atgtcatgtc
      301 gcgcctggat cacccccttct ttgttaagct ttacttcaca tttcaggacg acgagaagnt
      361 gtatttcggc cttagttatg cnaaaaattg gagaactact taaatatatt cgcaaaatc
//
```

*Fig. 8*

NCBI *PubMed*     PubMed QUERY     PubMed ?

Other Formats: Report | FASTA | Graphic

```
LOCUS        AA186323      548 bp    mRNA           EST       13-JAN-1997
DEFINITION   zp80d08.s1 Stratagene HeLa cell s3 937216 Homo sapiens cDNA clone
             626511 3'
ACCESSION    AA186323
NID          g1774441
KEYWORDS     EST.
SOURCE       human.
  ORGANISM   Homo sapiens
             Eukaryotae; mitochondrial eukaryotes; Metazoa; Chordata;
             Vertebrata; Eutheria; Primates; Catarrhini; Hominidae; Homo.
REFERENCE    1 (bases 1 to 548)
  AUTHORS    Hillier,L., Clark,N., Dubuque,T., Elliston,K., Hawkins,M.,
             Holman,M., Hultman,M., Kucaba,T., Le,M., Lennon,G., Marra,M.,
             Parsons,J., Rifkin,L., Rohlfing,T., Tan,F., Trevaskis,E.,
             Waterston,R., Williamson,A., Wohldmann,P. and Wilson,R.
  TITLE      WashU-Merck EST Project
  JOURNAL    Unpublished (1995)
COMMENT
             Contact: Wilson RK
             WashU-Merck EST Project
             Washington University School of Medicine
             4444 Forest Park Parkway, Box 8501, St. Louis, MO 63108
             Tel: 314 286 1800
             Fax: 314 286 1810
             Email: est@watson.wustl.edu
             This clone is available royalty-free through LLNL ; contact the
             IMAGE Consortium (info@image.llnl.gov) for further information.
             Seq primer: -40M13 fwd. from Amersham
             High quality sequence stop: 387.
FEATURES             Location/Qualifiers
     source          1..548
                     /organism="Homo sapiens"
                     /note="Vector: pBluescript SK-; Site_1: EcoRI; Site_2:
                     XhoI; Cloned unidirectionally. Primer: Oligo dT. HeLa S3
                     epithelioid carcinoma cells grown to semi-confluency
                     without induction. Average insert size: 1.5 kb; Uni-ZAP XR
                     Vector. -5' adaptor sequence: 5' GAATTCGGCACGAG 3' -3'
                     adaptor sequence: 5' CTCGAGTTTTTTTTTTTTTTTTTT 3'"
                     /clone="626511"
                     /clone_lib="Stratagene HeLa cell s3 937216"
                     /sex="female"
                     /dev_stage="HeLa S3 cell line"
                     /lab_host="SOLR (kanamycin resistant)"
     mRNA            complement(<1..>548)
BASE COUNT       118 a    144 c    135 g    145 t    6 others
ORIGIN
        1 ttaaataaaa atgctgcaag gtttccgcct ctgcgttccc cttgtgatgg ctggcaggtg
       61 gtctggaagc gtcccggatg gcggccaagc cggcgagggg caggtgtcct ggcagcgaag
      121 ggcagcccgg ccgcacncga tcactgcaca gcggcgtccg ggtggctctg gtatcgctgc
      181 ctccaaacct cctggatctt cctgcaccac ttgtgtgcgt tcccgctggg gtccatcaga
      241 taatacgtcc tgttaggcgt gtggacaaag aaagttttaa aattcttggc ctctggtcna
      301 agttcttgtg accaaggaat ttcacctttc agaactttgt tgacaggatc cacataatat
      361 aaatgtggtc ctctgtgagc aacagctgtc gtcgtcttgc aaataaaccc ttccgcttat
      421 ccactgggcc catctttagt attaaattat tttctacaaa ctggtgncaa gggtttccgc
      481 nagcctggct tctccaacaa caanctcttc tcatcttcgg aaaactgtaa gtccagttca
      541 naggagtt
//
```

*Fig. 9*

Fig. 10 A

```
1081  TACCTGCCGGCTATGTCGGAAGACGACGAGGACTGCTATGGCAATTATGACAATCTCCTGAGCCAGTTTGGCTGCATGCAGGTGTCTTCG
 361   Y  L  P  A  M  S  E  D  D  E  D  C  Y  G  N  Y  D  N  L  L  S  Q  F  G  C  M  Q  V  S  S   390

1171  TCCTCCTCCTCACACTCCCTGTCAGCCTCCGACACGGCCTCAGGCAGCAACATAGAGCAGTACATTCACGATCTGGAC
 391   S  S  S  S  H  S  L  S  A  S  D  T  G  L  P  Q  R  S  G  S  N  I  E  Q  Y  I  H  D  L  D   420

1261  TCGAACTCCTTTGAACTGGACTTACAGTTTTCCGAAGATGAGAAGAGGTTGTTGTTGGAGAAGCAGGCTGGCGGAAACCCTGGCACCAG
 421   S  N  S  F  E  L  D  L  Q  F  S  E  D  E  K  R  L  L  E  K  Q  A  G  G  N  P  W  H  Q   450

1351  TTTGTAGAAAATAATTTAATACTAAAGATGGGCCCAGTGGATAAGCGGAAGGGTTTATTTGAAGACGACAGCTGTTGCTCACAGAA
 451   F  V  E  N  N  L  I  L  K  M  G  P  V  D  K  R  K  G  L  F  A  R  R  R  Q  L  L  T  E   480

1441  GGACCACATTTATATTATGTGGATCCTGTCAACAAAGTTCTGAAAGGTGAAATTCCTTGGTCTCAAGAGCTGCGACCAGAGGCCAAGAAT
 481   G  P  H  L  Y  Y  V  D  P  V  N  K  V  L  K  G  E  I  P  W  S  Q  E  L  R  P  E  A  K  N   510

1531  TTTAAAACTTTCTTTGTCCACACGCCTAACAGGACGTATTATCTGATGGACCCCAGCGGGAACGCACACAAGTGGTGCAGAAGATCCAG
 511   F  K  T  F  F  V  H  T  P  N  R  T  Y  Y  L  M  D  P  S  G  N  A  H  K  W  C  R  K  I  Q   540

1621  GAGGTTTGGAGGCAGCGGTATACCAGCCCGGGACGCCACCCGGCCTGGCCTGACGTGCAGTGCAGTGACGTGCAGTGCTGCCAGACAC
 541   E  V  W  R  Q  R  Y  Q  S  H  P  D  A  A  V  Q  *                                          556

1711  CTGCCCCAGCGCGGCTTGGCCGCCATCCGGGACGCTTCCAGACACCACCTGCCAGCCATCACAAGGGAACGCAGAGGCGAAACCTTGCAG
1801  CATTTTATTT
              1811
```

Fig. 10 B

```
PDK1      -----------  -----------  -----------  -----------  --MARTTSQLYDAVP  IQSSVVLCSCPSPSM  VRTQTESSTPPGIPG      43
DSTPK61   MAKEKASATVSLGES  NFRDINLKDLAVVVE  AASRLHHQQNVCGCG  AVSSTENNNNSRYGS  SKYLTNGHTSPLAAA  VASNSSSVATTPHCR      90

PDK1      GSRQGPAMDGTAAEP  RPGAGSLQHAQPP--  -----------  -----------  -----------  --PQPRKKRPEDFKF  GKILGEGSFSTVVLA      99
DSTPK61   MLHNCSLQQYQNDIR  QCTEILDMLRHEHQQ  GYQSQQQQQQPQQQQ  EQQQQQEQSQQQQQL  QNPAPRRS-PNDFIF  GRYIGEGSYSIVYLA     179
                          *  *            *            *            * **  *****.* ****.*

PDK1      RELATSREYAIKILE  KRHIIKENKVPYVTR  ERDVMSRLD-HPFFV  KLYFTFQDDEKLYFG  LSYAKNGELLKYIRK  IGSFDETCTRFYTAE     188
DSTPK61   VDIHSRREYAIKVCE  KRLILRERKQDYIKR  EREVMHQMTNVPGFV  NLSCTFQDQRSLYFV  MTYARKGDMLPYINR  VGSFDVACTRHYAAE     269
             .  ****** .  **  *.  **  *   **   *    . *****  * *     . *  .* **   * *

PDK1      IVSALEYLHGKGIIH  RDLKPENILLNEDMH  IQITDFGTAKVLS--  -----------  ERALATEHCSEQRRS  NSDEDDEDSDRLENE  DEDFYDRDSEELDDR     231
DSTPK61   LLLACEHMHRRNVVH  RDLKPENILLDEDMH  TLIADFGSAKVMTAH  -----------                                                      359
              .*   .  .* ***********.****   * ***.***  *.

PDK1      -----------  -------PESK  QARAN------  -SFVGT  AQYVSPELLTEKSAC  KSSDLWALGCIIYQL  VAGLPPFRAGNEYLI  FQKIIKLEYDFPEKF     305
DSTPK61   DDEQQQEEMDSPRHR  QRRYNRHRKASFVGT  AQYVSPEVLQMGPIT  PAADLWALGCIVYQM  IAGLPPFRGSNDYVI  FKEILDCAVDFPQGF     449
                          *            ******  *******.* . **     ********.**. ******* . ** *  ****  *  *

PDK1      FPKARDLVEKLLVLD  ATKRLGCEEMEGY-G  PLKAHPFFBSVTWEN  LHQQTPPKLTAVLPA  MSEDDE--DCYGNYD  NLLSQFGCMQVSSSS     392
DSTPK61   DKDAEDLVRKLLRVD  PRDRLGAQDEFGYYE  SIRAHPFFAGIDWQT  LRQQTPPPIYPYLPG  VSQDEDFRSSYTVPG  DLEPGLDERQISRLL     539
           *  *   ****.***    * **   * **     .  ****  . *    *.*****  *.  *                         *

PDK1      SSHSLSASDTGLPQR  SGSNIEQYIHDLDSN  SFELDLQFSEDEKRL  LLEKQAGGNPWHQFV  ENNLILKMGPVDKRK  GLFARRQLLLTEGP     482
DSTPK61   SAELGVGSSVAMPVK  RSTA------KN  SFDLN-----DAEKLQ  RLEQQKTDK-WHVFA  DGEVILKKGFVNKRK  GLFARKMLLLTTGP     615
           *  . . .*    .                     **  *      . *   *.**      **. *        **. ***  *****. ***** **

PDK1      HLYYVDPVNKVLKGE  IPWSQELRPEAKNFK  TFFVHTPNRTYYLMD  PSGNAHKWCRKIQEV  WRQRYQS-HPDAAVQ     556
DSTPK61   RLIYIDPVQMIKKGE  IPWSPDLRAEYKNFK  IFFVHTPNRTYYLDD  PEGYAIHWSEAIENM  RKLAYGDPSSTSAVS  CSSGSSNSLAVISNS     705
           * * ***. . *** ****  . *  *   ****  *************  *.*  . *   *  .       *          **

PDK1      -----------  -------                                                                                       556
DSTPK61   SAASSSNSPTVKRSS  PVNAPQASTASDNRT  LGSTRTGTSPSKKTA  SK                                                    752
```

Fig. 11

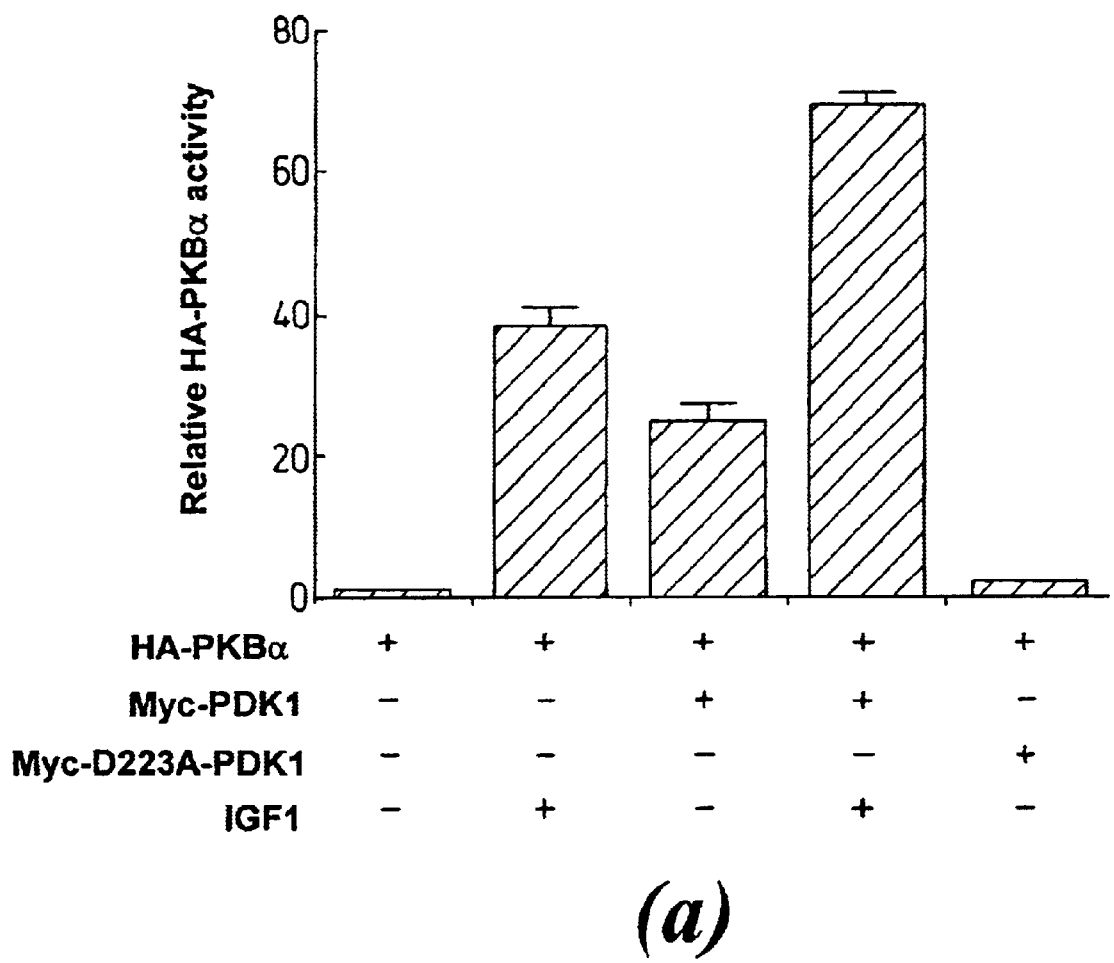
(a)
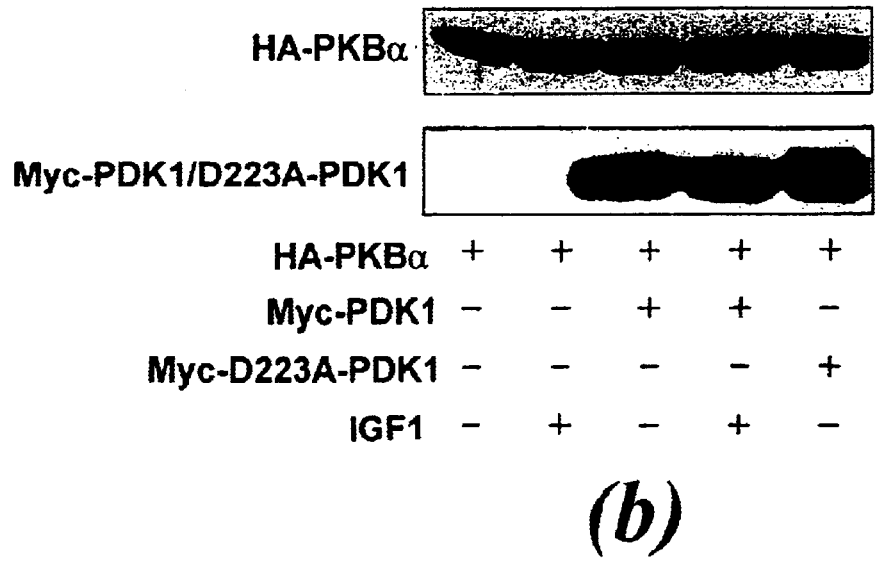
(b)
Fig 14

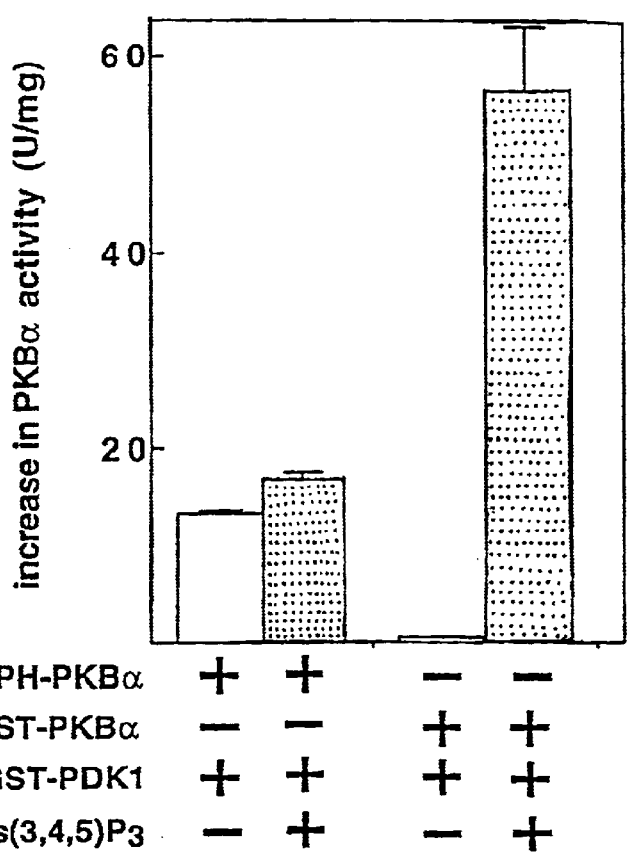
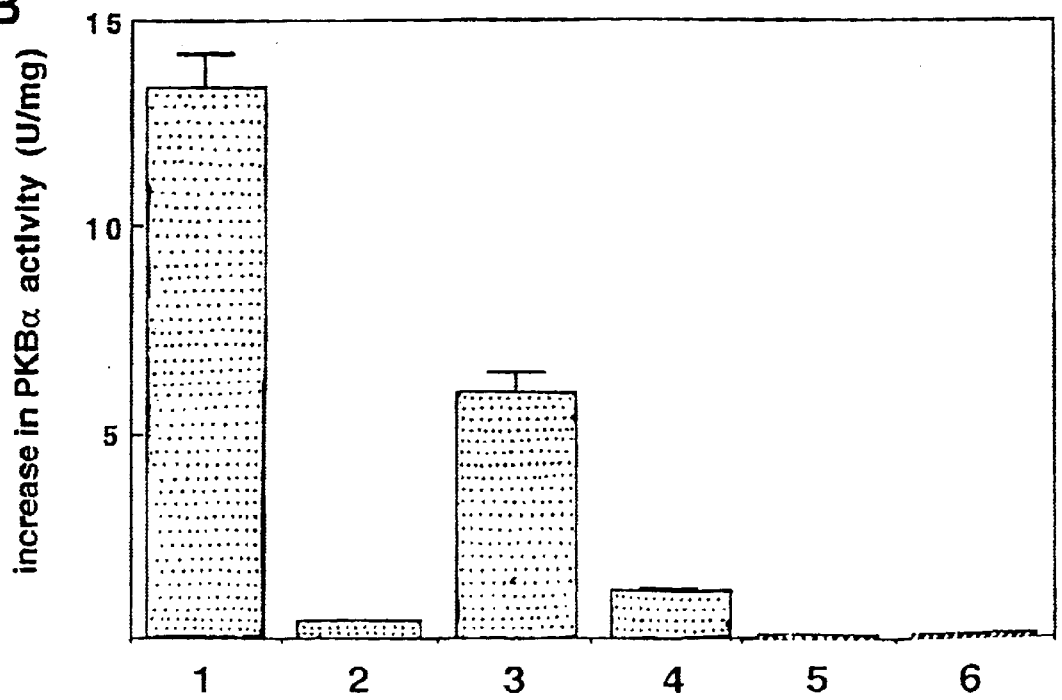
Fig. 16

Fig. 17

SEQUENCE LISTING (1) GENERAL INFORMATION:

(iii) NUMBER OF SEQUENCES: 35

(2) INFORMATION FOR SEQ ID NO: 1:

(i) SEQUENCE CHARACTERISTICS:
      (A) LENGTH: 556 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (vi) ORIGINAL SOURCE:
      (A) ORGANISM: Homo sapiens (xi) SEQUENCE DESCRIPTION: SEQ ID NO: 1:

```
Met Ala Arg Thr Thr Ser Gln Leu Tyr Asp Ala Val Pro Ile Gln Ser
1               5                   10                  15

Ser Val Val Leu Cys Ser Cys Pro Ser Pro Ser Met Val Arg Thr Gln
                20                  25                  30

Thr Glu Ser Ser Thr Pro Pro Gly Ile Pro Gly Gly Ser Arg Gln Gly
            35                  40                  45

Pro Ala Met Asp Gly Thr Ala Ala Glu Pro Arg Pro Gly Ala Gly Ser
        50                  55                  60

Leu Gln His Ala Gln Pro Pro Pro Gln Pro Arg Lys Lys Arg Pro Glu
65                  70                  75                  80

Asp Phe Lys Phe Gly Lys Ile Leu Gly Glu Gly Ser Phe Ser Thr Val
                85                  90                  95

Val Leu Ala Arg Glu Leu Ala Thr Ser Arg Glu Tyr Ala Ile Lys Ile
                100                 105                 110

Leu Glu Lys Arg His Ile Ile Lys Glu Asn Lys Val Pro Tyr Val Thr
            115                 120                 125

Arg Glu Arg Asp Val Met Ser Arg Leu Asp His Pro Phe Phe Val Lys
        130                 135                 140
```

```
Leu Tyr Phe Thr Phe Gln Asp Asp Glu Lys Leu Tyr Phe Gly Leu Ser
145                 150                 155                 160

Tyr Ala Lys Asn Gly Glu Leu Leu Lys Tyr Ile Arg Lys Ile Gly Ser
            165                 170                 175

Phe Asp Glu Thr Cys Thr Arg Phe Tyr Thr Ala Glu Ile Val Ser Ala
            180                 185                 190

Leu Glu Tyr Leu His Gly Lys Gly Ile Ile His Arg Asp Leu Lys Pro
            195                 200                 205

Glu Asn Ile Leu Leu Asn Glu Asp Met His Ile Gln Ile Thr Asp Phe
    210                 215                 220

Gly Thr Ala Lys Val Leu Ser Pro Glu Ser Lys Gln Ala Arg Ala Asn
225                 230                 235                 240

Ser Phe Val Gly Thr Ala Gln Tyr Val Ser Pro Glu Leu Leu Thr Glu
                245                 250                 255

Lys Ser Ala Cys Lys Ser Ser Asp Leu Trp Ala Leu Gly Cys Ile Ile
            260                 265                 270

Tyr Gln Leu Val Ala Gly Leu Pro Pro Phe Arg Ala Gly Asn Glu Tyr
    275                 280                 285

Leu Ile Phe Gln Lys Ile Ile Lys Leu Glu Tyr Asp Phe Pro Glu Lys
    290                 295                 300

Phe Phe Pro Lys Ala Arg Asp Leu Val Glu Lys Leu Leu Val Leu Asp
305                 310                 315                 320

Ala Thr Lys Arg Leu Gly Cys Glu Glu Met Glu Gly Tyr Gly Pro Leu
            325                 330                 335

Lys Ala His Pro Phe Phe Glu Ser Val Thr Trp Glu Asn Leu His Gln
            340                 345                 350

Gln Thr Pro Pro Lys Leu Thr Ala Tyr Leu Pro Ala Met Ser Glu Asp
            355                 360                 365

Asp Glu Asp Cys Tyr Gly Asn Tyr Asp Asn Leu Leu Ser Gln Phe Gly
    370                 375                 380

Cys Met Gln Val Ser Ser Ser Ser Ser His Ser Leu Ser Ala Ser
385                 390                 395                 400

Asp Thr Gly Leu Pro Gln Arg Ser Gly Ser Asn Ile Glu Gln Tyr Ile
                405                 410                 415

His Asp Leu Asp Ser Asn Ser Phe Glu Leu Asp Leu Gln Phe Ser Glu
            420                 425                 430

Asp Glu Lys Arg Leu Leu Leu Glu Lys Gln Ala Gly Gly Asn Pro Trp
            435                 440                 445

His Gln Phe Val Glu Asn Asn Leu Ile Leu Lys Met Gly Pro Val Asp
450                 455                 460

Lys Arg Lys Gly Leu Phe Ala Arg Arg Arg Gln Leu Leu Leu Thr Glu
465                 470                 475                 480

Gly Pro His Leu Tyr Tyr Val Asp Pro Val Asn Lys Val Leu Lys Gly
                485                 490                 495

Glu Ile Pro Trp Ser Gln Glu Leu Arg Pro Glu Ala Lys Asn Phe Lys
            500                 505                 510

Thr Phe Phe Val His Thr Pro Asn Arg Thr Tyr Tyr Leu Met Asp Pro
            515                 520                 525

Ser Gly Asn Ala His Lys Trp Cys Arg Lys Ile Gln Glu Val Trp Arg
            530                 535                 540

Gln Arg Tyr Gln Ser His Pro Asp Ala Ala Val Gln
545                 550                 555
```

(2) INFORMATION FOR SEQ ID NO: 2:

(i) SEQUENCE CHARACTERISTICS:
        (A) LENGTH: 1670 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO: 2:

```
ATGGCCAGGA CCACCAGCCA GCTGTATGAC GCCGTGCCCA TCCAGTCCAG CGTGGTGTTA      60
TGTTCCTGCC CATCCCCATC AATGGTGAGG ACCCAGACTG AGTCCAGCAC GCCCCCTGGC     120
ATTCCTGGTG GCAGCAGGCA GGGCCCCGCC ATGGACGGCA CTGCAGCCGA GCCTCGGCCC     180
GGCGCCGGCT CCCTGCAGCA TCCCAGCCTC CGCCGCAGCC TCGGAAGAAG CGGCCTGAGG     240
ACTTCAAGTT TGGGAAAATC CTTGGGGAAG GCTCTTTTTC CACGGTTGTC CTGGCTCGAG     300
AACTGGCAAC CTCCAGAGAA TATGCGATTA AAATTCTGGA GAAGCGACAT ATCATAAAAG     360
AGAACAAGGT CCCCTATGTA ACCAGAGAGC GGGATGTCAT GTCGCGCCTG GATCACCCCT     420
TCTTTGTTAA GCTTTACTTC ACATTTCAGG ACGACGAGAA GCTGTATTTC GGCCTTAGTT     480
ATGCCAAAAA TGGAGAACTA CTTAAATATA TTCGCAAAAT CGGTTCATTC GATGAGACCT     540
GTACCCGATT TTACACGGCT GAGATCGTGT CTGCTTTAGA GTACTTGCAC GGCAAGGGCA     600
TCATTCACAG GGACCTTAAA CCGGAAAACA TTTTGTTAAA TGAAGATATG CACATCCAGA     660
TCACAGATTT TGGAACAGCA AAAGTCTTAT CCCCAGAGAG CAAACAAGCC AGGGCCAACT     720
CATTCGTGGG AACAGCGCAG TACGTTTCTC CAGAGCTGCT CACGGAGAAG TCCGCCTGTA     780
AGAGTTCAGA CCTTTGGGCT CTTGGATGCA TAATATACCA GCTTGTGGCA GGACTCCCAC     840
CATTCCGAGC TGGAAACGAG TATCTTATAT TTCAGAAGAT CATTAAGTTG GAATATGACT     900
TTCCAGAAAA ATTCTTCCCT AAGGCAAGAG ACCTCGTGGA GAAACTTTTG GTTTTAGATG     960
CCACAAAGCG GTTAGGCTGT GAGGAAATGG AAGGATACGG ACCTCTTAAA GCACACCCGT    1020
TCTTCGAGTC CGTCACGTGG GAGAACCTGC ACCAGCAGAC GCCTCCGAAG CTCACCGCTT    1080
ACCTGCCGGC TATGTCGGAA GACGACGAGG ACTGCTATGG CAATTATGAC AATCTCCTGA    1140
GCCAGTTTGG CTGCATGCAG GTGTCTTCGT CCTCCTCCTC ACACTCCCTG TCAGCCTCCG    1200
ACACGGGCCT GCCCCAGAGG TCAGGCAGCA ACATAGAGCA GTACATTCAC GATCTGGACT    1260
CGAACTCCTT TGAACTGGAC TTACAGTTTT CCGAAGATGA GAAGAGGTTG TTGTTGGAGA    1320
AGCAGGCTGG CGGAAACCCT TGGCACCAGT TTGTAGAAAA TAATTTAATA CTAAAGATGG    1380
GCCCAGTGGA TAAGCGGAAG GGTTTATTTG CAAGACGACG ACAGCTGTTG CTCACAGAAG    1440
GACCACATTT ATATTATGTG GATCCTGTCA ACAAAGTTCT GAAAGGTGAA ATTCCTTGGT    1500
CACAAGAACT TCGACCAGAG GCCAAGAATT TTAAAACTTT CTTTGTCCAC ACGCCTAACA    1560
GGACGTATTA TCTGATGGAC CCCAGCGGGA ACGCACACAA GTGGTGCAGG AAGATCCAGG    1620
AGGTTTGGAG GCAGCGATAC CAGAGCCACC CGGACGCCGC TGTGCAGTGA                1670
```

(2) INFORMATION FOR SEQ ID NO: 3:

(i) SEQUENCE CHARACTERISTICS:
    (A) LENGTH: 16 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 3:

```
Ala Asn Ser Phe Val Gly Thr Ala Gln Tyr Val Ser Pro Glu Leu Leu
1               5                  10                  15
```

(2) INFORMATION FOR SEQ ID NO: 4:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 4:

```
Ala Gly Asn Glu Tyr Leu Ile Phe Gln Lys
1               5                  10
```

(2) INFORMATION FOR SEQ ID NO: 5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 5:

```
Leu Asp His Pro Phe Phe Val Lys
1               5
```

(2) INFORMATION FOR SEQ ID NO: 6:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 6:

```
Arg Gln Arg Tyr Gln Ser His Pro Asp Ala Ala Val Gln
1               5                   10
```

(2) INFORMATION FOR SEQ ID NO: 7:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 7:

```
Leu Ser Pro Glu Ser Lys Gln Ala Arg Ala Asn Ser
1               5                   10
```

(2) INFORMATION FOR SEQ ID NO: 8:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 8:

```
Thr Ala Ser Gly Val Ala Glu Thr Thr Asn Cys
1               5                   10
```

(2) INFORMATION FOR SEQ ID NO: 9:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 9:

```
Arg Pro Arg Ala Ala Thr Phe
1               5
```

(2) INFORMATION FOR SEQ ID NO: 10:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 10:

Thr Thr Tyr Ala Asp Phe Ile Ala Ser Gly Arg Thr Gly Arg Arg Asn
1               5                  10                  15

Ala Ile His Asp
            20

(2) INFORMATION FOR SEQ ID NO: 11:

(i) SEQUENCE CHARACTERISTICS:
             (A) LENGTH: 20 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 11:

Ala His Pro Phe Phe Glu Ser Val Thr Trp Glu Asn Leu His Gln Gln
1               5                  10                  15

Thr Pro Pro Lys
            20

(2) INFORMATION FOR SEQ ID NO: 12:

(i) SEQUENCE CHARACTERISTICS:
             (A) LENGTH: 21 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 12:

Ser Gly Ser Asn Ile Glu Gln Tyr Ile His Asp Leu Asp Ser Asn Ser
1               5                  10                  15

Phe Glu Leu Asp Leu
            20

(2) INFORMATION FOR SEQ ID NO: 13:

(i) SEQUENCE CHARACTERISTICS:
             (A) LENGTH: 18 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 13:

Gln Ala Gly Gly Asn Pro Trp His Gln Phe Val Glu Asn Asn Leu Ile
1               5                  10                  15
Leu Lys (2) INFORMATION FOR SEQ ID NO: 14:

(i) SEQUENCE CHARACTERISTICS:
             (A) LENGTH: 18 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 14:

Gln Leu Leu Leu Thr Glu Gly Pro His Leu Tyr Tyr Val Asp Pro Val
1               5                  10                  15
Asn Lys (2) INFORMATION FOR SEQ ID NO: 15:

(i) SEQUENCE CHARACTERISTICS:
             (A) LENGTH: 9 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 15:

Thr Phe Phe Val His Thr Pro Asn Arg
1               5

(2) INFORMATION FOR SEQ ID NO: 16:

(i) SEQUENCE CHARACTERISTICS:
             (A) LENGTH: 10 amino acids
             (B) TYPE: amino acid
             (C) STRANDEDNESS: single
             (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 16:

Tyr Gln Ser His Pro Asp Ala Ala Val Gln
1               5                  10

(2) INFORMATION FOR SEQ ID NO: 17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER"

(iii) HYPOTHETICAL: NO (iv) ANTI-SENSE: NO (xi) SEQUENCE DESCRIPTION: SEQ ID NO: 17:

CTGAGCCAGT TTGGCTGC         18

(2) INFORMATION FOR SEQ ID NO: 18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER"

(xi) SEQUENCE DESCRIPTION: SEQ ID NO: 18:

ACGTCCTGTT AGGCGTGTGG         20

(2) INFORMATION FOR SEQ ID NO: 19:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER"

(iii) HYPOTHETICAL: NO (iv) ANTI-SENSE: NO (xi) SEQUENCE DESCRIPTION: SEQ ID NO: 19:

TTTGTKGGNA CNGCNCARTA YGT         23

(2) INFORMATION FOR SEQ ID NO: 20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR PRIMER"

(iii) HYPOTHETICAL: NO (iv) ANTI-SENSE: NO (xi) SEQUENCE DESCRIPTION: SEQ ID NO: 20:

TTNACRAARA ANGGRTGRTC         20

(2) INFORMATION FOR SEQ ID NO: 21:

```
         (i) SEQUENCE CHARACTERISTICS:
             (A) LENGTH: 23 base pairs
             (B) TYPE: nucleic acid
             (C) STRANDEDNESS: single
             (D) TOPOLOGY: linear (ii) MOLECULE TYPE: other nucleic acid
             (A) DESCRIPTION:   /desc = "PCR PRIMER"

(iii) HYPOTHETICAL: NO (iv) ANTI-SENSE: NO (xi) SEQUENCE DESCRIPTION: SEQ ID NO: 21:

AAYGARTAYY TNATHTTYCA RAA                                              23

(2) INFORMATION FOR SEQ ID NO: 22:

(i) SEQUENCE CHARACTERISTICS:
             (A) LENGTH: 73 base pairs
             (B) TYPE: nucleic acid
             (C) STRANDEDNESS: single
             (D) TOPOLOGY: linear (ii) MOLECULE TYPE: other nucleic acid
             (A) DESCRIPTION:   /desc = "PCR PRIMER"

(iii) HYPOTHETICAL: NO (iv) ANTI-SENSE: NO (xi) SEQUENCE DESCRIPTION: SEQ ID NO: 22:

GCGGAGATCT GCCACCATGG AGCAGAAGCT GATCTCTGAA GAGGACTTGG ACGGCACTGC      60

AGCCGAGCCT CGG                                                        73

(2) INFORMATION FOR SEQ ID NO: 23:

(i) SEQUENCE CHARACTERISTICS:
             (A) LENGTH: 34 base pairs
             (B) TYPE: nucleic acid
             (C) STRANDEDNESS: single
             (D) TOPOLOGY: linear (ii) MOLECULE TYPE: other nucleic acid
             (A) DESCRIPTION:   /desc = "PCR PRIMER"

(iii) HYPOTHETICAL: NO (iv) ANTI-SENSE: NO (xi) SEQUENCE DESCRIPTION: SEQ ID NO: 23:

GCGGGGTACC TCACTGCACA GCGGCGTCCG GGTG                                  34

(2) INFORMATION FOR SEQ ID NO: 24:

(i) SEQUENCE CHARACTERISTICS:
             (A) LENGTH: 77 base pairs
             (B) TYPE: nucleic acid
             (C) STRANDEDNESS: single
             (D) TOPOLOGY: linear (ii) MOLECULE TYPE: other nucleic acid
             (A) DESCRIPTION:   /desc = "PCR PRIMER"

(iii) HYPOTHETICAL: NO (iv) ANTI-SENSE: NO (xi) SEQUENCE DESCRIPTION: SEQ ID NO: 24:

GCGGAGATCT GCCACCATGG AGCAGAAGCT GATCTCTGAA GAGGACTTGG CCAGGACCAC      60
```

```
CAGCCAGCTG TATGACG                                                          77

(2) INFORMATION FOR SEQ ID NO: 25:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "PCR PRIMER"

(iii) HYPOTHETICAL: NO (iv) ANTI-SENSE: NO (xi) SEQUENCE DESCRIPTION: SEQ ID NO: 25:

GCGGGGTACC TCAGTGCCAA GGGTTTCCGC CAGCCTGCTT                                  40

(2) INFORMATION FOR SEQ ID NO: 26:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "PCR PRIMER"

(iii) HYPOTHETICAL: NO (iv) ANTI-SENSE: NO (xi) SEQUENCE DESCRIPTION: SEQ ID NO: 26:

CGGGATCCAT GGACTTCCGG TCGGGCTCA                                              29

(2) INFORMATION FOR SEQ ID NO: 27:

(i) SEQUENCE CHARACTERISTICS:
        (A) LENGTH: 419 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 27:

TGAGTCCAGC ACGCCCCCTG NATTTCCTGG TGGCAGCAGG CANGGGCCCG CATGGACGGC            60

ACTGCAGCCG AGCCTCGNCC AGGGCCGGCA TCCCATGCAG CATGCCAGCC TCCGCCGCAG           120

CTCGGAAGAA GCGGCCTGAG GACTTCAAGT TTGGGAAAAT CTTGGGGAAG GCTCTTTTNC           180

ACGGTTGTCT GGCTCGAGAA CTGGCAACCT CCAGAGAATA TGCGATTAAA ATNCTGGAGA          240

AGCGACATAT CATAAAAGAG AACAAGGTCC CTATGTAACC AGAGANTGGG ATGTCATGTC           300

GCGCCTGGAT CACCCCTTCT TGTTAAGCT TTACTTCACA TTTCAGGACG ACGAGAAGNT            360

GTATTTCGGC CTTAGTTATG CNAAAAATTG GAGAACTACT TAAATATATT CGCAAAATC           419

(2) INFORMATION FOR SEQ ID NO: 28:
```

```
    (i) SEQUENCE CHARACTERISTICS:
        (A) LENGTH: 548 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Human (xi) SEQUENCE DESCRIPTION: SEQ ID NO: 28:

TTAAATAAAA ATGCTGCAAG GTTTCCGCCT CTGCGTTCCC CTTGTGATGG CTGGCAGGTG      60

GTCTGGAAGC GTCCCGGATG GCGGCCAAGC CGGCGAGGGG CAGGTGTCCT GGCAGCGAAG     120

GGCAGCCCGG CCGCACNCGA TCACTGCACA GCGGCGTCCG GGTGGCTCTG GTATCGCTGC     180

CTCCAAACCT CCTGGATCTT CCTGCACCAC TTGTGTGCGT TCCCGCTGGG GTCCATCAGA     240

TAATACGTCC TGTTAGGCGT GTGGACAAAG AAAGTTTTAA AATTCTTGGC CTCTGGTCNA     300

AGTTCTTGTG ACCAAGGAAT TCACCTTTC AGAACTTTGT TGACAGGATC CACATAATAT      360

AAATGTGGTC CTCTGTGAGC AACAGCTGTC GTCGTCTTGC AAATAAACCC TTCCGCTTAT     420

CCACTGGGCC CATCTTTAGT ATTAAATTAT TTTCTACAAA CTGGTGNCAA GGGTTTCCGC     480

NAGCCTGGCT TCTCCAACAA CAANCTCTTC TCATCTTCGG AAAACTGTAA GTCCAGTTCA     540

NAGGAGTT                                                              548

(2) INFORMATION FOR SEQ ID NO: 29:

(i) SEQUENCE CHARACTERISTICS:
        (A) LENGTH: 752 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Drosophila (xi) SEQUENCE DESCRIPTION: SEQ ID NO: 29:

Met Ala Lys Glu Lys Ala Ser Ala Thr Val Ser Leu Gly Glu Ser Asn
1               5                  10                  15

Phe Arg Asp Ile Asn Leu Lys Asp Leu Ala Val Val Glu Ala Ala
            20                  25                  30

Ser Arg Leu His His Gln Gln Asn Val Cys Gly Cys Gly Ala Val Ser
        35                  40                  45

Ser Thr Glu Asn Asn Asn Asn Ser Arg Tyr Gly Ser Ser Lys Tyr Leu
    50                  55                  60

Thr Asn Gly His Thr Ser Pro Leu Ala Ala Val Ala Ser Asn Ser
65                  70                  75                  80

Ser Ser Val Ala Thr Thr Pro His Cys Arg Met Leu His Asn Cys Ser
                85                  90                  95

Leu Gln Gln Tyr Gln Asn Asp Ile Arg Gln Gln Thr Glu Ile Leu Asp
            100                 105                 110

Met Leu Arg His Glu His Gln Gln Gly Tyr Gln Ser Gln Gln Gln Gln
```

```
            115                 120                 125
Gln Gln Pro Gln Gln Gln Glu Gln Gln Gln Gln Glu Gln Ser
        130                 135                 140
Gln Gln Gln Gln Gln Leu Gln Asn Pro Ala Pro Arg Ser Pro Asn
145                 150                 155                 160
Asp Phe Ile Phe Gly Arg Tyr Ile Gly Glu Gly Ser Tyr Ser Ile Val
                165                 170                 175
Tyr Leu Ala Val Asp Ile His Ser Arg Arg Glu Tyr Ala Ile Lys Val
            180                 185                 190
Cys Glu Lys Arg Leu Ile Leu Arg Glu Arg Lys Gln Asp Tyr Ile Lys
        195                 200                 205
Arg Glu Arg Glu Val Met His Gln Met Thr Asn Val Pro Gly Phe Val
        210                 215                 220
Asn Leu Ser Cys Thr Phe Gln Asp Ala Arg Ser Leu Tyr Phe Val Met
225                 230                 235                 240
Thr Tyr Ala Arg Lys Gly Asp Met Leu Pro Tyr Ile Asn Arg Val Gly
                245                 250                 255
Ser Phe Asp Val Ala Cys Thr Arg His Tyr Ala Ala Glu Leu Leu Leu
            260                 265                 270
Ala Cys Glu His Met His Arg Arg Asn Val Val His Arg Asp Leu Lys
        275                 280                 285
Pro Glu Asn Ile Leu Leu Asp Glu Asp Met His Thr Leu Ile Ala Asp
        290                 295                 300
Phe Gly Ser Ala Lys Val Met Thr Ala His Glu Arg Ala Leu Ala Thr
305                 310                 315                 320
Glu His Cys Ser Glu Gln Arg Arg Ser Asn Ser Asp Glu Asp Asp Glu
                325                 330                 335
Asp Ser Asp Arg Leu Glu Asn Glu Asp Glu Asp Phe Tyr Asp Arg Asp
            340                 345                 350
Ser Glu Glu Leu Asp Asp Arg Asp Glu Gln Gln Gln Glu Glu Met
        355                 360                 365
Asp Ser Pro Arg His Arg Gln Arg Tyr Asn Arg His Arg Lys Ala
        370                 375                 380
Ser Phe Val Gly Thr Ala Gln Tyr Val Ser Pro Glu Val Leu Gln Asn
385                 390                 395                 400
Gly Pro Ile Thr Pro Ala Ala Asp Leu Trp Ala Leu Gly Cys Ile Val
                405                 410                 415
Tyr Gln Met Ile Ala Gly Leu Pro Pro Phe Arg Gly Ser Asn Asp Tyr
            420                 425                 430
Val Ile Phe Lys Glu Ile Leu Asp Cys Ala Val Asp Phe Pro Gln Gly
        435                 440                 445
Phe Asp Lys Asp Ala Glu Asp Leu Val Arg Lys Leu Leu Arg Val Asp
450                 455                 460
Pro Arg Asp Arg Leu Gly Ala Gln Asp Glu Phe Gly Tyr Tyr Glu Ser
465                 470                 475                 480
Ile Arg Ala His Pro Phe Phe Ala Gly Ile Asp Trp Gln Thr Leu Arg
                485                 490                 495
Gln Gln Thr Pro Pro Pro Ile Tyr Pro Tyr Leu Pro Gly Val Ser Gln
            500                 505                 510
Asp Glu Asp Phe Arg Ser Ser Tyr Thr Val Pro Gly Asp Leu Glu Pro
        515                 520                 525
Gly Leu Asp Glu Arg Gln Ile Ser Arg Leu Leu Ser Ala Glu Leu Gly
        530                 535                 540
```

-continued

```
Val Gly Ser Ser Val Ala Met Pro Val Lys Arg Ser Thr Ala Lys Asn
545                 550                 555                 560

Ser Phe Asp Leu Asn Asp Ala Glu Lys Leu Gln Arg Leu Glu Gln Gln
                565                 570                 575

Lys Thr Asp Lys Trp His Val Phe Ala Asp Gly Glu Val Ile Leu Lys
            580                 585                 590

Lys Gly Phe Val Asn Lys Arg Lys Gly Leu Phe Ala Arg Lys Arg Met
        595                 600                 605

Leu Leu Leu Thr Thr Gly Pro Arg Leu Ile Tyr Ile Asp Pro Val Gln
    610                 615                 620

Met Ile Lys Lys Gly Glu Ile Pro Trp Ser Pro Asp Leu Arg Ala Glu
625                 630                 635                 640

Tyr Lys Asn Phe Lys Ile Phe Phe Val His Thr Pro Asn Arg Thr Tyr
                645                 650                 655

Tyr Leu Asp Asp Pro Glu Gly Tyr Ala Ile His Trp Ser Glu Ala Ile
                660                 665                 670

Glu Asn Met Arg Lys Leu Ala Tyr Gly Asp Pro Ser Ser Thr Ser Ala
            675                 680                 685

Val Ser Cys Ser Ser Gly Ser Ser Asn Ser Leu Ala Val Ile Ser Asn
        690                 695                 700

Ser Ser Ala Ala Ser Ser Ser Asn Ser Pro Thr Val Lys Arg Ser Ser
705                 710                 715                 720

Pro Val Asn Ala Pro Gln Ala Ser Thr Ala Ser Asp Asn Arg Thr Leu
                725                 730                 735

Gly Ser Thr Arg Thr Gly Thr Ser Pro Ser Lys Lys Thr Ala Ser Lys
            740                 745                 750
```

(2) INFORMATION FOR SEQ ID NO: 30:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 30:

```
Lys Met Gly Pro Val Asp Lys Arg Lys Gly Leu Phe Ala Arg Arg Arg
1               5                   10                  15

Gln Leu Leu Leu Thr Glu Gly Pro His Leu Tyr Tyr Val Asp Pro Val
            20                  25                  30

Asn Lys Val Leu Lys Gly Glu Ile Pro Trp Ser Gln Glu Leu Arg Pro
        35                  40                  45

Glu Ala Lys Asn Phe Lys Thr Phe Phe Val His Thr Pro Asn Arg Thr
    50                  55                  60

Tyr Tyr Leu Met Asp Pro Ser Gly Asn Ala His Lys Trp Cys Arg Lys
65                  70                  75                  80

Ile Gln Glu Val Trp Arg Gln Arg Tyr Gln Ser His
                85                  90
```

(2) INFORMATION FOR SEQ ID NO: 31:

(i) SEQUENCE CHARACTERISTICS:
    (A) LENGTH: 92 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 31:

```
Lys Lys Gly Phe Val Asn Lys Arg Lys Gly Leu Phe Ala Arg Lys Arg
1               5                   10                  15

Met Leu Leu Thr Thr Gly Pro Arg Leu Ile Tyr Ile Asp Pro Val
            20                  25                  30

Gln Met Ile Lys Lys Gly Glu Ile Pro Trp Ser Pro Asp Leu Arg Ala
        35                  40                  45

Glu Tyr Lys Asn Phe Lys Ile Phe Phe Val His Thr Pro Asn Arg Thr
    50                  55                  60

Tyr Tyr Leu Asp Asp Pro Glu Gly Tyr Ala Ile His Trp Ser Glu Ala
65              70                  75                  80

Ile Glu Asn Met Arg Lys Leu Ala Tyr Gly Asp Pro
                85                  90
```

(2) INFORMATION FOR SEQ ID NO: 32:

(i) SEQUENCE CHARACTERISTICS:
    (A) LENGTH: 101 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 32:

```
Arg Glu Gly Tyr Leu Val Lys Lys Gly Ser Val Phe Asn Thr Trp Lys
1               5                   10                  15

Pro Met Trp Val Val Leu Leu Glu Asp Gly Ile Glu Phe Tyr Lys Lys
            20                  25                  30

Lys Ser Asp Asn Ser Pro Lys Gly Met Ile Pro Leu Lys Gly Ser Thr
        35                  40                  45

Leu Thr Ser Pro Cys Gln Asp Phe Gly Lys Arg Met Phe Val Phe Lys
    50                  55                  60

Ile Thr Thr Thr Lys Gln Gln Asp His Phe Phe Gln Ala Ala Phe Leu
65              70                  75                  80

Glu Glu Arg Asp Ala Trp Val Arg Asp Ile Asn Lys Ala Ile Lys Cys
                85                  90                  95

Ile Glu Gly Leu Glu
                100
```

(2) INFORMATION FOR SEQ ID NO: 33:

(i) SEQUENCE CHARACTERISTICS:

(A) LENGTH: 112 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 33:

Met Glu Gly Phe Leu Asn Arg Lys His Glu Trp Ala His Asn Lys
1               5                   10                  15

Lys Ala Ser Ser Arg Ser Trp His Asn Val Tyr Gly Val Ile Asn Asn
            20                  25                  30

Gln Glu Met Gly Phe Tyr Lys Asp Ala Lys Ser Ala Ala Ser Gly Ile
            35                  40                  45

Pro Tyr His Ser Glu Val Pro Val Ser Leu Lys Glu Ala Ile Cys Glu
    50                  55                  60

Val Ala Leu Asp Tyr Lys Lys Lys His Val Phe Lys Leu Arg Leu
65                  70                  75                  80

Ser Asp Gly Asn Glu Tyr Leu Phe Gln Ala Lys Asp Asp Glu Glu Met
                85                  90                  95

Asn Thr Trp Ile Gln Ala Ile Ser Ser Ala Ile Ser Ser Asp Lys His
                100                 105                 110

(2) INFORMATION FOR SEQ ID NO: 34:

(i) SEQUENCE CHARACTERISTICS:
        (A) LENGTH: 109 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 34:

Arg Lys Gly Trp Leu Thr Ile Asn Asn Ile Gly Ile Met Lys Gly Gly
1               5                   10                  15

Ser Lys Glu Tyr Trp Phe Val Leu Thr Ala Glu Asn Leu Ser Trp Tyr
            20                  25                  30

Lys Asp Asp Glu Glu Lys Glu Lys Lys Tyr Met Leu Ser Val Asp Asn
            35                  40                  45

Leu Lys Leu Arg Asp Val Glu Lys Gly Phe Met Ser Ser Lys His Ile
    50                  55                  60

Phe Ala Leu Phe Asn Thr Glu Gln Arg Asn Val Tyr Lys Asp Tyr Arg
65                  70                  75                  80

Gln Leu Glu Leu Ala Cys Glu Thr Gln Glu Glu Val Asp Ser Trp Lys
                85                  90                  95

Ala Ser Phe Leu Arg Ala Gly Val Tyr Pro Glu Arg Val
                100                 105

(2) INFORMATION FOR SEQ ID NO: 35:

-continued

```
    (i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO: 35:

Lys Gly Ser Gln Leu Leu Lys Val Lys Ser Ser Ser Trp Arg Arg Glu
1               5                   10                  15

Arg Phe Tyr Lys Leu Gln Glu Asp Cys Lys Thr Ile Trp Gln Glu Ser
            20                  25                  30

Arg Lys Val Met Arg Ser Pro Glu Ser Gln Leu Phe Ser Ile Glu Asp
            35                  40                  45

Ile Gln Glu Val Arg Met Gly His Arg Thr Glu Gly Leu Glu Lys Phe
    50                  55                  60

Ala Arg Asp Ile Pro Glu Asp Arg Cys Phe Ser Ile Val Phe Lys Asp
65                  70                  75                  80

Gln Arg Asn Thr Leu Asp Ile Ala Pro Ser Pro Ala Asp Ala Gln His
                85                  90                  95

Trp Val Gln Gly Leu Arg Lys Ile Ile His His Ser Gly Ser Met Asp
            100                 105                 110

Gln Arg
```

3-PHOSPHOINOSITIDE-DEPENDENT PROTEIN KINASE

The present invention relates to enzymes, to polynucleotides encoding enzymes and to uses of enzymes and polynucleotides.

Protein kinase B (PKB) [1] or RAC protein kinase [2] is the cellular homologue of a viral oncogene v-Akt [3] and has therefore also been termed c-Akt. The current interest in PKB stems firstly from the discovery that it is activated rapidly in response to insulin and growth factors and that the activation is prevented by inhibitors of phosphoinositide (PI) 3-kinase [4–6]; secondly, from the finding that PKB isoforms are overexpressed in a significant percentage of ovarian, pancreatic [7, 8] and breast cancer cells [2].

PKB appears to mediate the insulin-induced inhibition of glycogen synthase kinase-3 (GSK3) in L6 myotubes which is thought to underlie, at least in part, the insulin-induced dephosphorylation and activation of glycogen synthase [9] and protein synthesis initiation factor eIF2 [10] that contribute to the stimulation of glycogen and protein synthesis by insulin. However PKB is likely to have other physiological substrates and, in transfection based experiments, has been shown to activate p70 S6 kinase [5], to stimulate the translocation of the glucose transporter GLUT4 to the plasma membrane and enhance glucose uptake into 3T3-L1 adipocytes [11], and to mediate the IGF1-induced survival of neurones [12] and fibroblasts [13] against apoptosis.

A critical question concerns the mechanism by which PI 3-kinase triggers the activation of PKB. The activation of PKB is accompanied by its phosphorylation [5,14] and we recently showed that activation by insulin or IGF1 resulted from its phosphorylation at Thr-308 and Ser-473 [15].

Moreover, the insulin or IGF1 induced phosphorylation of both residues was abolished by wortmannin, an inhibitor of PI 3-kinase [15]. We believe that the protein kinases which phosphorylate PKB at Thr-308 and Ser-473 might themselves be activated by phosphatidylinositol 3,4,5 trisphosphate (PtdIns(3,4,5)P3), the product of the PI 3-kinase reaction. In the work presented here, we demonstrate that this is indeed the case, and we describe the purification and characterisation of a 3-phosphoinositide-dependent protein kinase (PDK1) which activates PKB and we disclose polynucleotides which encode PDK1 and uses for PDK1 and said polynucleotides.

A first aspect of the invention provides a substantially pure 3-phosphoinositide dependent protein kinase that phosphorylates and activates protein kinase Bα.

By "substantially pure" we mean that the 3-phosphoinositide-dependent protein kinase is substantially free of other proteins. Thus, we include any composition that includes at least 30% of the protein content by weight as the said 3-phosphoinositide-dependent protein kinase, preferably at least 50%, more preferably at least 70%, still more preferably at least 90% and most preferably at least 95% of the protein content is the said 3-phosphoinositide-dependent protein kinase.

Thus, the invention also includes compositions comprising the 3-phosphoinositide-dependent protein kinase and a contaminant wherein the contaminant comprises less than 70% of the composition by weight, preferably less than 50% of the composition, more preferably less than 30% of the composition, still more preferably less than 10% of the composition and most preferably less than 5% of the composition by weight.

The invention also includes the substantially pure said 3-phosphoinositide-endent protein kinase when combined with other components ex vivo, said other components not being all of the components found in the cell in which said protein kinase is found.

It is preferred that the substantially pure 3-phosphoinositide-dependent protein kinase is a substantially pure phosphatidyl-3,4-5-trisphosphate-dependent protein kinase or a substantially pure phosphatidyl-3,4-bisphosphate-dependent protein kinase.

By "phosphorylates protein kinase Bα" we include the meaning that the 3-phosphoinositide-dependent protein kinase is able to transfer a phosphate group from ATP to an acceptor group of protein kinase Bα. Preferably, the acceptor group is Thr-308.

By "protein kinase Bα" we include any protein kinase Bα or any suitable derivative or fragment thereof or fusion of protein kinase Bα or derivative, or fragment thereof. For example, it is particularly preferred that the protein kinase Bα is a fusion between glutathione-S-transferase and protein kinase Bα as described in Example 1 (GST-PKBα; see also reference 27).

It is preferred that the PKBα is a human PKBα. It should be appreciated that the said 3-phosphoinositide-dependent protein kinase from one species or tissue can phosphorylate and activate PKBα from another species or tissue.

By "activates protein kinase Bα" we include the meaning that upon phosphorylation by the said 3-phosphoinositide-dependent protein kinase the activity of protein kinase Bα to a given substrate increases by at least ten-fold compared to the protein kinase Bα which has not been so phosphorylated, preferably by at least 20-fold and more preferably by at least 30-fold. Suitably, the activity of protein kinase Bα is measured using the synthetic peptide RPRAATF (SEQ ID NO: 9).

By "3-phosphoinositide-dependent protein kinase" we include the meaning that the protein kinase is substantially inactive at activating PKBα in the absence of a suitable 3-phosphoinositide (or a compound that mimics the effect of a 3-phosphoinositide). In particular, the said protein kinase has at least ten-fold increased activity towards protein kinase Bα in the presence of a 3-phosphoinositide compared to the activity in the absence of said 3-phosphoinositide, preferably at least 100-fold, more preferably at least 1000-fold, and still more preferably at least 10,000-fold.

It will be appreciated that the 3-phosphoinositide-dependent protein kinase may be activated by mimics of 3-phosphoinositide as described in more detail below.

Preferably, the activation of PKBα by the 3-phosphoinositide-dependent protein kinase is substantially accelerated by the D-enantiomer of sn-1-stearoyl-2-arachidonyl phosphatidylinositol 3,4,5-trisphosphate but is not substantially accelerated by the L-enantiomer of the said phosphatidylinositol 3,4,5-trisphosphate.

Preferably, the 3-phosphoinositide-dependent protein kinase is substantially activated by the D-enantiomer of sn-1,2-dipalmitoyl phosphatidylinositol 3,4,5-trisphosphate or sn-1,2-dipalmitoyl phosphatidylinositol 3,4-bisphosphate but is not substantially activated by the L-enantiomers of the said phosphatidylinositol phosphates.

Preferably, the 3-phosphinositide-dependent protein kinase is not substantially activated by phosphatidylinositol 3,5-bisphosphate or phosphatidylinositol 4,5-bisphosphate or phosphatidylinositol 3-phosphate or inositol 1,3,4,5-tetrakisphosphate.

Figure 6:
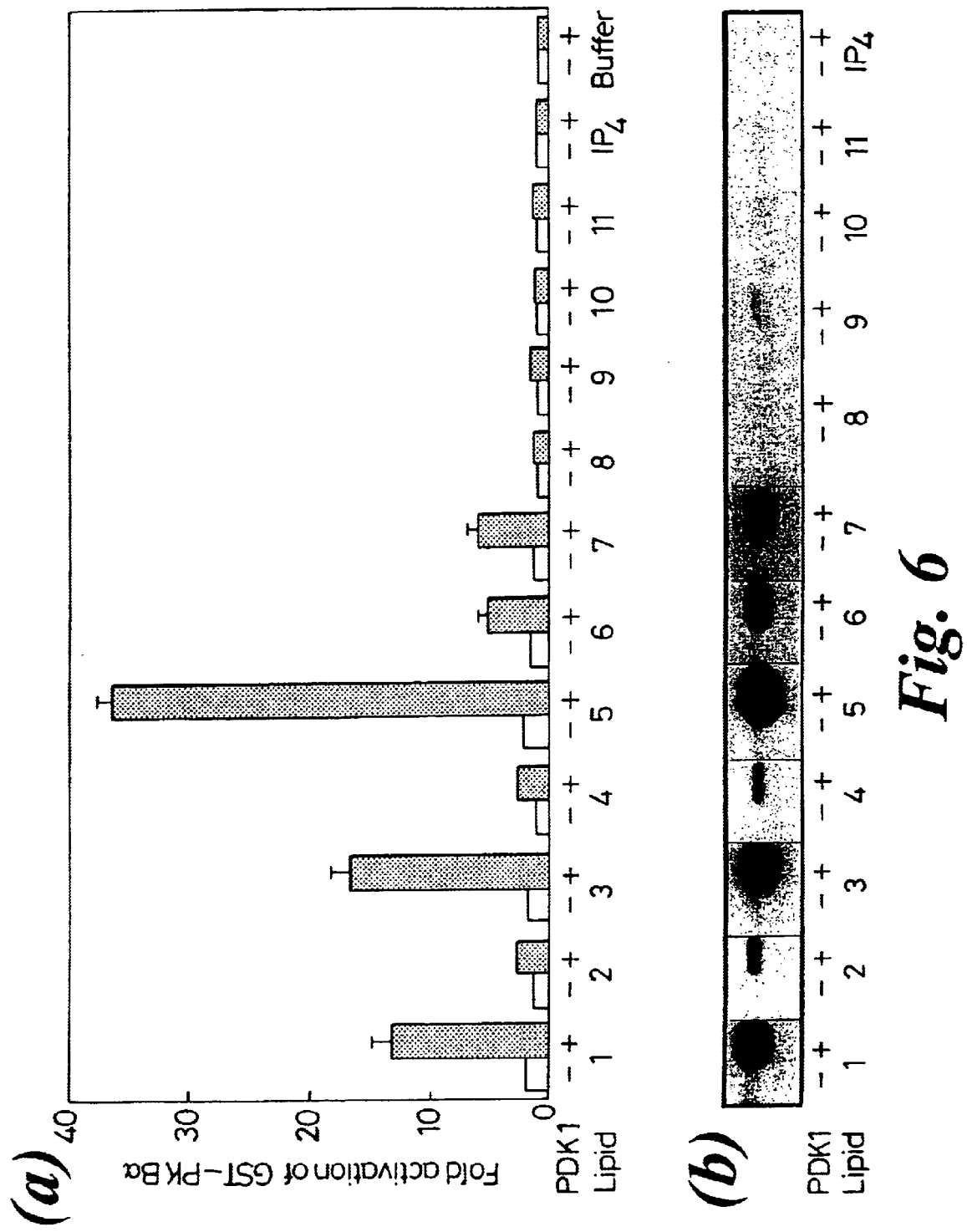

Thus, particularly with reference to FIG. 6 and the rabbit skeletal muscle PDK1 of Example 1, the following 3-phosphoinositides have been found to activate the said 3-phosphoinositide-dependent kinase (in order of level of activation; most effective first):

1. Lipid 5: Racemic sn-1,2-dilinoleoyl PtdIns(3,4,5)P$_3$.
2. (Equal) Lipid 2: D-enantiomer of sn-1-stearoyl-2-arachidonyl PtdIns(3,4,5)P$_3$.
2. (Equal) Lipid 3: D-enantiomer of sn-2-arachidonyl-3-stearoyl PtdIns(3,4,5)P$_3$.
4. (Equal) Lipid 6: sn-1,2 di-palmitoyl PtdIns(3,4,5)P$_3$.
4. Equal Lipid 7: sn-1,2 di-palmitoyl PtdIns(3,4)P$_2$.

The following phospholipids cause no significant activation, at least in relation to rabbit skeletal muscle PDK1:

6. Lipid 2: L-enantiomer of sn-1-stearoyl-2-arachidonyl PtdIns(3,4,5)P$_3$.
7. Lipid 4: L-enantiomer of sn-2-arachidonyl-3-stearoyl PtdIns(3,4,5)P$_3$.
8. Lipid 9: PtdIns(4,5)P$_2$.
9. Lipid 8: sn-1,2 di-palmitoyl PtdIns(3,5)P$_2$.
10. Lipid 11: sn-1,2 di-palmitoyl PtdIns-3P.
11. Lipid 10: PtdIns 4P.
12. IP$_4$: Ins(1,3,4,5P$_4$.

We have found that the human PDK1 enzyme has substantially the same lipid preference as described above.

It is preferred if the 3-phosphoinositide-dependent protein kinase is substantially unaffected by wortmannin.

It should be appreciated that the said 3-phosphoinositide-dependent protein kinase that phosphorylate and activates protein kinase Bα is likely to phosphorylate and activate other forms of protein kinase B such as protein kinase Bβ and protein kinase Bγ. We have shown that PDK1 phosphorylates and activates not only PKBα but also PKBβ and PKBγ. A protein kinase Bβ is described in reference 7. A protein kinase Bγ is described in Konishi et al (1995) Biochem. Biophys. Res. Comm. 216, 526–534.

The 3-phosphoinositide-dependent protein kinase that phosphorylates and activates protein kinase Bα may be isolated from any convenient tissue and from any mammal as described below. It is believed that isoforms of the enzyme exist in different tissues within the same mammal and that the invention encompasses said isoforms and said 3-phosphoinositide-dependent protein kinases from any mammal. It is preferred that the said 3-phosphoinositide-dependent protein kinase is the human said enzyme. It is also preferred if it is the rabbit said enzyme.

It is preferred if the said 3-phosphoinositide-dependent protein kinase is about 67 kDa as determined by sodium dodecyl sulphate polyacrylamide gel electrophoresis (SDS-PAGE).

A particularly preferred embodiment is a substantially pure 3-phosphoinositide-dependent protein kinase that phosphorylates and activates protein kinase Bα the 3-phosphoinositide-dependent protein kinase comprising the amino acid sequences ANSFVGTAQYVSPELL (SEQ ID NO: 3) or AGNEYLIFQK (SEQ ID NO: 4) or LDH-PFFVK (SEQ ID NO: 5) or two or more of these sequences or amino sequences with from 1 to 4 conservative substitutions thereof. What is meant by "conservative substitutions" is described below.

A particular preferred embodiment is a polypeptide which comprises the amino acid sequence (SEQ ID NO: 1).

```
MARTTSQLYDAVPIQSSVVLCSCPSPSMVRTQTESSTPPGIPGGSRQGPAMDGTAAEPRPGAGS

LQHAQPPPQPRKKRPEDFKFGKILGEGSFSTVVLARELATSREYAIKILEKRHIIKENKVPYVT

RERDVMSRLDHPFFVKLYFTFQDDEKLYFGLSYAKNGELLKYIRKIGSFDETCTRFYTAEIVSA

LEYLHGKGIIHRDLKPENILLNEDMHIQITDFGTAKVLSPESKQARANSFVGTAQYVSPELLTE

KSACKSSDLWALGCIIYQLVAGLPPFRAGNEYLIFQKIIKLEYDFPEKFFPKARDLVEKLLVLD

ATKRLGCEEMEGYGPLKAHPFFESVTWENLHQQTPPKLTAYLPAMSEDDEDCYGNYDNLLSQFG

CMQVSSSSSSHSLSASDTGLPQRSGSNIEQYIHDLDSNSFELDLQFSEDEKRLLLEKQAGGNPW

HQFVENNLILKMGPVDKRKGLFARRRQLLLTEGPHLYYVDPVNKVLKGEIPWSQELRPEAKNFK

TFFVHTPNRTYYLMDPSGNAHKWCRKIQEVWRQRYQSHPDAAVQ
``` or a variant, fragment, derivative or fusion thereof. The amino acid sequence is that of human PDK1 as determined from the nucleotide sequence of cDNAs encoding human PDK1.

The deduced amino acid sequence is also given in FIG. 10.

As is discussed in more detail in the Examples, at least in relation to human PDK1, experiments in which the pleckstrin homology (PH) domains (which have been found to be present in human PDK1 and which are known to be present in PKBα and are believed to be involved in binding phospholipids) of either PDK1 or PKBα were deleted indicated that the binding of PtdIns(3,4,5)P3 or PtdIns(3,4)P2 to PKBα is required for phosphorylation and activation by PDK1. A GST-PKBα mutant lacking the PH domain possesses a 3-fold higher activity than that of full length wild-type GST-PKBα and was activated and phosphorylated by PDK1 in a PtdIns(3,4,5)P3 independent manner; however, the rate of activation was reduced about 20-fold compared to wild-type GST-PKBα. A mutant PDK1 lacking the putative C-terminal PH domain, expressed as a GST-fusion protein, is still able to activate GST-PKBα in a PtdIns(3,4,5)P3-dependent manner, but the rate of activation was reduced about 30-fold compared to full length GST-PDK1. The effect of PtdIns(3,4,5)P3/PtdIns(3,4)P2 in the activation of PKBα by PDK1 is, therefore, at least partly substrate directed. However, the drastic reduction in the rate of activation of PKB by PDK1 when the PH domain of PDK1 is deleted indicates the importance of the PH domain of PDK1 and hence the importance of PtdIns(3,4,5)P3/PtdIns(3,4)P2 in the activation of PKB by PDK1. Thus, the substantially pure 3-phosphoinositide dependent protein lipase that phosphorylates and activates protein kinase Bα may be 3-phosphoinositide dependent in the sense that the intact enzyme (for example intact PDK1) requires the presence of a 3-phosphoinositide in order to phosphorylate an intact PKBα in vivo. The protein kinase of the invention phosphorylates and activates PKBα in a 3-phosphoinositide-dependent manner.

PDK1 has been shown by us to phosphorylate p70 S6 kinase in the absence of InsPtd(3,4,5)P$_3$. PDK1 has been shown to bind PtdIns(3,4,5)P3 directly.

A second aspect of the invention provides a recombinant polynucleotide encoding a 3-phosphoinositide-dependent protein kinase that phosphorylates and activates protein kinase Bα provided that the recombinant polynucleotide is not the DNA corresponding to IMAGE clone 526583 or IMAGE clone 626511. The DNA sequence of at least part of the inserts of these clones are given in GenBank Accession No AA121994 and AA186323, respectively. Preferences for the said 3-phosphoinositide-dependent protein kinase are the same as in the first aspect of the invention. The invention also encompasses polynucleotides which encode variants, fragments, derivatives or fusions of said 3-phosphoinositide-dependent protein kinase or fusions of the said variants, fragments or derivatives. The EST AA121994 was derived from pancreas tissue and the EST AA186323 was derived from HeLa cells.

A particular preferred embodiment of the invention is a polynucleotide comprising the nucleotide sequence (SEQ ID NO: 2).

```
ATGGCCAGGACCACCAGCCAGCTGTATGACGCCGTGCCCATCCAGTCCAGCGTGGTGTTA

TGTTCCTGCCCATCCCCATCAATGGTGAGGACCCAGACTGAGTCCAGCACGCCCCTGGC

ATTCCTGGTGGCAGCAGGCAGGGCCCCGCCATGGACGGCACTGCAGCCGAGCCTCGGCCC

GGCGCCGGCTCCCTGCAGCATCCCAGCCTCCGCCGCAGCCTCGGAAGAAGCGGCCTGAGG

ACTTCAAGTTTGGGAAAATCCTTGGGGAAGGCTCTTTTTCCACGGTTGTCCTGGCTCGAG

AACTGGCAACCTCCAGAGAATATGCGATTAAAATTCTGGAGAAGCGACATATCATAAAAG

AGAACAAGGTCCCCTATGTAACCAGAGAGCGGGATGTCATGTCGCGCCTGGATCACCCCT

TCTTTGTTAAGCTTTACTTCACATTTCAGGACGACGAGAAGCTGTATTTCGGCCTTAGTT

ATGCCAAAAATGGAGAACTACTTAAATATATTCGCAAAATCGGTTCATTCGATGAGACCT

GTACCCGATTTTACACGGCTGAGATCGTGTCTGCTTTAGAGTACTTGCACGGCAAGGGCA

TCATTCACAGGGACCTTAAACCGGAAAACATTTTGTTAAATGAAGATATGCACATCCAGA

TCACAGATTTTGGAACAGCAAAAGTCTTATCCCCAGAGAGCAAACAAGCCAGGGCCAACT

CATTCGTGGGAACAGCGCAGTACGTTTCTCCAGAGCTGCTCACGGAGAAGTCCGCCTGTA

AGAGTTCAGACCTTTGGGCTCTTGGATGCATAATATACCAGCTTGTGGCAGGACTCCCAC

CATTCCGAGCTGGAAACGAGTATCTTATATTTCAGAAGATCATTAAGTTGGAATATGACT

TTCCAGAAAAATTCTTCCCTAAGGCAAGAGACCTCGTGGAGAAACTTTTGGTTTTAGATG

CCACAAAGCGGTTAGGCTGTGAGGAAATGGAAGGATACGGACCTCTTAAAGCACACCCGT

TCTTCGAGTCCGTCACGTGGGAGAACCTGCACCAGCAGACGCCTCCGAAGCTCACCGCTT

ACCTGCCGGCTATGTCGGAAGACGACGAGGACTGCTATGGCAATTATGACAATCTCCTGA

GCCAGTTTGGCTGCATGCAGGTGTCTTCGTCCTCCTCCTCACACTCCCTGTCAGCCTCCG

ACACGGGCCTGCCCCAGAGGTCAGGCAGCAACATAGAGCAGTACATTCACGATCTGGACT

CGAACTCCTTTGAACTGGACTTACAGTTTTCCGAAGATGAGAAGAGGTTGTTGTTGGAGA

AGCAGGCTGGCGGAAACCCTTGGCACCAGTTTGTAGAAAATAATTTAATACTAAAGATGG

GCCCAGTGGATAAGCGGAAGGGTTTATTTGCAAGACGACGACAGCTGTTGCTCACAGAAG

GACCACATTTATATTATGTGGATCCTGTCAACAAAGTTCTGAAAGGTGAAATTCCTTGGT

CACAAGAACTTCGACCAGAGGCCAAGAATTTTAAAACTTTCTTTGTCCACACGCCTAACA

GGACGTATTATCTGATGGACCCCAGCGGGAACGCACACAAGTGGTGCAGGAAGATCCAGG

AGGTTTGGAGGCAGCGATACCAGAGCCACCCGGACGCCGCTGTGCAGTGA
``` or variants or variations thereof. The given nucleotide sequence is that containing a coding sequence which encodes human PDK1.

The cDNA sequence is also given in FIG. 10.

IMAGE clones 526583 and 626511 are known in the art and are publicly available from HGMP Resource Centre, I.M.A.G.E. Consortium, Hinxton, Cambridge CB1 1SB, UK. The clones are partial length cDNAs inserted into pBluescript SK–. It was not known that these clones were derived from a mRNA encoding a protein kinase.

Certain other ESTs are publicly available which encode parts of the PDK1 cDNA namely H97903 (melanocyte), AA018098 (retina), AA18097 (retina), AA019394 (retina), AA019393 (retina, N22904 (melanocyte), W94736 (fetal heart), EST 51985 (gall bladder), N31292 (melanocyte), AA188174 (HeLa cells), AA100210 (colon) and R84271

(retina). The polynucleotides corresponding to these ESTs are not claimed per se but they may be useful in carrying out certain parts of the invention. It had not been shown that these clones were derived from a mRNA encoding a protein ase.

The invention also includes a polynucleotide comprising a fragment of the recombinant polynucleotide of the second aspect of the invention. Preferably, the polynucleotide comprises a fragment which is at least 10 nucleotides in length, more preferably at least 14 nucleotides in length and still more preferably at least 18 nucleotides in length. Such polynucleotides are useful as PCR primers.

The polynucleotide or recombinant polynucleotide may be DNA or RNA, preferably DNA. The polynucleotide may or may not contain introns in the coding sequence; preferably the polynucleotide is a cDNA.

A "variation" of the polynucleotide includes one which is (i) usable to produce a protein or a fragment thereof which is in turn usable to prepare antibodies which specifically bind to the protein encoded by the said polynucleotide or (ii) an antisense sequence corresponding to the gene or to a variation of type (i) as just defined. For example, different codons can be substituted which code for the same amino acid(s) as the original codons. Alternatively, the substitute codons may code for a different amino acid that will not affect the activity or immunogenicity of the protein or which may improve or otherwise modulate its activity or immunogenicity. For example, site-directed mutagenesis or other techniques can be employed to create single or multiple mutations, such as replacements, insertions, deletions, and transpositions, as described in Botstein and Shortle, "Strategies and Applications of In Vitro Mutagenesis," *Science*, 229: 193–210 (1985), which is incorporated herein by reference. Since such modified polynucleotides can be obtained by the application of known techniques to the teachings contained herein, such modified polynucleotides are within the scope of the claimed invention.

Moreover, it will be recognised by those skilled in the art that the polynucleotide sequence (or fragments thereof) of the invention can be used to obtain other polynucleotide sequences that hybridise with it under conditions of high stringency. Such polynucleotides includes any genomic DNA. Accordingly, the polynucleotide of the invention includes polynucleotide that shows at least 55 per cent, preferably 60 per cent, and more preferably at least 70 per cent and most preferably at least 90 per cent homology with the polynucleotide identified in the method of the invention, provided that such homologous polynucleotide encodes a polypeptide which is usable in at least some of the methods described below or is otherwise useful.

Per cent homology can be determined by, for example, the GAP program of the University of Wisconsin Genetic Computer Group.

DNA-DNA, DNA-RNA and RNA-RNA hybridisation may be performed in aqueous solution containing between 0.1×SSC and 6×SSC and at temperatures of between 55° C. and 70° C. It is well known in the art that the higher the temperature or the lower the SSC concentration the more stringent the hybridisation conditions. By "high stringency" we mean 2×SSC and 65° C. 1×SSC is 0.15M NaCl/0.015M sodium citrate. Polynucleotides which hybridise at high stringency are included within the scope of the claimed invention.

"Variations" of the polynucleotide also include polynucleotide in which relatively short stretches (for example 20 to 50 nucleotides) have a high degree of homology (at least 80% and preferably at least 90 or 95%) with equivalent stretches of the polynucleotide of the invention even though the overall homology between the two polynucleotides may be much less. This is because important active or binding sites may be shared even when the general architecture of the protein is different.

By "variants" of the polypeptide we include insertions, deletions and substitutions, either conservative or non-conservative, where such changes do not substantially alter the activity of the said 3-phosphoinositide-dependent protein kinase.

By "conservative substitutions" is intended combinations such as Gly, Ala; Val, Ile, Leu; Asp, Glu; Asn, Gln; Ser, Thr; Lys, Arg; and Phe, Tyr.

Such variants may be made using the methods of protein engineering and site-directed mutagenesis well known in the art.

Preferably, the variant or variation of the polynucleotide encodes a 3-phosphoinositide-dependent protein kinase that has at least 30%, preferably at least 50% and more preferably at least 70% of the activity towards protein kinase Bα of a natural said 3-phosphoinositide-dependent protein kinase, under the same assay conditions.

By "fragment of said 3-phosphoinositide-dependent protein kinase" we include any fragment which retains activity or which is useful in some other way, for example, for use in raising antibodies or in a binding assay.

By "fusion of said 3-phosphoinositide-dependent protein kinase" we include said protein kinase fused to any other polypeptide. For example, the said protein kinase may be fused to a polypeptide such as glutathione-S-transferase (GST) or protein A in order to facilitate purification of said protein kinase. Fusions to any variant, fragment or derivative of said protein kinase are also included in the scope of the invention.

A further aspect of the invention provides a replicable vector comprising a recombinant polynucleotide encoding a 3-phosphoinositide-dependent protein kinase that phosphorylates and activates protein kinase Bα, or a variant, fragment, derivative or fusion of said protein kinase or a fusion of said variant, fragment or derivative.

A variety of methods have been developed to operably link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3-single-stranded termini with their 3'–5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) *Science* 239, 487–491. This method may be used for introducing the DNA into a suitable vector, for example by engineering in suitable restriction sites, or it may be used to modify the DNA in other useful ways as is known in the art.

In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

The DNA (or in the case of retroviral vectors, RNA) is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. No. 4,440,859 issued Apr. 3, 1984 to Rutter et al, U.S. Pat. No. 4,530,901 issued Jul. 23, 1985 to Weissman, U.S. Pat. No. 4,582,800 issued Apr. 15, 1986 to Crowl, U.S. Pat. No. 4,677,063 issued Jun. 30, 1987 to Mark et al, U.S. Pat. No. 4,678,751 issued Jul. 7, 1987 to Goeddel, U.S. Pat. No. 4,704,362 issued Nov. 3, 1987 to Itakura et al, U.S. Pat. No. 4,710,463 issued Dec. 1, 1987 to Murray, U.S. Pat. No. 4,757,006 issued Jul. 12, 1988 to Toole, Jr. et al, U.S. Pat. No. 4,766,075 issued Aug. 23, 1988 to Goeddel et al and U.S. Pat. No. 4,810,648 issued Mar. 7, 1989 to Stalker, all of which are incorporated herein by reference.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example Aspergillus), plant cells, animal cells and insect cells.

The vectors include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403406 and pRS413416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413416 are Yeast Centromere plasmids (YCps).

The present invention also relates to a host cell transformed with a polynucleotide vector construct of the present invention. The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and kidney cell lines. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors.

Transformation of appropriate cell hosts with a DNA construct of the present invention is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et al (1989) *Molecular Cloning, A Laboratory Manual*, Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104–109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming and/or transfecting cells and is well known in the art for transforming yeast cell, bacterial cells, insect cells and vertebrate cells.

For example, many bacterial species may be transformed by the methods described in Luchansky et al (1988) *Mol. Microbiol.* 2, 637–646 incorporated herein by reference. The greatest number of transformants is consistently recovered following electroporation of the DNA-cell mixture suspended in 2.5×PEB using 6250V per cm at 25 $\mu$FD.

Methods for transformation of yeast by electroporation are disclosed in Becker & Guarente (1990) *Methods Enzymol.* 194, 182.

Successfully transformed cells, ie cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium.

A further aspect of the invention provides a method of making a 3-phosphoinositide-dependent protein kinase that phosphorylates and activates protein kinase B$\alpha$ or a variant, derivative, fragment or fusion thereof or a fusion of a variant, fragment or derivative the method comprising culturing a host cell comprising a recombinant polynucleotide or a replicable vector which encodes said 3-phosphoinositide-dependent protein kinase, and isolating said protein kinase or a variant, derivative, fragment or fusion thereof of a fusion of a variant, fragment or derivative from said host cell. Methods of cultivating host cells and isolating recombinant proteins are well known in the art.

A still further aspect of the invention provides a method of isolating a 3-phosphoinositide-dependent protein kinase that phosphorylates and activates protein kinase B$\alpha$ the method comprising the steps of (a) obtaining tissue from a mammal that contains said 3-phosphoinositide-dependent kinase, (b) obtaining a cell-free extract from said tissue, (c) fractionating said cell-free extract and (d) selecting a fraction from step (c) which is capable of phosphorylating and activating protein kinase B$\alpha$ in the presence of a 3-phosphoinositide.

Preferably, the 3-phosphoinositide is any of the preferred 3-phosphoinositides as disclosed in relation to the first aspect of the invention; most preferably it is phosphatidylinositol-3,4,5-trisphosphate or phosphatidylinositol-3,4-bisphosphate. Preferably, further steps are employed. Conveniently, in a step (e) the fraction of step (d) is fractionated further and in a step (f) a fraction is selected from step (e) which is capable of phosphorylating and activating protein kinase B$\alpha$ in the presence of a 3-phosphoinositide. Steps (e) and (f) may be repeated until a substantially pure preparation of a 3-phosphoinositide-dependent protein kinase that phosphorylates and activates protein kinase B$\alpha$ is obtained. Suitably, the fractionation steps include any of ion exchange chromatography, polyethylene glycol (PEG) precipitation, heparin chromatography or any other fractionation procedures. Preferably, the method steps are those substantially as described in Example 1.

Conveniently, the tissue is skeletal muscle. The tissue may be from any mammal including humans.

A further aspect of the invention provides a phosphoinositide-dependent protein kinase which can phosphorylate and activate protein kinase B$\alpha$, or a variant, fragment, derivative or fusion thereof or a fusion of a variant, fragment or derivative obtainable by the methods herein disclosed.

A still further aspect of the invention provides an antibody reactive towards a phosphoinositide-dependent protein kinase of the invention.

Antibodies reactive towards the said phosphoinositide-dependent protein kinase of the invention may be made by methods well known in the art. In particular, the antibodies may be polyclonal or monoclonal.

Suitable monoclonal antibodies which are reactive towards the said protein kinase may be prepared by known techniques, for example those disclosed in *"Monoclonal Antibodies: A manual of techniques"*, H Zola (CRC Press, 1988) and in "Monoclonal Hybridoma Antibodies: Techniques and Applications", SGR Hurrell (CRC Press, 1982).

In a preferred embodiment the antibody is raised using any one of the peptide sequences ANSFVGTAQYVSPELL (SEQ. ID NO: 3) or AGNEYLIFQK (SEQ. ID NO: 4) or LDHPFFVK (SEQ. ID NO: 5). It is preferred if polyclonal antipeptide antibodies are made. Other peptides may be used to make antibodies for example the peptides RQRYQSHP-DAAVQ (SEQ. ID NO: 6) and LSPESKQARANS (SEQ. ID NO: 7). Peptides in which one or more of the amino acid residues are chemically modified, before or after the peptide is synthesised, may be used providing that the function of the peptide, namely the production of specific antibodies in vivo, remains substantially unchanged. Such modifications include forming salts with acids or bases, especially physiologically acceptable organic or inorganic acids and bases, forming an ester or amide of a terminal carboxyl group, and attaching amino acid protecting groups such as N-t-butoxycarbonyl. Such modifications may protect the peptide from in vivo metabolism. The peptides may be present as single copies or as multiples, for example tandem repeats. Such tandem or multiple repeats may be sufficiently antigenic themselves to obviate the use of a carrier. It may be advantageous for the peptide to be formed as a loop, with the N-terminal and C-terminal ends joined together, or to add one-or more Cys residues to an end to increase antigenicity and/or to allow disulphide bonds to be formed. If the peptide is covalently linked to a carrier, preferably a polypeptide, then the arrangement is preferably such that the peptide of the invention forms a loop.

According to current immunological theories, a carrier function should be present in any immunogenic formulation in order to stimulate, or enhance stimulation of, the immune system. It is thought that the best carriers embody (or, together with the antigen, create) a T-cell epitope. The peptides may be associated, for example by cross-linking, with a separate carrier, such as serum albumins, myoglobins, bacterial toxoids and keyhole limpet haemocyanin. More recently developed carriers which induce T-cell help in the immune response include the hepatitis-B core antigen (also called the nucleocapsid protein), presumed T-cell epitopes such as Thr-Ala-Ser-Gly-Val-Ala-Glu-Thr-Thr-Asn-Cys, (SEQ ID NO: 8)beta-galactosidase and the 163–171 peptide of interleukin-1. The latter compound may variously be regarded as a carrier or as an adjuvant or as both. Alternatively, several copies of the same or different peptides of the invention may be cross-linked to one another; in this situation there is no separate carrier as such, but a carrier function may be provided by such cross-linking. Suitable cross-linking agents include those listed as such in the Sigma and Pierce catalogues, for example glutaraldehyde, carbodiimide and succinimidyl 4(N-maleimidomethyl) cyclohexane-1-carboxylate, the latter agent exploiting the -SH group on the C-terminal cysteine residue (if present).

If the peptide is prepared by expression of a suitable nucleotide sequence in a suitable host, then it may be advantageous to express the peptide as a fusion product with a peptide sequence which acts as a carrier. Kabigen's "Ecosec" system is an example of such an arrangement.

The peptide of the invention may be linked to other antigens to provide a dual effect.

Peptides may be synthesised by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversedN, N-dicyclohexyl-carbodiimide/1-hydroxybenzotriazolemediated coupling procedure. All coupling and deprotection reactions are monitored using ninhydrin, tinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally vailable from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

A further aspect of the invention provides a method of identifying a compound that modulates the activity of a 3-phosphoinositide-dependent protein kinase that phosphorylates and activates protein kinase Bα, the method comprising contacting a compound with the said 3-phosphoinositide-dependent protein kinase or a variant, fragment, derivative or fusion thereof or a fusion of a variant, fragment or derivative thereof and determining whether, in the presence of said compound, phosphorylation and activation of a protein kinase B or phosphorylation a suitable substrate of the 3-phosphoinositide-dependent protein kinase is changed compared to the activity of said 3-phosphoinositide-dependent protein kinase or said variant, fragment, derivative or fusion thereof or a fusion of a variant, fragment or derivative thereof in the absence of said compound.

We believe that the said 3-phosphoinositide-dependent protein kinase of the invention is able to phosphorylate not only protein kinase Bα but also other forms of protein kinase B such as protein kinase Bβ and protein kinase Bγ. We have shown that PDK1 is able to phosphorylate PKBα, PKBβ and PKBγ. Thus, in this method and the methods described below the protein kinase B can be any protein kinase B such as protein kinase Bα or protein kinase Bβ or protein kinase Bγ. Other substrates of the 3-phosphoinositide-dependent protein kinase may be used in the assay method of the invention, for example p70 S6 kinase. A suitable phospholipid such as PtdIns(3,4,5)P3 is typically present in the screen when a PKB containing a PH domain is used as a substrate but it is not necessary for a 3-phosphoinositide to be present in some circumstances, for example when p70 S6 kinase, or PKB lacking a PH domain, is used as a substrate. Phosphorylation of p70 S6 kinase occurs in the absence of PtdIns(3,4,5)P$_3$.

It will be appreciated that the method can be carried out in vitro using 3-phosphoinositide-dependent protein kinase or a variant, fragment, derivative or fusion thereof or a fusion of a variant, fragment or derivative in the presence of a suitable protein kinase B or other suitable substrate. But it will also be appreciated that it may be carried out in vivo, for example using the yeast two-hybrid system to detect compounds which reduce or enhance the interactions between the phosphoinositide-dependent protein kinase and PKB or another suitable substrate.

In one embodiment the compound decreases the activity of the 3-phosphoinositide-dependent protein kinase.

In another embodiment the compound increases the activity of the 3-phosphoinositide-dependent protein kinase. Preferably the compound competes with 3-phosphoinositide. Preferably, the compound substantially reduces activation by phosphatidylinositol-3,4,5- trisphosphate or phosphatidyl-inositol-3,4-bisphosphate. Preferably, the compound substantially enhances activation by phosphatidylinositol-3,4,5-trisphosphate or phosphatidylinositol-3,4-bisphosphate. It will be appreciated that the method may be used to identify compounds which bind to and effect the activity of either the said 3-phosphoinositide-dependent protein kinase or the protein kinase B when protein kinase B is present in the assay.

A still further aspect of the invention provides a method of identifying a compound that mimics the effect of a 3-phosphoinositide on a 3-phosphoinositide-dependent protein kinase that phosphorylates and activates protein kinase Bα, the method comprising determining whether said compound activates a said 3-phosphoinositide-dependent protein kinase or a suitable variant, fragment, derivative or fusion thereof or a fusion of a variant, fragment or derivative so that it can phosphorylate and activate protein kinase Bα or phosphorylate any other suitable substrate, the activation by said compound being in the absence of a 3-phosphoinositide.

The activity of protein kinase B can be measured using any suitable substrate; for example, the peptide RPRAATF (SEQ. ID NO: 9) is a preferred substrate but, for example, myelin basic protein and certain histones are also substrates of PKB.

Preferably, the 3-phosphoinositide is phosphatidylinositol-3,4,5-trisphosphate or phosphatidylinositol-3,4-bisphosphate.

We believe that PtdIns(3,4,5)P3 or a suitable phosphoinositide interacts with the PH domain of a PKB in order for PDK1 to phosphorylate Thr-308 of PKBα and activate this protein kinase. Our data suggests that a PKB molecule lacking the PH domain is activated and phosphorylated independently of PtdIns(3,4,5)P3. There are several mechanisms by which a drug (which interferes with the interaction between the kinase of the invention, for example, PDK1 and PKB) may act. In one mechanism it may bind to PKB and prevent PKB from becoming activated by the kinase of the invention, for example PDK1. In the other mechanism, the drug may bind to the kinase of the invention (such as PDK1) and inhibit PDK1 activity. In a further mechanism the drug may bind to PDK1 and prevent it activating PKB. It is preferred if the screening assays of the invention are carried out using both a full-length PKB molecule (for example a GST-PKB fusion) or a molecule which, although not full length, retains a PH domain which is substantially capable of binding a suitable phospholipid such as PtdIns(3,4,5)P3, and a PKB in which the PH domain has been modified so that the PKB is substantially incapable of binding a suitable phospholipid such as PtdIns(3,4,5)P3. Suitable modifications include deletion of all or part of the PH domain or mutations in the PH domain which substantially prevent binding of the suitable phospholipid. Compounds which prevent PtdIns(3,4,5)P3 from interacting with PKB are particularly selected, which can be detected in the screen.

Alternatively, it may be useful to use PKB lacking a functional PH domain in a screening assay of the invention, in this case no 3-phosphoinositide need be used in order for PDK1 to activate PKB.

A further aspect of the invention provides a compound identifiable by the screening methods disclosed herein.

The methods effectively are screening assays for compounds which modulate the said 3-phosphoinositide-dependent protein kinase or its interactions with a 3-phosphoinositide or with a protein kinase B.

Thus, the screening methods of the invention include methods for identifying compounds which compete with the 3-phosphoinositide (in particular phosphatidylinositol-3,4,5-trisphosphate or phosphatidylinositol-3,4-bisphosphate) and which lead to inactivation or activation of the said 3-phosphoinositide-dependent protein kinase or other modulation of the enzyme activity; they also include screening methods for substances which bind to the said 3-phosphoinositide-dependent protein kinase and which reduce or enhance the activation of a protein kinase B or another suitable substrate (for example, they may bind to said 3-phosphoinositide-dependent protein kinase and prevent it interacting with a protein kinase B); and they also include screening methods for substances which bind to a protein kinase B and which reduce or enhance its interaction with said 3-phosphoinositide-dependent protein kinase. The screening methods of the invention also include methods for identifying compounds which block the catalytic sites of PKB and the protein kinase of the invention (for example, PDK1). Methods for carrying out this type of screening assay are well known in the art.

It will be appreciated that in those assays where a said 3-phosphoinositide-dependent protein kinase is required and the phosphorylation of a particular substrate requires the presence of a 3-phosphoinositide, a 3-phosphoinositide is present. Any suitable 3-phosphoinositide is useful but it is preferred if the 3-phosphoinositide is phosphatidylinositol-3,4,5-trisphosphate or phosphatidylinositol-3,4-bisphosphate. However, as is clear from the foregoing, some assay systems do not require the presence of a 3-phosphoinositide such as PtdIns(3,4,5)P3.

The compounds identified in the methods may themselves be useful as drug or they may represent lead compounds for the design and synthesis of more efficacious compounds which modulate the activity of the said 3-phosphoinositide-dependent protein kinase or its interactions with a 3-phosphoinositide or with a protein kinase B.

Thus, a further aspect of the invention provides a method of modulating in a cell the activity of the said 3-phosphoinositide-dependent protein kinase or its interactions with a 3-phosphoinositide or with a protein kinase B, the method comprising introducing into the cell a compound identifiable in the screening assay described above. Preferably, the cell is in a human patient. Compounds, identifiable in the screening method, which mimic the effect of a 3-phosphoinositide, preferably phosphoinositol-3,4,5-trisphosphate or phosphoinositol-3,4-bisphosphate, are believed to be useful in treating diabetes. Compounds identifiable in the screening methods of the invention that inhibit PKB, PDK1 or the activation of PKB by PDK1 are believed to be useful in treating cancer. PKB is the cellular homologue of v-akt which is involved in leukaemias. Two isoforms of PKB are overexpressed in ovarian, pancratic and breast cancers. It is believed that PKB mediates protection of cells to apoptosis mediated, for example, by IGF-1. Overexpression of PKB may allow cancer cells to proliferate by stopping apoptosis.

It will be appreciated that certain compounds found in the screening methods may be able to enhance cell proliferation in a beneficial way and may be useful, for example in the regeneration of nerves or in wound healing.

Further aspects of the invention provide the use of said 3-phosphoinositide-dependent protein kinase or variants, fragments, derivatives or fusions thereof or fusions of said variants, fragments or derivatives in a screening assay for compounds which modulate the activity of said protein kinase, in particular its interaction with 3-phosphoinositide or a protein kinase B. The invention also includes the use of the said 3-phosphoinositide-dependent protein kinase, such as PDK1, to phosphorylate and active protein kinase B and it includes a method of activating PKB using a 3-phosphoinositide-dependent protein, such as PDK1.

A still further aspect of the invention provides kits of parts that are useful in carrying out the screening methods. Conveniently, the kit of parts comprises a said 3-phosphoinositide-dependent protein kinase or a suitable variant or fragment or derivative or fusion thereof or a fusion of a variant or fragment or derivative (or a polynucleotide which encodes any of these) and a protein kinase B or a suitable variant or fragment or derivative or fusion thereof or a fusion of a variant or fragment or derivative (or a polynucleotide which encodes any of these). It will be appreciated that, depending on the screening method employed, it may additionally comprise a suitable 3-phosphoinositide or a suitable substrate for the protein kinase B.

Abbreviations: PKB, Protein kinase B; PtdIns(3,4,5)P3, Phosphatidylinositol 3,4,5-tris phosphate; PtdIns(3,4,)P2, Phosphatidylinositol 3,4-bisphosphate; PI 3-kinase, Phosphoinositide 3-kinase; PtdCho, Phosphatidylcholine; PtdSer, Phosphatidylserine; PH, pleckstrin homology.

The invention will now be described in more detail with reference to the following Examples and Figures wherein FIG. 1. SDS Polyacrylamide gel of purified GST-PKBα. 293 cells were transiently transfected with the pEBG2T DNA construct expressing GST-PKBα, serum starved for 16 h and, aftcell lysis, GST-PKBα purified by affinity chromatography on glutathione-SEPHAROSE™ Methods). "Sepharose" is a trade mark. The glutathione-SEPHAROSE™ eluate (3 μg protein) was electrophoresed on a 10% SDS polyacrylamide gel and stained with COOMASSIE™ blue. COOMASSIE™ is a trade mark. The position of the molecular mass markers, glycogen phosphorylase (97 kDa), bovine serum albumin (67 kDa) and ovalbumin (43 kDa) are indicated.

Figure 2:
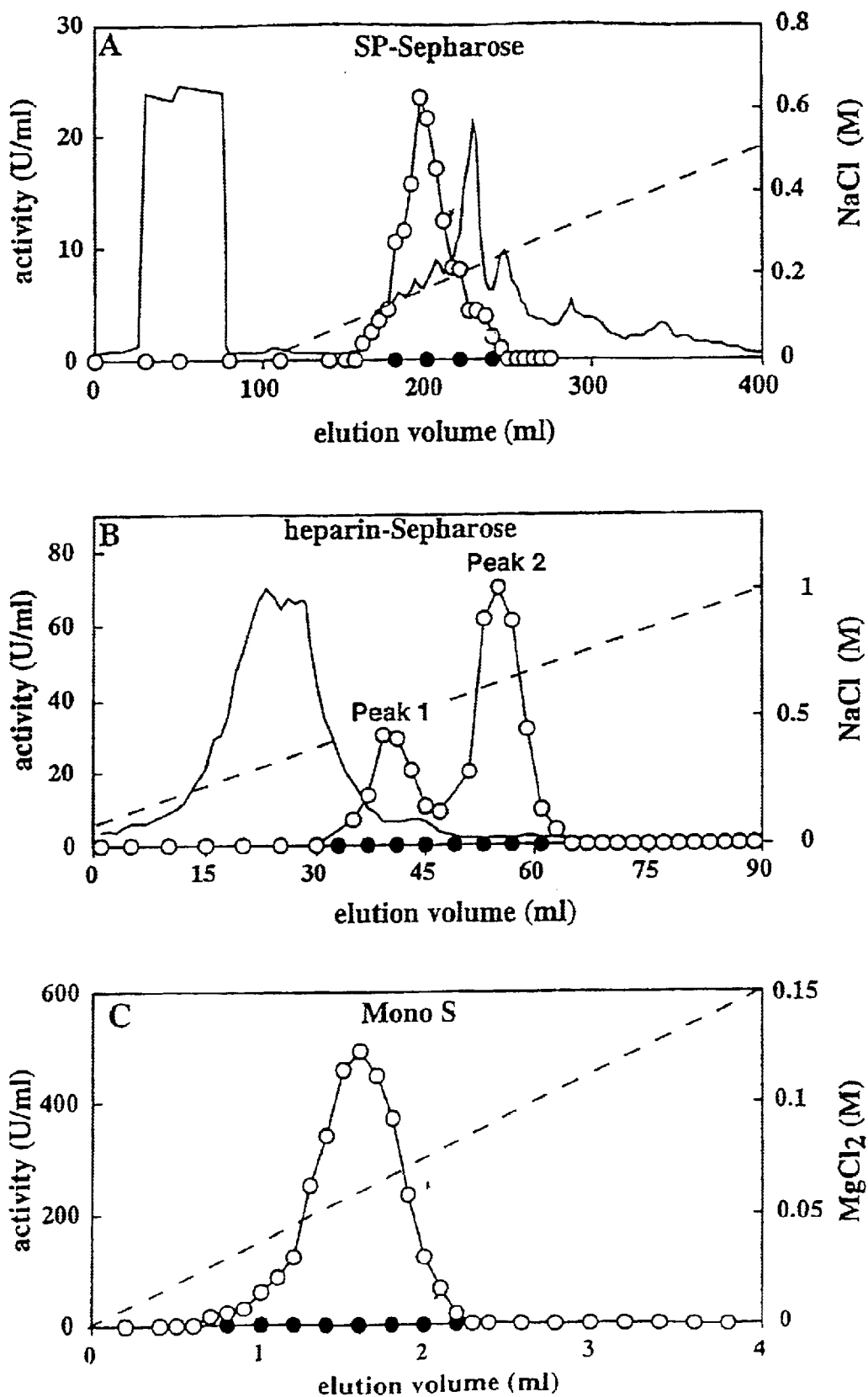

FIG. 2. Identification and purification of a PtdIns(3,4,5)P3 dependent protein kinase (PDK1) which activates GST-PKBα. Following the PEG precipitation PDK1 was chromatographed sequentially on SP-Sepharose (A) and heparin-Sepharose (B) and Peak 2 from the latter column was chromatographed on MONO S™ (C) (see Methods). "Mono S" is a trade mark. PDK1 activity was assayed either in the presence of phospholipid vesicles comprising 100 μM PtdCho, 100 μM PtdSer, 10 μM D-enantiomer ofsn-1-stearoyl 2-arachidonyl PtdIns(3,4,5)P3 (open circles) or vesicles comprising only 100 μM PtdCho and 100 μM PtdSer (closed circles). The broken lines indicate the salt gradient and the solid line the absorbance at 280 nm. The amount of protein eluted from the Mono S column was too low see any absorbance at 280 nm.

Figure 3A:
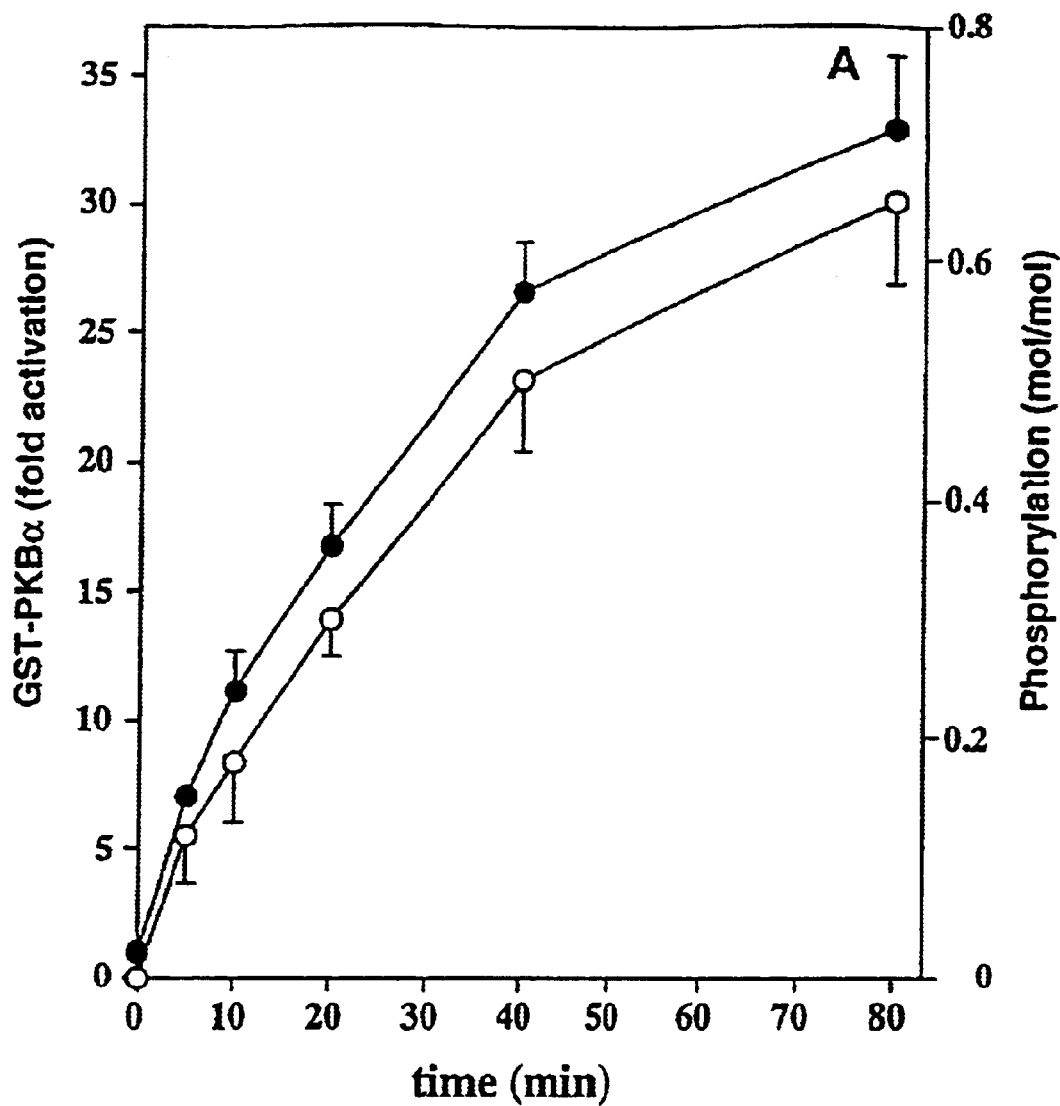
Figure 3B:
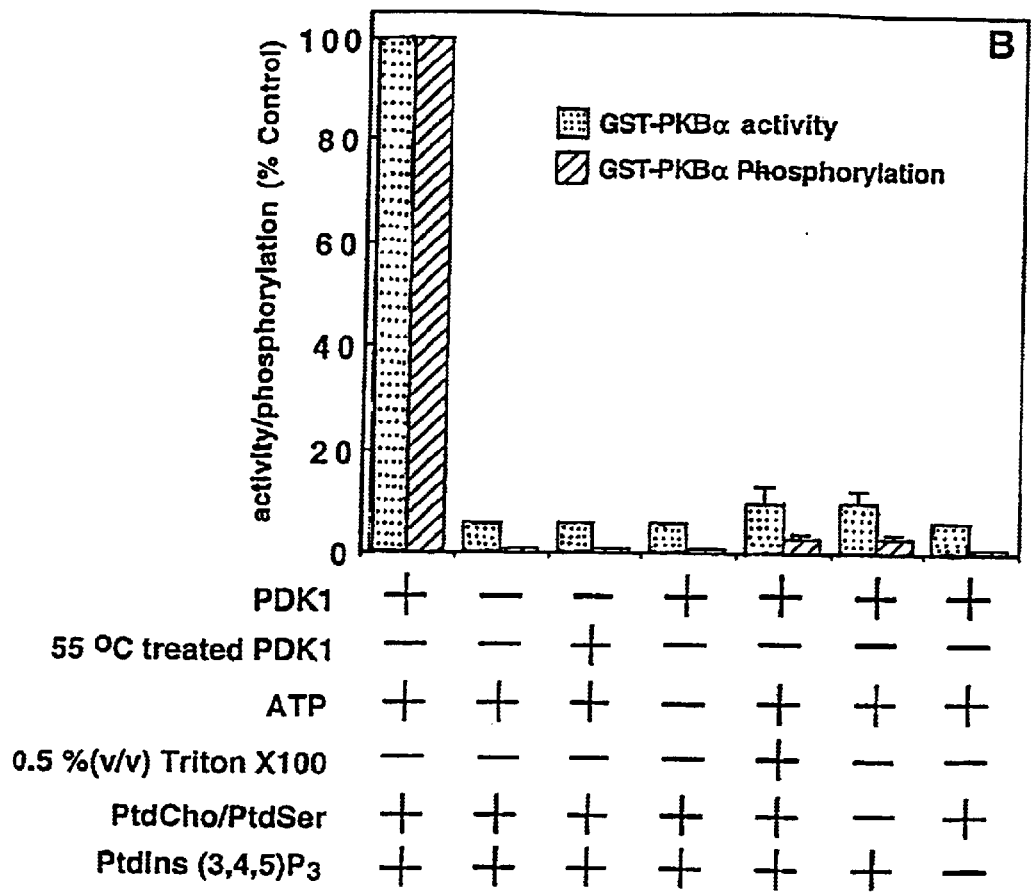

FIGS. 3A and 3B PDK1 phosphorylates and activates GST-PKBα. (A) GST-PKBα (0.5 μM) was incubated with PDK 1 (12 U/ml), 10 mM Mg(Ac) 2, 100 μM [γ$^{32}$P]ATP, and vesicles comprising 100 μM PtdCho, 100 μM PtdSer, 10 μM D-enantiomer of sn-1-stearoyl-2-arachidonyl PtdIns(3,4,5) P3 in Buffer B. At various times, aliquots were removed and either assayed for PKBα activity (closed circles) or for incorporation of phosphate into PKBα (open circles). Activities are presented relative to control experiments in which PDK1 was omitted from the reaction mixture. Phosphorylation was assessed by counting the $^{32}$P-radioactivity associated with the band of GST-PKBα after SDS-PAGE. (B) Same as (A) except that the effects of omitting PDK1, ATP, PtdSer/PtdCho, PtdIns(3,4,5)P3, heating PDK1 at 55° C. for 2 min, or adding 0.5% (by vol) Triton X-100 in the PDK1 assay were studied. The assays were carried out for 60 min. Closed bars show GST-PKBα activity and hatched bars GST-PKBα phosphorylation relative to a control assay in which PDK1, ATP, PtdCho/PtdSer and PtdIns(3,4,5)P3 were present. The results are presented as±SEM for six determinations (two independent experiments).

FIG. 4. Dependence of PDK1 activity on PtdIns(3,4,5)P3 concentration. GST-PKBα (0.5 μM) was incubated with PDK1 (12 U/ml), 10 mM MgAc, 100 μM [γ$^{32}$P]ATP and the indicated concentrations of D-enantiomer of 1-stearoyl-2-arachidonyl PtdIns(3,4,5)P3 in either the presence of constant concentration of PtdCho and PtdSer (100 μM of each open circles) or in the presence of a 10 fold molar excess of the PtdSer/PtdCho (closed circles). After 30 min the extent of activation (A) and phosphorylation (B) of GST-PKBα was assessed as described in Materials and Methods. The results are presented as ±SEM for 2 experiments, each carried out in triplicate.

Figure 5:
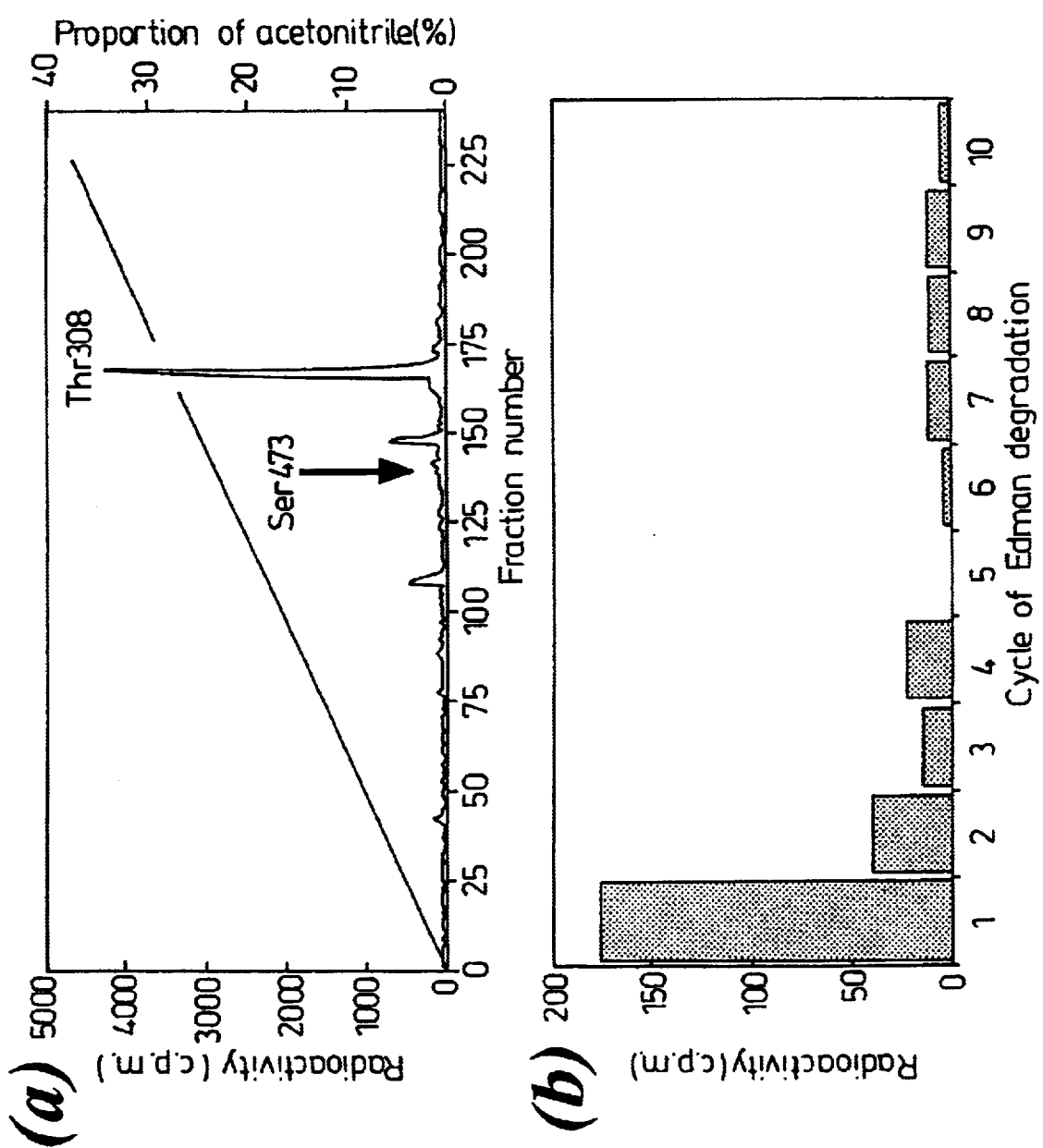

FIG. 5. PDK1 phosphorylates PKBα at Thr-308. (A) GST-PKBα was phosphorylated by incubation for 60 min with PDK1 (12 U/ml), and phospholipid vesicles comprising PtdCho, PtdSer, D-enantiomer of 1-stearoyl-2-arachidonyl PtdIns(3,4,5)P3, and Mg[γ32P]ATP (see legend to FIG. 3), and then alkylated and digested with trypsin (see Methods). The digest was applied to a Vydac 218TP54 C18 column (Separations Group, Hesperia, Calif.) equilibrated in 0.1% (v/v) trifluoroacetic acid (TFA) in water. The column was developed with a linear acetonitrile gradient (diagonal line) at a flow rate of 0.8 ml/min and fractions of 0.4 ml were collected. 35% of the radioactivity applied to the column was recovered from the major $^{32}$P-containing peptide at 26% acetonitriie(the remainder of the radioactivity eluted as numerous minor peaks). The elution positions of the tryptic peptides which contain Thr-308 and Ser473 are marked [15]. (B) A portion of the major $^{32}$P-containing peptide (500 cpm) from A was coupled covalently to a Sequelon arylamine membrane and analysed on an Applied Biosystems 470A sequencer using the modified programme described in [30]. $^{32}$P radioactivity was measured after each cycle of Edman degradation.

FIG. 6. PDK-1 is activated specifically and stereospecifically by PtdIns(3,4,S)P3 and PtdIns(3,4)P2 lipids. GST-PKBα was incubated for 30 min at 30° C. with Mg[γ$^{32}$P] ATP in the presence (filled bars) and absence (open bars) of PDk1 and phospholipid vesicles containing 100 μM PtdCho, 100 μM PtdSer, and various PtdIns lipids (numbered 1–11, see below) or Ins (1,3,4,5)P$_4$, all at a final concentration of 10 μM in the assay. Reactions were terminated by the addition of 1% (by vol) Triton X-100 to the assay and in (A) the activity of GST-PKBα was determined as described under Methods. (B) The phosphorylation of GST-PKBα was assessed by autoradiography of the Commassie blue-stained band corresponding to GST-PKBα (FIG. 1). The results are presented as fold-activation of GST-PKBα ±SEM for 6–8 determinations (three independent experiments). Lipids 1 and 2 are the D and L-enantiomers of sn-1-stearoyl-2-arachidonyl PtdIns(3,4,5)P3 respectively, and lipids 3 and 4 are the D and L-enantiomers of sn-2-arachidonyl-3-stearoyl PtdIns(3,4,5)P3 respectively. Lipid 5 is racemic sn-1,2-dilinoleoyl PtdIns(3,4,5)P3. The remaining lipids are all D-enantiomers. Lipid 6 is sn-1,2 di-palmitoyl PtdIns(3,4,5) P3, lipid 7 is sn-1,2 di-palmitoyl PtdIns(3,4)P2, lipid 8 is sn-1,2 di-palmitoyl PtdIns(3,5)P2. Lipid 9 is PtdIns(4,5)P2, and lipid 10 is PtdIns 4P which are both purified lipid derived from Folch fraction type-I brain extract. Lipid 11 is sn-1,2 di-palmitoyl PtdIns-3P. 1P$_4$ is Ins(1,3,4,5)P4.

Figure 7:
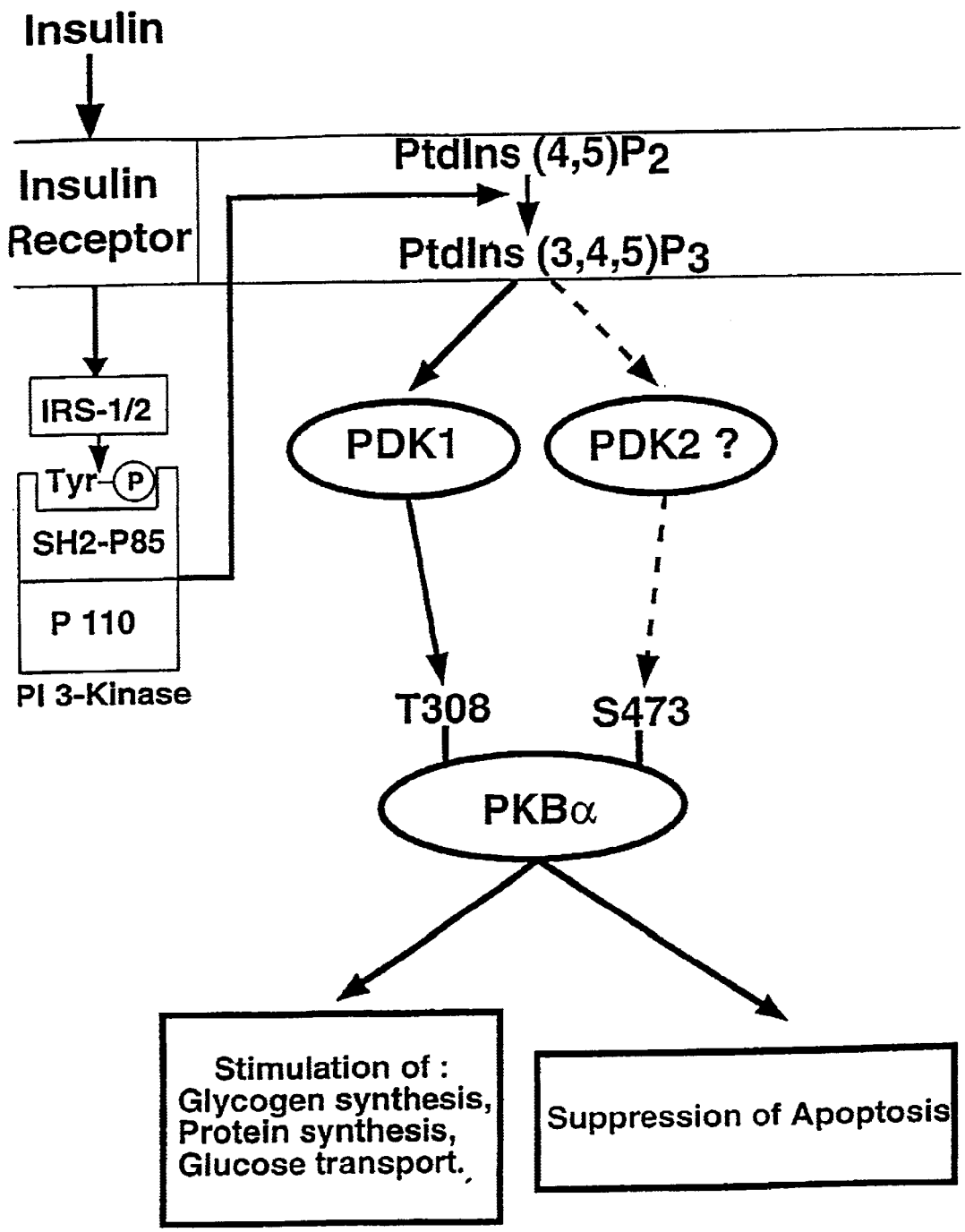

FIG. 7. Proposed mechanism by which insulin induces the activation of PKBα. The activation of the insulin receptor by insulin causes the receptor to phosphorylate itself at several tyrosine residues. This leads to the docking of insulin receptor substrate-1 (IRS-1) and IRS-2 and their phosphorylation at multiple tyrosine residues by the insulin receptor. Several phosphorylated tyrosine residues on IRS1 and IRS2 then interact with SH2 domains on the p85 subunit of PI 3-kinase, leading to the recruitment of the p 110 catalytic subunit of PI 3-kinase to cell membranes and its activation [31]. PI 3-kinase then phosphorylates PtdIns(4,5)P2 at the D-3 position of the inositol ring, resulting in the formation of the second messenger PtdIns(3,4,5)P3 whose levels (in a typical cell) rise from 0.1% to 1–2% of the PtIns(4,5)P2 content in the plasma membrane [31]. PtdIns(3,4,5)P3 interacts with, and activates PDK1 which partially activates PKBα by phosphorylating it at Thr-308. Maximal activation of PKBα also requires the phosphorylation of Ser-473 by an unknown kinase. The insulin-induced phosphorylation of Ser-473, like the phosphorylation of Thr-308, is prevented by inhibitors of PtdIns 3-kinase [15], suggesting that Ser-473 may be phosphorylated by a distinct 3-phosphoinositide-dependent protein kinase (PDK2). However, the Ser-473 kinase may be activated indirectly by 3-phosphoinositides by mechanisms discussed in the text. For this reason, the pathway from PtdIns(3,4,5)P3 to the phosphorylation of Ser-473 is shown by broken lines with a question mark after PDK2. In skeletal muscle, the activation of PKBα may increase the rate of glucose uptake [9] and glycogen synthesis [7] and stimulate protein translation [8]. In neurons and other cells PKBα activation may provide a survival signal by suppressing apoptosis [10,11].

FIG. 8. Details of IMAGE Consortium clone ID 526583 (SEQ ID NO: 27)

FIG. 9. Details of IMAGE Consortium clone ID 626511 (SEQ ID NO: 28)

Figure 10A:
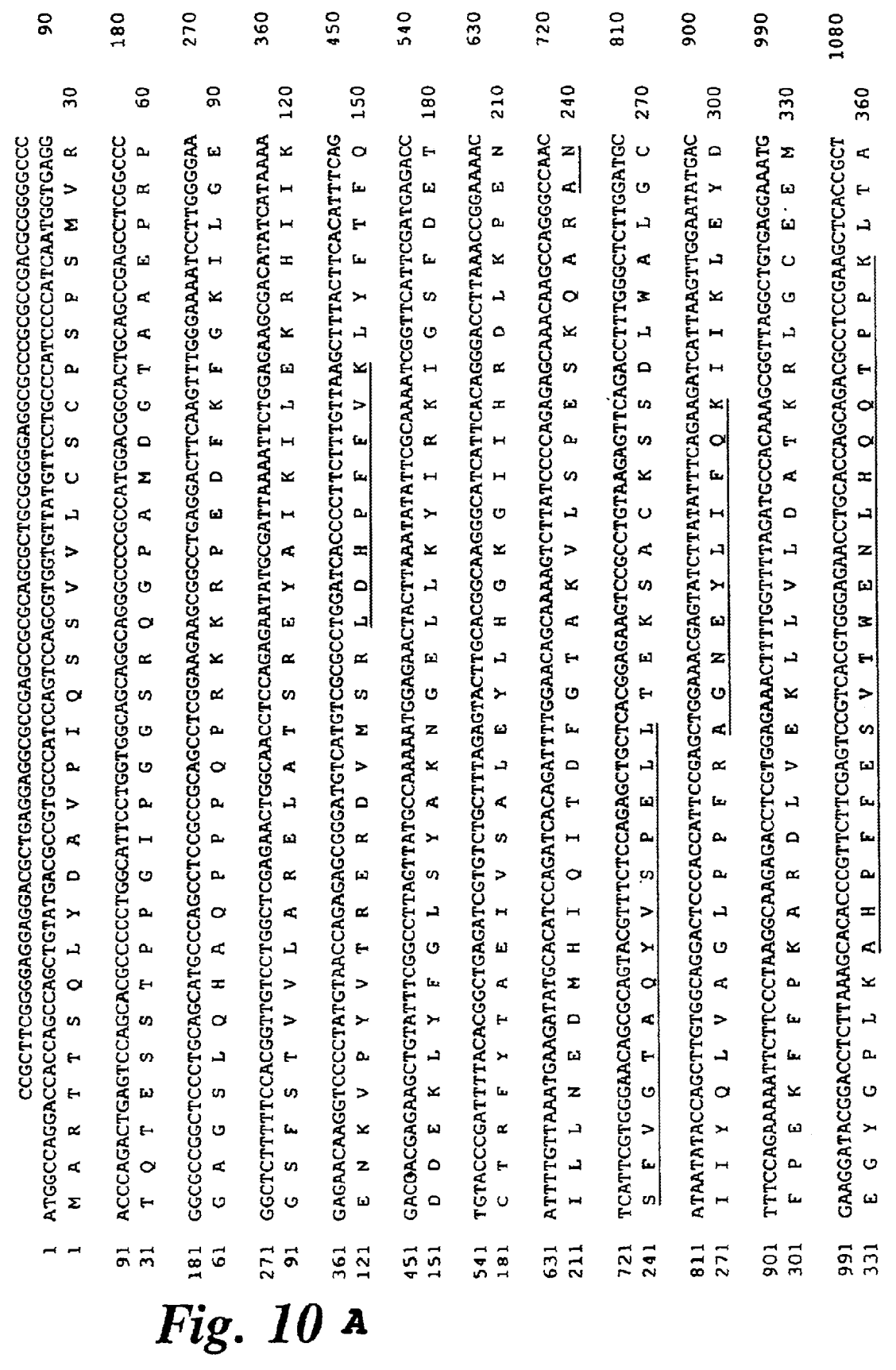

FIGS. 10A and 10B. Nucleotide sequence coding for, and deduced amino acid sequence of, PDK1(SEQ ID NO: 2 and SEQ ID NO: 1, respectively).

FIG. 11. Alignment of the anino acid sequences of human PDK1 and Drosophila DSTPK61(SEQ ID NO: 29. The alignment was carried out using the Clustal W program [46]. Asterisks indicate identities between PDK1 and STK61. The catalytic domain comprises residues 83–342 of PDK1 and residues 165–487 of STPK61. The putative PH domains lie between residues 450 and 550 of PDK1 and 581 and 684 of STPK61B.

Figure 12:
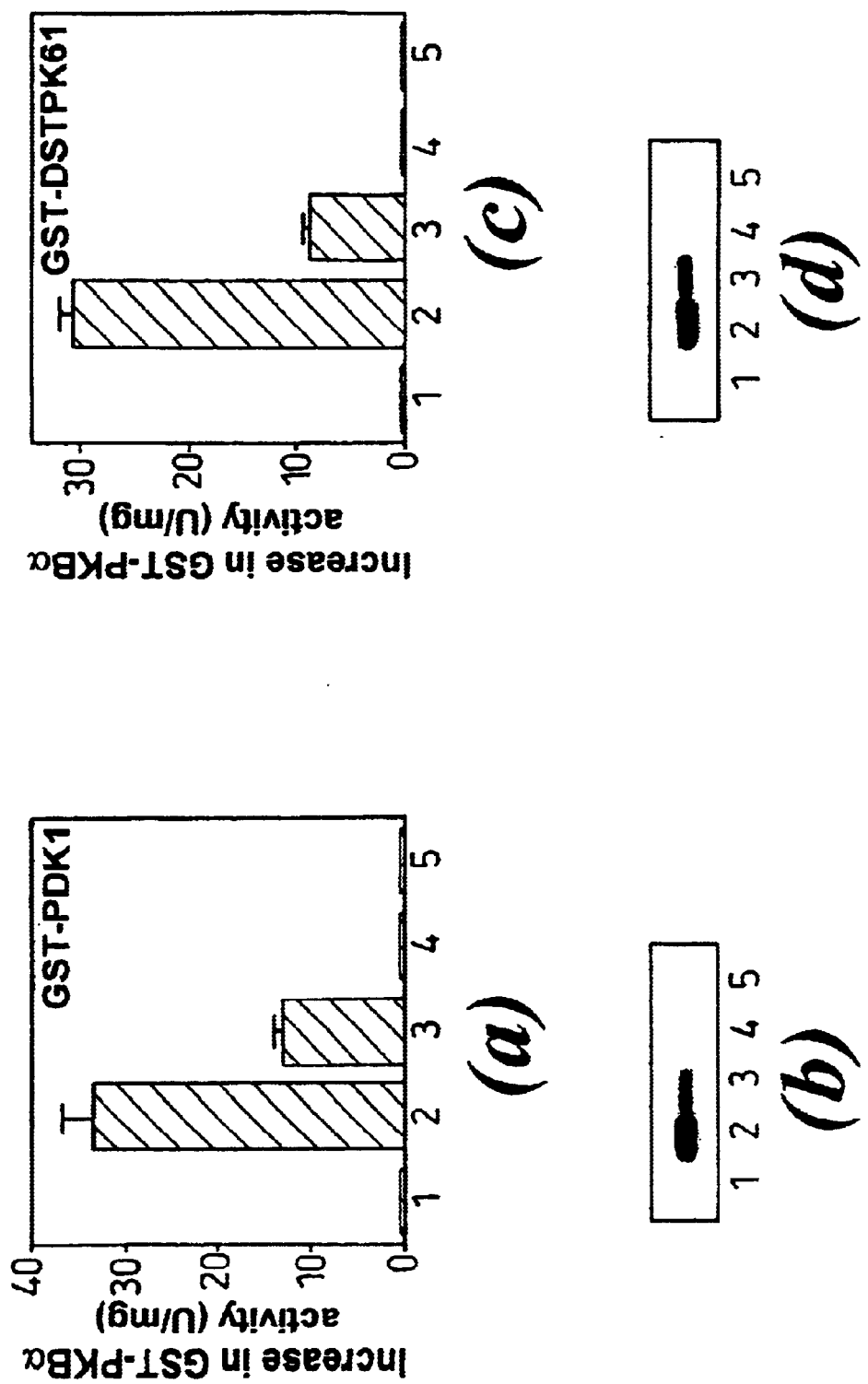

FIG. 12. GST-PDK1 and GST-DSTPK61 activate and phosphorylate PKBα in a PtdIns(3,4,5)P$_3$ or PtdIns(3,4)P$_2$ dependent manner. GST-PKBα was incubated for 30 min at 30° C. with either 5 U/ml GST-PDK1 (panels A, B) or GST-DSTPK61 (panels C, D) with Mg[γ$^{32}$P]ATP and phospholipid vesicles containing 100 μM PtdCho, 100 μM PtdSer, and various PtdIns lipids (numbered 1–5, see below) all at a final concentration of 10 μM in the assay. Under these conditions, the increase in PKBα activity and phosphorylation was linear with respect to time (see Methods). In panels A and C, the assays were terminated by making the incubations 1% (by vol) in Triton X-100 (see Ref 21), and the increase in specific activity of GST-PKBα was determined. In panels B and D, the reactions were terminated by making the solutions 1% in SDS, the samples were subjected to SDS/polyacrylamide gel electrophoresis, and the phosphorylation was assessed by autoradiography of the Coomassie blue-stained band corresponding to GST-PKBα. The results are presented in panels A and C as the increase in the specific activity of GST-PKBα (U/mg), relative to a control incubation in which GST-PDK1 or GST-DSTPK61 was omitted (±SEM for 6–9 determinations, three independent experiments). Under all conditions the increase in both activity and phosphorylation of GST-PKBa was linear with time. Track 1, buffer control; Track 2, sn-1-stearoyl-2-arachidonyl-D-PtdIns(3,4,5)P$_3$; Track 3, sn-1,2 di-palmitoyl-D-PtdIns(3,4)P$_2$; Track 4 is PtdIns(4,5)P$_2$ (purified from Folch brain fraction); Track 5, sn-1,2 di-palmitoyl-D-PtdIns-3P.

Figure 13:
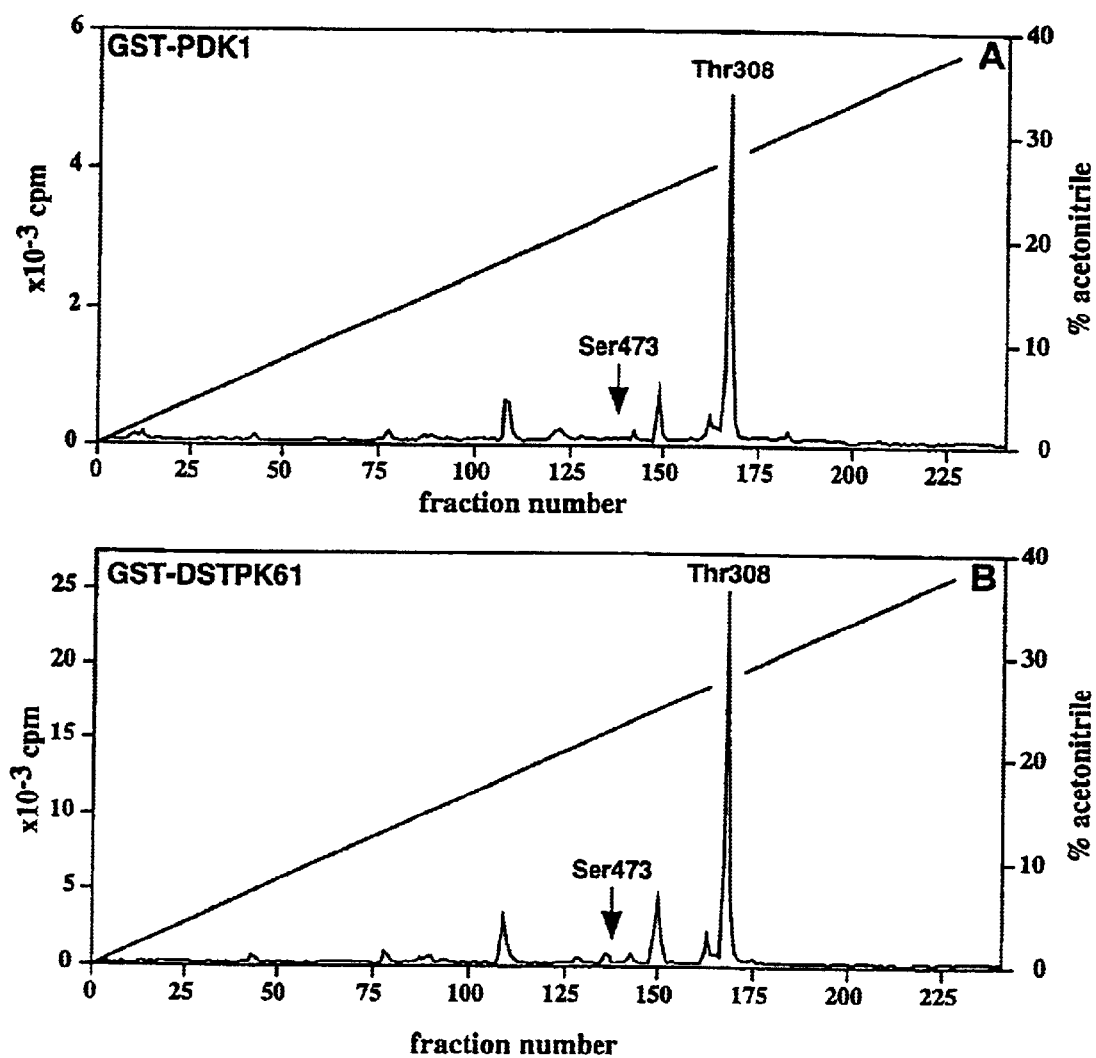

FIG. 13. PDK1 phosphorylates PKBα at Thr308. GST-PKBα was maximally phosphorylated by incubation for 30 min with 25 U/ml of either GST-PDK1 (A) or GST-DSTPK61 (B) and phospholipid vesicles comprising PtdCho, PtdSer, the D-enantiomer of 1-stearoyl-2-arachidonyl PtdIns(3,4,5)P$_3$, and Mg[γ$^{32}$P]ATP (10$^6$ cpm per nmol). After 30 min, the samples were alkylated with 4-vinylpyridine, digested with trypsin [21] and applied to a Vydac 218TP54 C$^{18}$ column (Separations Group, Hesperia, Calif.) equilibrated in 0.1% (v/v) trifluoroacetic acid (TFA). The column was developed with a linear acetonitrile gradient (diagonal line) at a flow rate of 0.8 ml/min and fractions of 0.4 ml were collected. 38% (panel A) and 45% (panel B) of the radioactivity applied to the column was recovered in the major $^{32}$P-containing peptide eluting at 26% acetonitrile, while contains Thr308. The elution position of the typtic peptide containing Ser473 is also marked [see ref 20 and FIG. 15].

FIG. 14. PKBα is activated by cotransfection with PDK1 in 293 cells. (A) 293 cells were transiently transfected with DNA constructs expressing either HA-PKBα or both HA-PKBα and Myc-PDK1. The cells were then stimulated for 10 min with or without 50 ng/ml IGF1, the HA-PKBα immunoprecipitated from the lysates and assayed. The results are expressed relative to the specific activity of wild type HA-PKBα in unstimulated 293 cells (0.03±0.5 U/mg). No PKBα activity was detected in mock transfections in which the cells were transfected with PCMV5 vector alone (data not shown). (B) 6 μg of protein from each lysate was electrophoresed on a 10% SDS/polyacrylamide gel and immunoblotted using either a monoclonal HA-antibody to detect HA-PKBα or a monoclonal Myc-antibody to detect Myc-PDK1. The molecular mass markers are glycogen phosphorylase (97 kDa), bovine serum albumin (67 kDa) and ovalbumin (43 kDa).

FIG. 15. Overexpression of PDK1 in cells induces phosphorylation of PKBα at Thr308. 293 cells transiently transfected with either wild type HA-PKBα (panels A and C) or HA-PKBα and Myc-PDK1 (panels B and D) were incubated with $^{32}$P-orthophosphate, then treated for 10 min without (panels A and B) or with (panels C and D) 50 ng/ml IGF1. The $^{32}$P-labelled HA-PKBα was immunoprecipitated from the lysates, treated with 4-vinylpyridine, and electrophoresed on 110% polyacrylamide gel. The HA-PKBα was excised from the gel, digested with trypsin and chromatographed on a C$_{18}$ column (see legend to FIG. 13) to resolve the four major phosphopeptides which are phosphorylated at Ser-124, Ser473, Thr308 and Thr450 respectively [20]. The identity of each phosphopeptide was established by phospho-amino acid analysis and solid phase sequencing. Similar results were obtained in two separate experiments for (panels A and C), and in three separate experiments (panels B and D).

FIG. 16. Role of the PH domains of PKBα and PDK1. (A) 0.5 μg of either GST-PKBα or GST-ΔPH-PKBα were incubated for 30 min at 30° C. with either 2.3 nM GST-PDK1 (residues 1–556) with Mg[γ$^{32}$P]ATP and phospholipid vesicles containing 100 μM PtdCho, 100 μM PtdSer either in the presence or absence of 10 μM PtdIns(3,4,5)P3 in a 20 μl assay. The assays were terminated by making the incubations 1% (by vol) in Triton X-100 as in Example 1, and the increase in specific activity of GST-PKBα was determined. The basal activity of GST-PKBγ was 2.5 U/mg and that of GST-ΔPH-PKBα was 8 U/mg. At the high concentration of GST-PDK1 used in this assay the rate of activation of full length wild type GST-PKBα is not linear with time whereas the activation of GST-ΔPH-PKBα is linear. When the experiments are carried out at 20-fold lower concentrations of GST-PDK1 a similar extent of activation of wild-type GST-PKBα is achieved as that shown in the figure for GST-ΔPH-PKBα by 2.3 nM GST-PDK1. (B) as in (A) except that 0.5 μg of GST-PKBα was incubated with 2.5 nM GST-ΔPH-PDK1 (residues 1 to 450) in the presence of phospholipid vesicles containing 100 μM PtdCho, 100 μM PtdSer and 10 μM of either, sn-1-stearoyl-2-arachidonyl-D-Ptd(3,4,5)P3 (Track 1); sn-1-stearoyl-2-arachidonyl-L-PtdIns(3,4,5)P3 (Track 2), sn-1,2 di-palmitoyl-D-PtdIns(3,4,5)P3 (Track 3), sn-1,2 di-palmitoyl-D-PtdIns(3,4,5)P3 (Track 4), PtdIns(4,5)P2 (purified from Folch brain fraction Track 5) and sn-1,2 di-palmitoyl-D-PtdIns-3P (Track 6). The results are presented as the increase in the specific activity of GST-PKBα (U/mg), (±SEM for 6–9 determinations, three independent experiments), relative to a control incubation in which GST-PDk1 is omitted.

Figure 17:
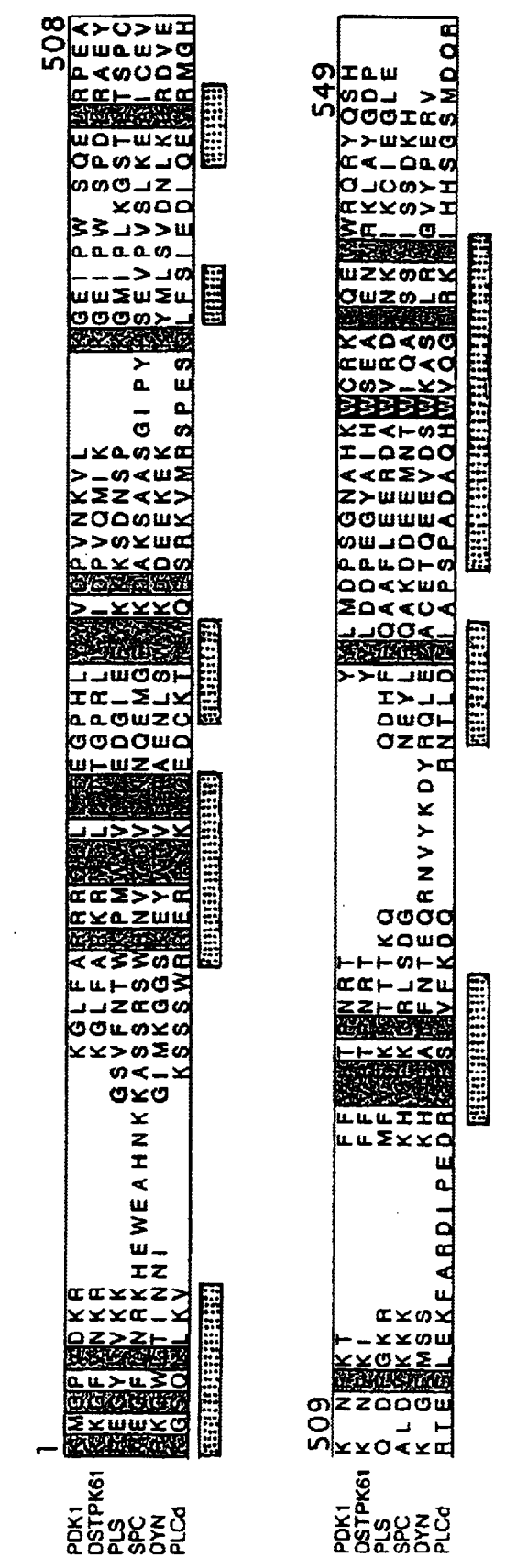
Figure 18:
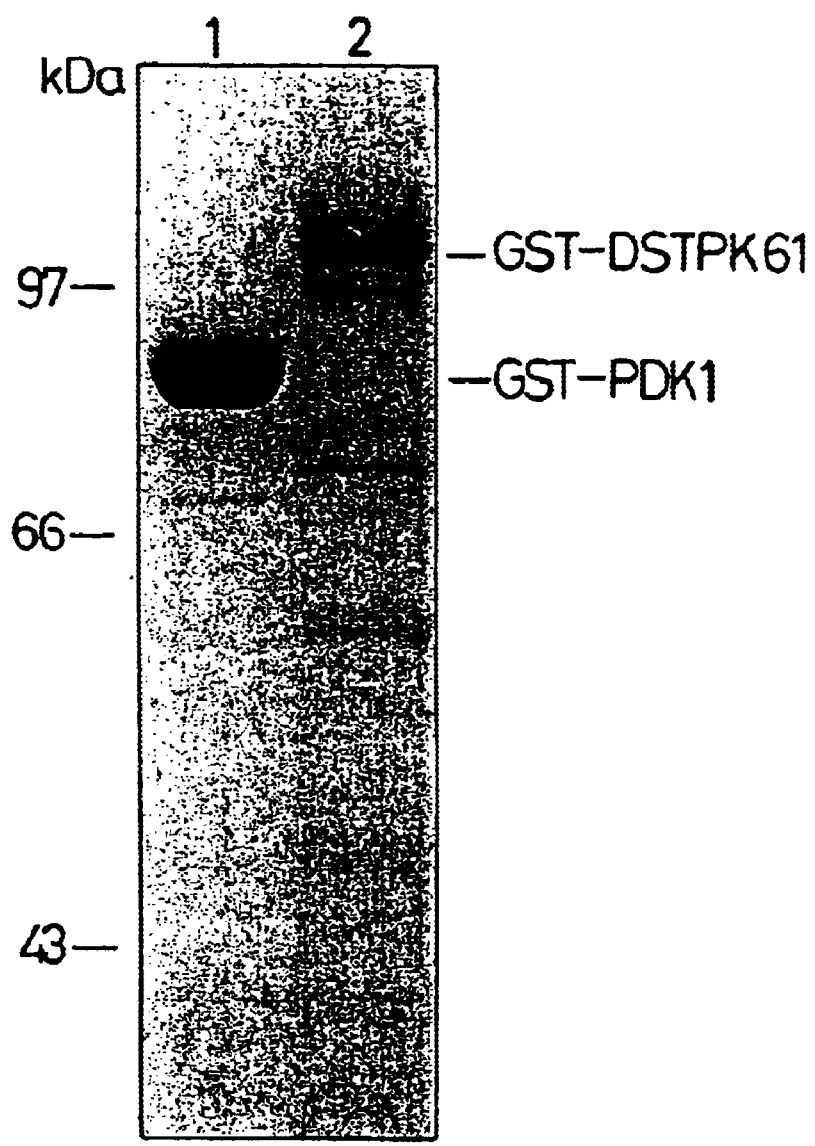

FIG. 17. Evidence that PDK1 and DSTPK61 possess a Pleckstrin-Homology domain. Sequence alignment of PH domains that have a known tertiary structure with the putative PH domains of PDk1 and DSTPK61 (SEQ ID NO: 30–35). Alignment was done using the program AMPS (Barton & Sternberg (1990) *J. Mol. Biol.* 212, 389–402) and formatted using AMAS (Livingstone & Barton (1993) *Comp. Appl. Bio. Sci.* 9, 745–756) with some manual adjustment to ensure coincidence of secondary structure regions. Regions containing conserved residues are coloured green and the invariant tryptophan (Trp-535) is coloured red. General regions of secondary structure are denoted by the blue (beta strand) and green (alpha helix) bands. The Pleckstrin-Homology sequences are those found in human Pleckstrin, PLS; human spectrin, SPC; human dynamin DYN, and rat phospholipase C-δ, PLCδ. Numbering is based on the PDK1 sequence FIG. 18. SDS Polyacrylamide gel of purified GST-PDK1 and GST-DSTPK61. GST-PDK1 encoding residues 52–556, Lane 1. 3 μg protein) and GST-DSTPK61 (Lane 2. 6 μg protein) were electrophoresed on 1 7.5% SDS polyacrylamide gel and stained with Coomassie blue. The position of the molecular mass markers, glycogen phosphorylase (97 kDa), bovine serum albumin (67 kDa) and ovalbumin (43 kDa) are indicated. The other GST-PDK1 constructs used in this study were all expressed at a similar level of purity as the GST-PDK1 preparation shown in Lane 1 (data not shown).

EXAMPLE 1

Purification and Characterisation of a 3-Phosphionositide-dependent Protein Kinase (PDK1) That Phosphorylates and Activates Protein Kinase Bα

SUMMARY

Background: Protein kinase B (PKB), also known as c-Akt, is activated rapidly when cells are stimulated with insulin and growth factors, and much of the current interest in this enzyme stems from the observation that it lies downstream of phosphoinositide 3-kinase. We recently showed that insulin or IGF1 induce the phosphorylation of PKB at Thr-308 and Ser-473. The phosphorylation of both residues is required to activate PKB maximally, and the insulin or IGF1-induced phosphorylation of both residues is prevented by incubating cells with inhibitors of PI-3 kinase.

Results: A protein kinase has been purified 500,000-fold from rabbit skeletal muscle extracts which phosphorylates protein kinase Bα (PKBα) at Thr-308 and increases its activity >30-fold. The kinase was only active in the presence of low micromolar concentrations of phosphatidylinositol 3,4,5-trisphosphate [PtdIns(3,4,5)P3] or phosphatidylinositol 3,4-bisphosphate [PtdIns(3,4)P2] and has therefore been termed PtdIns(3,4,5)P3-dependent protein kinase-1 (PDK1). The D-enantiomers of sn-1-stearoyl-2-arachidonyl PtdIns(3,4,5)P3 and sn-2-arachidonyl-3-stearoyl PtdIns(3,4,5)P3 potently activated PDK1, but the L-enantiomers of these derivatives were almost ineffective. sn-1,2-dipalmitoyl PtdIns(3,4,5)P3 and sn-1,2-dipalmitoyl PtdIns(3,4,)P2 both activated PDK1 to a similar extent, but were~3-fold less effective than the sn-1-stearoyl-2-arachidonylandsn-2-arachidonyl-3-stearoylderivatives. PtdIns(3,5)P2, PtdIns(4,5)P2, PtdIns(4)P, PtdIns(3)P and inositol 1,3,4,5-tetrakisphosphate did not activate PDK1 at all. None of the inositol phospholipids tested activated or inhibited PKBα or induced its phosphorylation under the same conditions. PDK1 activity was unaffected by wortmannin, indicating that it is not likely to be a PI 3-kinase family member.

Conclusions: PDK1 is likely to be one of the protein kinases which mediate the activation of PKB by insulin and growth factors. PDK1 may therefore play a key role in mediating many of the actions of the second messengers, PtdIns(3,4,5)P3 and/or PtdIns(3,4)P2.

Materials and Methods

Materials. PtdSer (pig brain) was purchased from Doosan Serdary Research Laboratories (New Jersey, USA) and sn-1-stearoyl-2-arachidonyl PtdCho from Sigma (Poole, UK). PtdIns 4P and PtdIns(4,5)P2 were purified as described previously from Folch fraction type-1 extract of bovine brain (Sigma) [26]. Synthetic sn-1,2-dipalmitoyl analogues of PtdIns(3,4,5)P3, PtdIns(3,4)P2, PtdIns(3,5)P2 and PtdIns 3P were made as described previously[18]. Synthetic D and L enantiomers of sn-1-stearoyl-2-arachidonyl PtdIns(3,4,5)P3, sn-2-arachidonyl-3-stearoyl PtdIns(3,4,5)P3 and the D enantiomer of sn-1-linoleoyl-2-linoleoyl PtdIns(3,4,5)P3 were synthesised from inositol (Gaffney and Reece 1997, manuscript submitted for publication). All phospholipids were 97–98% pure. Synthetic phosphatidylinositol bisphosphates were stored at −20° C. as solutions in dimethyl sulphoxide (DMSO) and phosphatidylinositol trisphosphates in either DMSO or water. All other phospholipids were stored in chloroform-methanol solvents. The peptide used to assay PKBα,(RPRAATF) (SEQ ID NO: 9) [16] and TTYADFIASGRTGRRNAIHD (SEQ ID NO: 10)(the specific peptide inhibitor of cyclic AMP dependent protein kinase, termed PKI) were synthesised by Mr F. Barry Caudwell (MRC Protein Phosphorylation Unit, Dundee) on an Applied Biosystems 431A peptide synthesiser, and their concentrations were determined by quantitative amino acid analysis. Glutathione Sepharose was purchased from Pharmacia (Milton Keynes, UK) and alkylated trypsin from Promega (Southampton, UK).

Buffer Solutions:

Buffer A; 50 mM Tris/HCl pH 7.5, 1 mM EDTA 1 mM EGTA, 1% (by vol) Triton X-100, 1 mM sodium orthovanadate, 10 mM sodium β-glycerophosphate, 50 mM NaF, 5 mM sodium pyrophosphate, 1 μM Microcystin-LR, 0.27 M sucrose, 1 mM benzamidine, 0.2 mM phenylmethylsulphonyl fluoride (PMSF), 10 μg/ml leupeptin, 0.1% (by vol) 2-mercaptoethanol.

Buffer B; 50 mM Tris/HCl pH 7.5, 0.1 mM EGTA, 0.03% (by vol) Brij-35, 0.27 M sucrose, 0.1% (by vol) 2-mercaptoethanol.

Buffer C; 50 mM Tris/HCl pH 7.5, 2 mM EDTA, 2 mM EGTA, 50 mM NaF 0.1% (by vol) 2-mercaptoethanol, 0.1 mM PMSF, 1 mM benzamidine.

Expression of GST-PKBα in 293 cells. The DNA sequence encoding PKBα was subcloned into the eukaryotic expression vector PEBG2T that has been used to overexpress GST-fusion proteins in eukaryotic cells under an EF1α promoter [27]. A PCR reaction was set up to generate a full length cDNA encoding the PKBα gene with a BamHI site at the 5' end of the cDNA that is in frame with the GST sequence of the PEBG2T vector and the ATG initiation codon of PKBα, and a KpnI site at the 3' end, using the human PCMV5-HA-PKBα plasmid [15]. The DNA sequence of the BamHI/KpnI cDNA fragment was checked and then subcloned into the unique BamHI/KpnI restriction sites on the pEBG 2T expression vector. In order to prepare GST-PKBα, 40, 10 cm diameter dishes of human embryonic kidney 293 cells were cultured and each dish transfected with 20 μg of GST PKBα expression construct using the modified calcium phosphate method described previously for overexpression of haemaglutinin tagged PKBα in 293 cells [15 ]. 24 h after transfection, the cells were serum starved for 16 h and each dish of cells lysed in 1 ml of ice-cold Buffer A. The 40 lysates were pooled, centrifuged at 4° C. for 10 min at 13,000×g and the supernatant incubated for 60 min on a rotating platform with 800 μl of glutathione-Sepharose previously equilibrated in Buffer A. The suspension was centrifuged for 1 min at 3000×g, the beads washed three times with 10 ml of Buffer A containing 0.5 M NaCl, and then a further 10 times with 10 ml of Buffer B to ensure complete removal of all the Triton X-100 which interferes with the activation of GST-PKBα by PDK1 (FIG. 3B). GST-PKBα was eluted from the resin at ambient temperature with three 1 ml portions of Buffer B containing 20 mM glutathione pH 8.0. The combined eluates (0.65 mg/ml protein) were divided into aliquots, snap frozen in liquid nitrogen, and stored at −80° C.

Preparation of Phospholipid Vesicles

Phospholipid vesicles comprising 1 mM PtdCho, 1 mM PtdSer and 0.1 mM PtdIns lipids were prepared, dried to a film under vacuum and resuspended with vortexing into 10 mM Hepes, pH 7.3. The cloudy solution of multilamellar and large unilamellar vesicles was bath-sonicated for 20 min, after which a clearer suspension of smaller unilamellar vesicles was obtained. Solutions were stored at 4° C. at concentrations 10-fold higher than those required in the assay and used within 2–4 days.

Purification of PDK1 from Rabbit Skeletal Muscle

Day 1. A female New Zealand White rabbit was killed with a lethal dose of sodium pentobarbitone. Skeletal muscle from the hind limbs and back (500g) was excised rapidly and placed on ice. All subsequent steps were carried out at 0–4° C. The muscle was minced, homogenized in 2.5 vol of 25 mM Tris/HCl pH 7.5, 4 mM EDTA, 2 mM EGTA, 50 mM NaF, 0.1% (by vol) 2-mercaptoethanol, 0.1 mM PMSF and 1 mM benzamidine and centrifuged for 30 min at 4200×g. The supernatant was filtered through glass wool and poured through a Buchner funnel containing 10 g of QAE-Sephadex equilibrated in Buffer C. The column was washed with one litre of Buffer C containing 50 mM NaCl, and washed with 700 ml of Buffer C containing 0.2 M NaCl to elute PDK1. A 50% (by mass) solution of polyethylene glycol (PEG) was added to the eluate to bring the final concentration of PEG to 4%. After stirring on ice for 60 min, the suspension was centrifuged for 15 min at 10000×g. The supernatant was decanted and made 15% in PEG by further addition of 50% (by mass) PEG. After stirring for a further 60 min on ice, the suspension was again centrifuged for 15 min at 10000×g. The supernatant was discarded and the precipitate dissolved in 5ml of ice cold Buffer B, filtered through a 0.25 μm filter and then chromatographed on an SP-Sepharose column (11×1.6 cm) equilibrated in Buffer B. The column was developed with a 300 ml linear gradient of NaCl to 0.5 M at a flow rate of 3 ml/min and 6 ml fractions were collected (FIG. 2A). The active fractions were pooled and applied directly on to a 5 ml heparin-Sepharose column (HiTrap) equilibrated in Buffer B containing 0.1 M NaCl. The column was developed with a 90 ml linear salt gradient to 0.9 M NaCl at a flow rate of 2 ml/min and fractions of 1 ml were collected. PDK1 activity eluted as 2 peaks. Peak-1, comprising ~30% of the activity, was eluted at 0.5 M NaCl, while Peak 2 comprising ~70% of the activity, eluted at 0.7 M NaCl (FIG. 2B).

Day 2. The active fractions of Peak 2 were pooled concentrated to 0.2 ml by ultrafiltration, diluted to 2.0 ml in Buffer B, and loaded on to a Mono S column (5 cm×1.6 mm) equilibrated in Buffer B. The column was developed with a 4.0 ml linear gradient of salt to 0.15 M MgCl2 at a flow rate of 0.2 mil/min and 0.1 ml fractions were collected. Fractions containing PDK1 were aliquoted, snap frozen in liquid nitrogen, and stored at −80° C. No significant loss of activity occured upon thawing.

Assay of PDK1. The assay was carried out in two stages; in the first, GST-PKBα was incubated with PDK1 in the presence of MgATP and phospholipid vesicles to permit activation of GST-PKBα. In the second stage, the solution was made 0.5% (by vol) in Triton X100 (which completely inhibits phosphorylation and activation of GST-PKBα without affecting GST-PKBα activity, see FIG. 3B), together with Mg[γ32P]ATP, and the specific PKBα substrate peptide RPRTAAF(SEQ ID NO: 9)[16].

In Stage 1, an 18 μl reaction mixture was set up containing 50 mM Tris/HCl pH 7.5, 0.1 mM EGTA, 0.1% (by vol) 2-mercaptoethanol, 0.1 mM EGTA, 2.5 μM PKI, 1 μM microcystin-LR, 10 mM Mg(Ac)2, 100 μM unlabelled ATP, 0.6 μM GST-PKBα, 100 μM PtdSer, 100 μM PtdCho in the presence or absence of 10 μM PtdIns(3,4,5)P3. The assay was initiated by the addition of 2 μl of PDK1 and, after incubation for 30 min at 30° C., stage 2 of the assay was initiated by the addition of 30 μl of a mixture containing 50 mM Tris/HCl pH 7.5, 0.1 mM EGTA, 0.1% (by vol) 2-mercaptoethanol, 0.1 mM EGTA, 2.5 μM PKI, 1 μM microcystin-LR, 10 mM Mg(Ac) 2, 100 μM [γ$^{32}$P]ATP (200–400 cpm/pmol), 100 μM of the peptide RPRTAAF (SEQ ID NO: 9) and 1.25% (by vol) Triton X-100. After 10 min at 30° C., the reactions were terminated by spotting the reaction mixture on to p81 phosphocellulose paper. The papers were washed in phosphoric acid and analysed as described previously [28]. A control reaction in which GST-PKBα was omitted was taken as the blank and was always less than 5% of the activity measured in the presence of GST-PKBα. The basal GST-PKBα activity is the activity measured in the absence of PDK1. One Unit of PDK1 activity was defined as that amount required to increase the basal activity of GST-PKBα by 1 Unit of activity. 1 Unit of GST-PKBα activity was that amount of enzyme required to catalyse the phosphorylation of 1 nmol of the peptide RPRTAAF (SEQ ID NO: 9) in 1 min. The assays were linear with time up to a final concentration of 2 U/ml of PDK1 activity in the assay.

Phosphorylation of GST-PKBα by PDK1. The incubations were identical to the Stage 1 described above except that [γ³²P] ATP (200–400 cpm/pmol) was used instead of unlabelled ATP. The reactions were terminated by making the solution 1% (by mass) in SDS. The samples were run on a 7.5% SDS-polyacrylamide gel and, after staining with Coomassie blue, the gels were autoradiographed. The Coomassie blue-staining bands corresponding to GST-PKBα were excised and the ³²P-radioactivity associated with each band was quantified.

Mapping the site on GST-PKBα phosphorylated by PDK1. GST-PKBα was phosphorylated in the presence of the D-enantiomer of sn-1-stearoyl-2-arachidonyl PtdIns(3,4,5)P3 except that the scale of the reaction was increased 10-fold and the specific activity of the [γ³²P] ATP was increased to 1500 cpm/pmol. The reaction was stopped by the addition of SDS and 2-mercaptoethanol to final concentrations of 1% (by mass) and 1% (by vol) respectively, and heated for 5 min at 95° C. After cooling to ambient temperature, 2-vinylpyridine was added to a concentration of 2.5% (by vol) and the sample left on a shaking platform for 1 h at 30° C. to alkylate cysteine residues. The sample was then electrophoresed on a 7.5% SDS polyacrylamide gel, and the ³²P-labelled GST-PKBα eluted from the gel and digested with trypsin as described previously [15].

chromatography on QAE-Sephadex, the overall purification was about 500,000-fold, and the entire preparation could be completed within 36 h. PDK1 was eluted as a single peak from S-Sepharose (FIG. 2A), but resolved into two species on heparin-Sepharose. The minor component (Peak 1) eluted at 0.5M NaCl and the major component (Peak 2) at 0.7M NaCl (FIG. 2B). All further experiments were carried out with the Peak 2 enzyme from heparin-Sepharose further purified through Mono S (FIG. 2C), unless stated otherwise. After the final step the peak 2 enzyme, which was devoid of PKB activity, showed three major protein staining bands with apparent molecular masses of 85, 67 and 45 kDa. Only the 67 kDa band became phosphorylated upon incubation with MgATP and phosphorylation was greatly increased in the presence of PtdIns(3,4,5)P$_3$. The sequences of two tryptic peptides from the 67 kDa band were highly homologous to regions of the catalytic domains of other protein kinases (data not shown). The data indicate that PDK1 is a novel 67 kDa protein kinase, distinct from other protein kinases reported to be activated by PtdIns(3,4,5)P3, such as PKCε and PKCζ.

TABLE 1

Purification of PDK1 from rabbit skeletal muscle. 500 g of muscle was used in this preparation. The protein was estimated by the procedure of Bradford [29]. PEG, polyethyleneglycol.

| Step | Volume (ml) | Protein (mg) | Activity (U) | Specific activity (U/mg) | Purification (fold) | Yield (%) |
| --- | --- | --- | --- | --- | --- | --- |
| 1. Extract | 1400 | 17000 | not measurable | — | — | — |
| 2. QAE-Sephadex | 750 | 555 | 1330 | 2.4 | 1 | 100 |
| 3. 4–15% PEG | 55 | 164 | 1190 | 7.3 | 3 | 89 |
| 4. S-Sepharose | 88 | 10 | 610 | 61 | 25 | 46 |
| 5. Heparin-Sepharose | 11 | 0.01 | 290 | 29000 | 12000 | 22 |
| 6. Mono S | 0.3 | 0.002 | 139 | 69500 | 29000 | 10 |

Results

Purification of GST-PKBα from 293 cells. PKBα was expressed in 293 cells as a fusion protein with glutathione S-transferase (GST) at the N-terminus, and purified on glutathione Sepharose. The preparation showed a major Coomassie blue-staining protein band of apparent molecular mass 85 kDa corresponding to GST-PKBα (FIG. 1). The purity estimated by densitometric analysis of the gels was>70% and 2 mg of purified GST-PKBα was obtained routinely in each preparation made from 40, 10 cm dishes of 293 cells. GST-PKBα from unstimulated 293 cells possessed very low activity, but was activated 20-fold and 45-fold after stimulation-of 293 cells with insulin and IGF1, respectively (data not shown), indicating that it is recognised by the upstream protein kinase(s) that activates PKBα in vivo. GST-PKBα from unstimulated 293 cells was therefore used as the substrate with which to identify its upstream activators.

Identification of a PtdIns(3,4,5)P3 dependent protein kinase that activates PKBα. We identified an activator of GST-PKBα in skeletal muscle cytosol that eluted from QAE-Sephadex at 0.25 M salt and purified it a further 30,000-fold from the QAE-Sephadex eluate (Table 1). The activator was completely dependent on PtdIns(3,4,5)P3 for activity and, because it phosphorylates PKBα (see below), it is hereafter termed PtdIns(3,4,5)P3-dependent protein kinase-1 (PDK1).

PDK1 could not be detected in the crude cytosol, but assuming a recovery of 50% through the initial batchwise Phosphorylation and activation of GST-PKBα by PDK1. Purified PDK1 phosphorylated GST-PKBα in the presence of MgATP and phospholipid vesicles containing PtdCho, PtdSer and PtdIns(3,4,5)P3 to a level approaching 0.7 moles of 32P/mol protein (FIG. 3A). Phosphorylation was paralleled by a >30-fold increase in activity (FIG. 3A) which reached a specific activity of 80 U/mg. This is similar to the activity of PKBα which has been partially activated by mutating Thr-308 to Asp [15,16]. Omitting either PtdIns(3,4,5)P3 or PDK1 or ATP from the reaction abolished activation and phosphorylation of GST-PKBα (FIG. 3B). Moreover, addition of 0.5% (by vol) Triton-X100 to the assays also prevented the activation and phosphorylation of GST-PKBα by PDK1 (FIG. 3B), as did incubating PDK1 for 2 min at 55° C. In the absence of PtdCho/PtdSer vesicles, Ptd Ins(3,4,5)P3 was at least 15-fold less effective in activating PDK1 (FIG. 3B).

When PDK1 was incubated for 30 min at 30° C. in the presence of phospholipid vesicles containing PtdCho, PtdSer, PtdIns(3,4,5)P3 and MgATP, and then for 2 min at 55° C. to inactivate PDK1, the phospholipid vesicles were unable to activate or phosphorylate GST-PKBα, unless more PDK1 was added (data not shown). These observations establish that PDK1 does not activate GST-PKBα indirectly by converting PtdIns(3,4,5)P3 to another product that stimulates the autophosphorylation and autoactivation of GST-PKBα.

Dependence of PDK1 on PtdIns(3,4,5)P3 concentration. We next investigated the effect of varying the PtdIns(3,4,5)

P3 concentration on the ability of PDK1 to activate (FIG. 4A) and phosphorylate (FIG. 4B) GST-PKBα. These experiments were carried out either by varying the concentration of PtdIns(3,4,5)P3 whilst maintaining the concentration of both PtdCho and PtdSer at 100 μM or by maintaining a 10-fold excess of PtdCho and PtdSer over PtdIns(3,4,5)P$_3$. Under both conditions, the concentration of PtdIns(3,4,5)P3 required for half maximal activation or phosphorylation was 1–2 μM, with an optimal effect at 10 μM.

PDK1 phosphorylates Thr-308 of PKBα. In order to identify the residue(s) in PKBα phosphorylated by PDK1, 32P-labelled GST-PKBα that had been phosphorylated to 0.4–0.6 mol/mol with PDK1, was digested with trypsin and chromatographed on a C18 column [15]. One major $^{32}$P-labelled peptide was observed that eluted at 26% acetonitrile (FIG. 5A). This peptide, which coeluted with the $^{32}$P-labelled tryptic peptide containing Thr-308 [15], was found to contain phosphothreonine only (data not shown). When this peptide was subjected to solid phase sequencing, $^{32}$P-radioactivity was released after the first cycle of Edman degradation (FIG. 5B) corresponding to Thr-308 [15]. Importantly, no $^{32}$P-labelled peptide eluted at the position corresponding to the tryptic peptide containing Ser-473, which elutes at 24% acetonitrile (FIG. 5A, ref 15). These data establish that PDK1 only phosphorylates PKBα at Thr-308 in vitro.

Lipid specificity of PDK1. We next studied the ability of a panel of PtdIns derivatives to activate PDK1 when present in a vesicle background containing PtdCho/PtdSer. The predominant form of PtdIns(3,4,5)P3 which occurs naturally is likely to be predominantly sn-1-stearoy, 2-arachidonyl D-phosphatidylinositol 3,4,5-trisphosphate [17] (based on the structure and fatty acid composition of natural PtdIns). Synthetic sn-1-stearoyl, 2-arachidonyl D-PtdIns(3,4,5)P3 (lipid 1 in FIG. 6) proved highly effective, activating PDK1 activity 13-fold. By contrast, the L-enantiomer of this lipid induced only a 1.7-fold increase in PDK1 activity, which may be accounted for by trace contamination with the D-enantiomer. Whilst the enantiomeric configuration of the head group was of critical importance for activating PDK1, that of the glycerol moiety was not. Thus sn-2-arachidonyl, 3-stearoyl D- and L-PtdIns(3,4,5)P3 gave signals which were indistinguishable from the sn-1,2-derivatives (16-fold and 2.3-fold, respectively). The importance of unsaturated fatty acids in the diacylglycerol moiety is strongly indicated by the fact that sn-1,2-dilinoleoyl D-PtdIns(3,4,5)P3 (linoleic acid is C18:2) was the most effective lipid tested causing a 36-fold increase in GST-PKBα activity, whilst sn-1,2-dipalmitoyl D-PtdIns(3,4,5)P3 induced only a 5.5-fold activation (palmitic acid is C16:0). In each of these experiments, the phosphorylation of GST-PKBα (FIG. 6B) correlated with the extent of activation (FIG. 6A).

Interestingly, sn -1,2-dipalmitoyl PtdIns(3,4)P2 (lipid 7, FIG. 6) and sn -1,2-dipalmitoyl PtdIns(3,4,5)P3 (lipid 6, FIG. 6) activated PDK1 to the same extent, both inositol phospholipids increasing GST-PKBα activity about 6-fold. However, PtdIns(3,5)P2 (lipid 8 FIG. 6), PtdIns(4,5)P2 (lipid 9 FIG. 6), PtdIns 4P (lipid 10, FIG. 6), PtdIns 3 P (lipid 11, FIG. 6) and Ins(1,3,4,5)P4 did not activate PDK1 or induce the phosphorylation of GST-PKBα. In the absence of PDK1 none of the PtdIns derivatives tested induced any activation or phosphorylation of GST-PKBα (FIG. 6).

Discussion

The identification and purification of PDK1 was greatly fcilitated by the development of a specific peptide substrate (RPRAATF)(SEQ ID NO: 9) for PKBα [16]. Other substrates used to assay PKB, such as histone H2B, myelin basic protein and Crosstide are phosphorylated by many protein kinases in cell extracts and obscured the detection of PDK1. The use of soluble GST-PKBα as a substrate was also important because inununoprecipitated HA-PKB was not phosphorylated effectively by PDK1. PDK1 was found to phosphorylate PKBα at Thr 308 and to enhance its activity >30-fold. Since the phosphorylation of Thr-308 induced by insulin or IGF1 in vivo is prevented by inhibitors of PtdIns 3-kinase and PDK1 has an absolute requirement for PtdIns(3,4,5)P3 or PtdIns(3,4)P2, PDK1 is likely to be the enzyme which phosphorylates PKBα at Thr-308 in vivo. PDK1 activity is unaffected by wortmannin up to 2 μM (data not shown), indicating that it is not a PtdIns 3-kinase family member.

The full activation of PKBα in vitro requires the phosphorylation of Ser-473 as well as Thr-308 [15]. Thus mutation of either Thr-308 or Ser473 to Asp stimulates PKBα about 5-fold but, if both residues are mutated to Asp, activity is increased 18-fold. Similarly, phosphorylation of Ser473 stimulates PKBα activity 7-fold, but if the phosphorylation of Ser473 is combined with the mutation of Thr-308 to Asp, activity is increased 25-fold [15]. PKBα that has been partially activated by phosphorylation of Thr-308 or by the mutation of this residue to Asp does not become phosphorylated at Ser473 in vitro upon incubation with MgATP in the presence of PtdIns(3,4,5)P3 ([15], FIG. 5) indicating that Ser473 is unlikely to be an autophosphorylation event, catalysed by PKBα itself. Ser-473 can be phosphorylated in vitro by MAP kinase-activated protein kinase-2, but this enzyme cannot mediate the insulin or IGF1-induced phosphorylation of PKBα at Ser473 for reasons discussed in [15]. Since the insulin/IGF1-induced phosphorylation of Ser-473 is prevented by inhibitors of PtdIns 3-kinase, this residue may be phosphorylated by a distinct 3-phosphoinositide-dependent protein kinase (PDK2—FIG. 7). However, the Ser473 kinase does not appear to be the PtdIns(3,4,5) P3-dependent peak-1 activity from heparin-Sepharose (FIG. 2B), because this enzyme also phosphorylates PKB at Thr-308 (data not shown). The peak-1 may be a proteolytic fragment of peak-2 (or vice versa) or another isoform of PDK1. It is also possible that PtdIns(3,4,5)P3 /PtdIns(3,4)P2 activates the Ser-473 kinase indirectly. For example, the phosphorylation of Ser-473 may be dependent on the binding of PtdIns(3,4,5)P3 /PtdIns(3,4)P2 to the PH domain of PKB [18, 21] (but see below). Alternatively, the Ser-473 kinase may be activated by PDK1. The mechanism by which insulin induces the activation of PKBα is shown schematically in FIG. 7.

The activation of PDK1 by PtdIns(3,4,5)P3 is extremely specific, because only D-enantiomers of PtdIns(3,4,5)P3 are effective and many other PtdIns phospholipids are inactive. Although the enantiomeric configuration of the glycerol moiety is not important, the presence of one or more unsaturated fatty acids greatly influences the extent of activation of PDK1 by PtdIns(3,4,5)P3 analogues (FIG. 6). Since unsaturated fatty acids discourage tight packing of adjacent phospholipid molecules, it is possible that this arrangement allows for more efficient interaction between membrane-inserted PtdIns(3,4,5)P3 and its effectors, perhaps explaining for the first time the biological significance of the unusual fatty acid composition of inositol phospholipids.

PtdIns(3,4,5)P3 and/or PtdIns(3,4)P2 have no effect on the activity of PKBα under conditions where these inositol phospholipids activate PDK1 strongly (FIG. 6) consistent with our previous findings [18]. This observation, together with the finding that the activation of PKBα by insulin or IGF1 results from its phosphorylation at Thr-308 and Ser473 [15], appears to exclude direct activation of PKBα by 3-phosphoinositides as a mechanism for its activation in vivo. Our results disagree with recent reports which have claimed that PKBα is activated directly by PtdIns(3,4)P2 [19–21]. Contamination of PKBα preparations with PDK1 activity may explain this discrepancy; recall that the activation of phosphorylase kinase by cyclic AMP [22] was later shown to result from contamination with a separate cyclic AMP-dependent protein kinase [23]. It has also been reported that PKBα is inhibited by PtdIns(3,4,5)P3 [20,21], but none of the four PtdIns(3,4,5)P3 derivatives we tested inhibited the basal PKBα activity at all, while all four were capable of activating PDK1. It is possible that the synthetic PtdIns(3,4,5)P3 used in [20, 21] contains impurities that inhibit PKBα and or PDK1.

Although PKB is. not activated directly by PtdIns(3,4,5)P3 or PtdIns(3,4)P2, it does bind these inositol phospholipids with micromolar affinity [18, 21], via the N-terminal pleckstrin homology (PH) domain [18, 21]. In contrast, PKB binds PtdIns(4,5)P2 with a 10-fold lower affinity and does not bind to other inositol phospholipids tested [18, 21]. These findings raise several interesting possibilities. Firstly, the interaction of PtdIns(3,4,5)P3 and/or PtdIns(3,4)P2 with PKB may alter its conformation in such a way as to facilitate phosphorylation by PDK1 and the Ser-473 kinase. Secondly, the formation of PtdIns(3,4,5)P3 and/or PtdIns(3,4)P2 in the plasma membrane may recruit PKB to this membrane also facilitating its activation by PDK1 and the Ser-473 kinase. However, neither of these mechanisms appear to be essential for the activation of PKB in vivo, because a mutant lacking the PH domain can still be activated at least as well as wild-type PKB in response to insulin [24, 25]. Alternatively, recruitment of PKB to the plasma membrane could be a mechanism for facilitating the phosphorylation of membrane-bound PKB substrates. However, it should be noted that we purified PDK1 from the cytosol of skeletal muscle. It will clearly be important to examine whether PDK1 localises to the plasma membrane when cells are stimulated with agonists which trigger a rise in the concentration of PtdIns(3,4,5)P3 and PtdIns(3,4)P2.

EXAMPLE 2

Cloning of PDK1

We obtained the amino acid sequences of 9 peptide derived from PDK1 that we purified from rabbit skeletal muscle, these were:

LDHPFFVK(SEQ ID NO: 5);
ANSFVGTAQYVSPELL(SEQ ID NO: 3);
AGNEYLIFQK(SEQ ID NO: 4);
AHPFFESVTWENLHQQTPPK(SEQ ID NO: 11);
SGSNIEQYIHDLDSNSFELDL(SEQ ID NO: 12);
QAGGNPWHQFVENNLILK(SEQ ID NO: 13);
QLLLTEGPHLYYVDPVNK(SEQ ID NO: 14);
TFFVHTPNR(SEQ ID NO: 15);
YQSHPDAAVQ(SEQ ID NO: 16);

We then put these sequences through the BLAST ncbi database search on the Internet and we discovered that all of these 9 peptide sequences were encoded by 2 EST sequences. The information regarding these EST sequences available from the Internet is given in FIGS. 8 and 9. We then requested the ESTs from the UK HGMP Resource Centre, I.M.A.G.E. Consortium, Hinxton, Cambridge CB1 1SB, UK (a consortium part funded by the Medical Research Council).

We then determined the nucleotide sequences of the EST clones ourselves by sequencing both DNA strands of the ESTs. There were a number of errors in the EST sequences available on the Internet. From the data we obtained it is clear that the EST sequences represent two overlapping clones of PDK1.

Most of the open reading frame of PDK1 was derived by interogation of the dbest database at the National Centre for Biological Information. A full length cDNA clone for PDK1 was isolated by hybridisation screening of a cDNA library, in the vector λZAP, made from the human breast cancer cell line MCF7 (a gift of P. Mitchell, Institute of Cancer Research, Sutton, UK). The PDK1 probe for the screening was generated by RT-PCR with the primers CTGAGC-CAGTTTGGCTGC (SEQ ID NO: 17) and ACGTCCTGT-TAGGCGTGTGG (SEQ ID NO: 18) corresponding to nucleotide 1138–1567 of the PDK1 sequence, with MCF7 cDNA as template. DNA sequencing was carried out on an Applied Biosystems 373A DNA automatic sequencer using the Taq dye terminator cycle sequencing kit.

The nucleotide and amino acid sequences for PDK1 (SEQ ID NO: 2 and SEQ ID NO: 1, respectively) are shown in FIG. 10. The sequence encodes a 556 residue protein with a predicted molecular mass of 63.1 kDa. We expressed PDK1 protein with a Myc epitope Tag in 293 cells (see Examples below) and it migrates as a 68–70 kDa band, and PDK1 antibodies we have raised recognise a 69 kDa band in 293 cell lysates (data not shown). For this reason, and because the initiating methionine lies in a good Kozak consensus sequence, the sequence shown in FIG. 10 is likely to represent the whole of PDK1.

Polynucleotides containing a full length coding sequence for PDK1 are readily obtained by, for example, using suitable PCR primers based on the nucleotide sequence given in FIG. 10 and amplifying the PDK1 cDNA from a suitable cDNA library or from reverse-transcribed mRNA.

Also a polynucleotide containing a coding sequence for PDK1 is obtained by ligating appropriate portions of IMAGE clone 626511 and IMAGE clone 526583 following digestion with suitable restriction endonucleases or by using PCR-based strategies for joining appropriate aparts of IMAGE clone 526583 and IMAGE clone 626511.

It will be appreciated that a full length coding sequence for PDK1 can readily be obtained from a suitable cDNA library using the sequence information given in FIG. 10 to generate a probe and that the sequence of any clone obtained in this way can be determined using the Sanger dideoxy sequencing method.

The human ESTs encoding PDK1 were isolated from many different human tissues (Table A below) indicating that PDK1 is expressed ubiquitously. Interestingly, the nucleotide sequence of PDK1 possessed 100% identity to the partial sequence of a gene that has been mapped to a 700-kb region on Human Chromosome 16p13.3 close to the genes responsible for polycystic kidney disease type 1 and tuberous sclerosis type 2 disease [23]. This gene is known to be expressed as a large 8-kb transcript in heart, brain, placenta, lung, skeletal muscle, kidney and pancreas [23].

TABLE A

List of overlapping Expressed Sequence Tags in the database encoding for PDK1 gene. Accession numbers are from gene bank. The tissue is the tissue from which the EST was derived from.

| Accession Number | Tissue |
| --- | --- |
| AA186323 | HeLa cells |
| H97903 | melanocyte |
| AA018098 | retina |
| AA018097 | retina |
| AA019394 | retina |
| AA019393 | retina |
| N22904 | melanocyte |
| W94736 | fetal heart |
| EST51985 | gall bladder |
| N31292 | melanocyte |
| AA188174 | HeLa cells |
| AA100210 | colon |
| R84271 | retina |
| AA121994 | pancreas |

EXAMPLE 3

Alternative Cloning Strategy for PDK1

The 67 kDa band corresponding to PDK1 was cleaved with trypsin and the digest chromatographed on a Vydac C18 column to resolve the tryptic peptides. The sequences of the following three peptides were established:

1. ANSFVGTAQYVSPELL (SEQ ID NO: 3)
2. AGNEYLIFQK (SEQ ID NO: 4)
3. LDHPFFVK (SEQ ID NO: 5)

These peptides are homologous to sequences found in the catalytic domains of other protein kinases. Peptide 1 is homologous to a region of subdomain VIII, peptide 2 to a region of subdomain X and peptide 3 to a region of subdomain XI. These sequences are used to clone PDK1 using standard PCR-based strategies.

Polymerase chain reactions (PCR) are carried out using the following oligonucleotides coding the peptides 1 and 3 (or slight variations thereof; for example the position I may be inosine or various combinations of G, C, A and T):

5'TTTGT(G/T)GGIACIGCICA(A/G)TA(T/C)GT 3' (SEQ ID NO: 19)

coding for the part of peptide 1 shown in boldface type.

5' TTIAC(A/G)AA(A/G)AAIGG(A/G)TG(A/G)TC 3' (SEQ ID NO: 20)

coding for peptide 3.

The resulting PCR fragment contains the region coding for peptide 2 and is analysed by Southern blotting and hybridisation with the following oligonucleotide coding for peptide 2 (or slight variations thereof: for example the position I may be inosine or various combinations of G, C, A and T):

5' AA(T/C)GA(A/G)TA(T/C)(C/T)TIAT(T/C/A)TT(TC)CA(A/G)AA3' (SEQ ID NO: 21)

Positive PCR fragments are subcloned and used to screen skeletal muscle and other cDNA libraries to isolate a full length clone for PDK-1.

The full-length clone for PDK-1 is sequenced using the Sanger dideoxy method.

The rabbit PDK-1 cDNA may be obtained first and this is used to screen a human skeletal muscle cDNA library to isolate a full-length human PDK-1 cDNA. Molecular biology techniques used are essentially as described in Sambrook et al (1989) Molecular cloning, a laboratory manual, Cold Spring Harbor Laboratory Press, Cold Spring Harbor, N.Y.

EXAMPLE 4

Further Alternative Cloning Strategy for PDK1

Antibodies are raised against PDK1 purified as described in Example 1.

The antibodies are used to screen a λgt11 expression library made from cDNA copied from human or rabbit skeletal muscle mRNA.

Positive clones are identified and the insert sequenced by the Sanger method as in Example 2.

EXAMPLE 5

Expression of Human PDK1 and Activation of PKBα; Homology to Drosophila DSTPK61

In order to elucidate the role of PDK1 in vivo and to determine the mechanism by which it is regulated by PtdIns$(3,4,5)P_3$ and PtdIns$(3,4)P_2$ it was clearly useful to first determine the structure of this enzyme and the mechanism by which PtdIns$(3,4,5)P3$ /PtdIns$(3,4)P2$ stimulates PDK1 to phosphorylate PKB. In this and previous Examples, we describe the cloning, sequencing and expression of human PDK1, and demonstrate that the expressed enzyme activates PKBα in vitro in an identical manner to PDK1 purified from muscle. PDK1 also activates PKBα in cotransfection experiments and it also potentiated the phosphorylation of Thr308 induced by IGF1. Surprisingly, PDK1 was found to be structurally and functionally homologous to the Drosophila protein kinase DSTPK61, which has been implicated in the regulation of sexual development in Drosophila.

Materials and Methods

Materials

All phospholipids were obtained from the sources described previously [21]. Glutathione Sepharose, the pGEX-3 X expression vector and 1 ml heparin-Sepharose column (HiTrap) were purchased from Pharmacia (Milton Keynes, UK); monoclonal antibodies 12CA5 and 9E10 were from Boehringer Mannheim (Lewes, UK) and alkylated trypsin and the pSP72 cloning vector from Promega (Southampton, UK). GST-PKBα and sources of all other materials are described in [21]. The pCR 2.1-TOPO cloning vector was from Invitrogen (Leek, Netherlands).

Buffer solutions. Buffer A: 50 mM Tris/HCl pH 7.5, 1 mM EDTA 1 mM EGTA, 1% (by vol) Triton X-100, 1 mM sodium orthovanadate, 10 mM sodium β-glycerophosphate, 50 mM NaF, 5 mM sodium pyrophosphate, 1 μM microcystin-LR, 0.27 M sucrose, 1 mM benzamidine, 0.2 mM phenylmethylsulphonyl fluoride (PMSF), 10 μg/ml leupeptin, 0.1% (by vol) 2-mercaptoethanol. Buffer B: 50 mM Tris/H Cl pH 7.5, 0.1 mM EGTA, 0.03% (by vol) Brij-35, 0.27 M sucrose, 0.1% (by vol) 2-mercaptoethanol.

Preparation of DNA expression constructs encoding GST-PDK1, Myc-PDK1. Two overlapping human ESTs encoding PDK1 (GenBank accession numbers AA121994 and AA186323 corresponding to nucleotides 98 to 708 and 467 to 1811 of PDK1 (FIG. 1) were obtained from the I.M.A.G.E. consortium [42] and sequenced. The two sequences were joined together by an ScaI restriction enzyme digest of each EST clone, and the appropriate restriction fragments obtained from these digests were ligated to generate a plasmid containing a continuous PDK1 sequence from nucleotides 154 to 1670. This construct was used as a template for a PCR reaction to generate an N-terminal epitope-tagged Myc-PDK1 (amino acid residues 52–556) construct. This was achieved using the oligonucleotides GCGG<u>AGATCT</u>GCCACCATGGAGCAGAAGCT GATCTCTGAAGAGGACTTGGACGGCACT-GCAGCCGAGCCTCGG (SEQ ID NO: 22) and GCGGG GTACCTCACTGCACAGCGGCGTCCGGGTG (SEQ ID NO: 23) that incorporate a BglII site (underlined) and a KpnI site (double underlined). The resulting PCR fragment was subcloned into the BglII/KpnI sites of an pSP72 cloning vector, and the nucleotide sequence confirmed by DNA sequencing. The Myc-PDK1 coding sequence was subcloned from this vector as a BglII-KpnI fragment into the BamHI and KpnI sites of the eukaryotic expression vectors pEBG2T [43] in order to generate a construct for the expression of GST-PDK1 in 293 cells. The same fragment was ligated into the BglII and SalI sites of the vector pCMV5 [44] to generate a construct for the expression of Myc-PDK1 in 293 cells. The structure of each construct was verified by DNA sequencing, and plasmid DNA for transfection was purified using the Qiagen plasmid Mega kit according to the manufacturer's protocol.

N-terminal Myc epitope tagged PDK1 constructs encoding the full length protein (residues 1 to 556) and lacking the PH domain (residues 1 to 450) were generated by a PCR approach using the full length full length PDK1 cDNA isolated from the MCF7 library. This was achieved by using the 5' primer gcggagatctgccaccatggagcagaagctgatctctgaagaggacttggccaggaccaccagccagctgtatgacg (SEQ ID NO: 24) (for both the full length and ΔPH-PDK1 constructs) and the 3' primers gcggggtacctcactgcacagcg-gcgtccgggtg (SEQ ID NO: 23) (for full length PDK1) and gcggggtacctcagtgccaagggtttccgccagcctgctt (SEQ ID NO: 25(for the ΔPH-PDK1 construct). The resulting PCR fragments were cloned into the pCR 2. 1-TOPO vector and subsequently subcloned into the pEGB-2T vector as BglII-KpnI fragment and pCMV5 as an EcoRI-KpnI fragment. A full length catalytically inactive PDK1 construct in which Asp223 was changed to Ala was created by the PCR-based megaprimer strategy (Tao & Lee (1994) In: Griffm & Griffm (eds) PCR Technology: Current Innovations, CRC Press, Boca Raton, Fla., pp 69–83) and then subcloned into pCMV5 and pEBG-2T as described above. The structure of each construct was verified by DNA sequencing, and plasmid DNA for transfection was purified using the Qiagen plasmid Mega kit according to the manufacturer's protocol.

A bacterial expression vector for GST-DSTPK61 was prepared by ligating a EcoRI/EcoRV fragment of the Dstpk61 cDNA derived from pBluescriptSK into the EcoRI/ SalI sites of the pGEX-3 X expression vector.

Preparation of DNA expression constructs encoding GST-ΔPH-PKBα. A PCR based strategy was used to prepare a GST-ΔPH-PKBα (encoding residues 118479 PKBα) construct using as a template a full length human PKBα construct that was isolated from a human skeletal muscle cDNA library and subcloned into the pBluescriptSK vector. The GST-ΔPH-PKBα construct was obtained using the 5' primer cgggatccatggacttccggtcggctca (SEQ ID NO: 26) and 3' primer was the T7 oligonucleotide of pBluescriptSK vector. The resulting PCR fragment was cloned into pBluescriptSK as a BamHI-KpnI fragment, and subsequently into pEBG-2T as a BamHI-KpnI fragment.

Expression of GST-PDK1, GST-ΔPH-PDK1, GST-D223A-PDK1, GST-ΔPH-PKBα and GST-DSTPK61. Twenty 10 cm diameter dishes of human embryonic kidney 293 cells were cultured and each dish transfected with 20 μg of DNA encoding either GST-PDK1 (residues 52–556), GST-PDK1 (residues 1–556), GST-ΔPH-PDK1, GST-D223A-PDK1, or GST-ΔPH-PKBα using a modified calcium phosphate method [20]. 24 h after transfection, the cells were serum starved for 16 h and each dish of cells lysed in 1 ml of ice-cold Buffer A. The 20 lysates were pooled, centrifuged at 4° C. for 10 min at 13,000×g and the supernatant incubated for 60 min on a rotating platform with 1 ml of glutathione-Sepharose previously equilibrated in Buffer A. The suspension was centrifuged for 1 min at 3000×g, the beads washed three times with 10 ml of Buffer A containing 0.5 M NaCl, and then a further 10 times with 10 ml of Buffer B to ensure complete removal of all the Triton X-100 which interferes with the activation of GST-PKBα by PDK1 [21]. GST-PDK1α was eluted from the resin at ambient temperature with three 1 ml portions of Buffer B containing 20 mM glutathione pH 8.0. The combined eluates (0.8 mg/ml protein) were divided into aliquots, snap frozen in liquid nitrogen, and stored at −80° C. Between 0.5 and 2.0 mg of each GST-fusion protein was obtained and was more than 90% homogeneous as judged by SDS polyacrylamide gel electrophoresis.

E. coli transformed with an expression plasmid encoding GST-DSTPK61 were grown at 37° C. in LB medium to an absorbance of 0.6 at 600 nm. Isopropyl-β-D-thiopyranoside was added to 30 μM and the bacteria were incubated for 16 h at 25° C. before centrifuging for 10 min at 4000×g. The bacteria were resuspended in 15 ml of Buffer A and lysed by sonication for 4 min on ice. The suspension was centrifuged for 30 min at 30 000×g and the GST-DSTPK61 was purified by affinity chromatography on 1 ml of glutathione-Sepharose as described above for GST-PDK1. The GST-DSTPK61 derived from this (0.35 mg/ml) was divided into aliquots, snap frozen in liquid nitrogen and stored at −80° C.

Assay of GST-PDK1 and GST-DSTPK61 activity. GST-PDK1 and GST-DSTPK61 were diluted appropriately in Buffer B containing 1 mg/ml bovine serum albumin, and assayed for their ability to activate and phosphorylate GST-PKBα [21]. One unit of PDK1 activity was defined as that amount required to increase the basal activity of GST-PKBα by 1 unit of activity in one min. One unit of GST-PKBα activity was that amount of enzyme required to catalyse the phosphorylation of 1 nmol of the peptide RPRAATF (SEQ ID NO: 9) in 1 min in an assay containing 0.1 mM RPRAATF (SEQ ID NO: 9) [45]). In order to ensure that the assay was linear with respect to time the concentration of GST-PDK1 or GST-DSTPK61 was below 2 U/ml. At this concentration the level of phosphorylation of PBKα was <0.4 mol phosphate per mol protein in the 30 min assay.

Transfection of 293 cells with HA-tagged PBKα and Myc-PDK1. Human embryonic kidney 293 cells were cultured on 10 cm diameter dishes and transfected with 2 μ/ml pCMV5 DNA constructs encoding for HA-PKBα or HA-PKBα plus Myc-PDK1[20]. After 24 h the cells were deprived of serum for a further 16 h and then stimulated for 10 min with either 100 ng/ml IGF1 or Buffer. The cells were lysed in 1.0 ml of ice-cold Buffer A, the lysate centrifuged at 4° C. for 10 min at 13,000×g and HA-PKBα immunoprecipitated from aliquots of the supernatant (10 μg protein) [20] and assayed for PKBα with the peptide RPRAATF (SEQ ID NO: 9) [45] as described previously [20]. $^{32}$P-labelling of 293 cells transfected with HA-PKBα or Myc-PDK1. This was carried out essentially as described previously [20]. Briefly, 293 cells were transfected with HA-PKBα, or with HA-PKBα plus Myc-PDK1, washed with phosphate free DMEM, incubated for 4 h with [$^{32}$P]-orthophosphate (1 mCi/mi), then stimulated with IGF1 (50 ng/ml) for 5 min. The cells were lysed, and the HA-PKBα immunoprecipitated (using 10 μg of 12CAS antibody per 10 cm dish of cells) or the Myc-PDK1 immunoprecipitated (using 10 μg of 9E10 antibody per 10 cm dish of cells). The immunoprecipitated protein was alkylated with 2-vinylpyridine, subjected to SDS/polyacrylamide gel electrophoresis, digested with trypsin and analysed by chromatography on a $C_{18}$ column (Alessi et al (1996) *EMBO J.* 15, 6541–6551).

Results

PDK1 is a human homologue of the Drosophila DSTPK61 protein kinase. The catalytic domain of PDK1 spans residues 83–342 (FIG. 10) and contains all of the classical kinase subdomains I-XI [241]. It is most similar to the subfamily of protein kinases that include PKA (39% identity to the catalytic domain), PKC (35% identity to the ζ isoform) and PKB (35% identity). The PDK1 catalytic domain was even more similar to two yeast protein kinases of unknown function. The catalytic domain was 53% identical to the *S. pombe* protein kinase with GenBank accession number 1431588 and 48% identical to the *S. cerevisiae* protein kinase with accession number 1078290. However, there was no homology between PDK1 and these yeast protein kinases outside of the catalytic domain. In contrast, the Drosophila protein kinase named Drosophila Serine/Threonine Protein Kinase-61 (DSTPK61, accession number Y07908 ref 22) was not only 54% identical to PDK1 in the catalytic domain, but was very similar in the non catalytic C-terminal domain (FIG. 11). This homology was most striking between residues 450 and 550 of PDK1 where the identity to DSTPK61 was 61% (79% similarity). These observations suggested that DSTPK61 might be a Drosophila homologue of PDK1. However, DSTPK61 contains a 60 residue C-terminal C-terminal extension not found in PDK1 and there is little homology between the N-terminal 70 residues of PDK1 and N-terminal 150 residues of DSTPK61 (FIG. 11). PDK1 also lacks the polyglutamine insertion sequence present near the N-terminus of DSTPK61 (residues 120–150) and a further polyacidic insertion located between subdomains VII and VIII (residues 312 to 370) of the kinase domain (FIG. 11). The physiological role of DSTPK61 will be considered further under Discussion.

PDK1 and DSTPK61 possess a C-terminal Plecktrin Homology domain. The high level of sequence conservation between PDK1 and STK61, from residues 450–550 of PDK1 (FIG. 11), suggested that this region is likely to have an important function. Inspection of these sequences indicated that these are likely to form part of a Plecktrin Homology (PH) domain. These domains of ~100 residues are found in over 70 other proteins and are predicted to fold into a similar 3-dimensional structures and may mediate protein-lipid, protein-protein interactions, or both [25,26]. We have performed sequence alignment of residues 450–550 in both PDK1 and STK61, together with sequences from PH domains of determined tertiary sructure, plecktrin, spectrin, dynamin, and phospholipase C-δ and also with 71 other known PH domain sequences (data not shown). Although the percentage identity is poor between PH domains in general there are certain positions that show high levels of residue type conservation. For PDK1 and DSTPK a single position (Tryptophan, position 113, position Trp-535 of PDK1) shows complete identity throughout the domain family, however there are also many similar amino acids at defined regions of the PH domain) (FIG. 17). Secondary structure predictions also indicated that residues 450–530 of PDK1 (positions 1–80) are likely to contain regions of β-sheet, while the residues between 531–550 (positions 80–100) are likely to form an extended α-helix, a prediction that is consistent with the known structures of other PH domains [25,261].

Expression of GST-PDK1 and GST-DSTPK61. Residues 52–556 of PDK1 were expressed in human embryonic kidney 293 cells and residues 1–752 of DSTPK61 in *E. coli* as fusion proteins with glutathione S-transferase (GST) at the N-terminus (hereafter termed GST-PDK1 and GST-DSTPK61), and both were purified on glutathione-Sepharose. The GST-PDK1 preparation showed two bands with apparent molecular masses of 87 and 85 kDa (FIG. 18, Lane 1) and 2 mg of GST-PDK1 purified protein was obtained from 20 (10 cm diameter) dishes of cells. The GST-DSTPK61 preparation showed a diffuse band at the expected molecular mass (105 kDa) together with a number of minor degradation products (FIG. 18, Lane 2). 0.35 mg of GST-DSTPK61 were obtained from 0.5 litres of bacterial culture.

GST-PDK1 and GST-DSTPK61 activate and phosphorylate PKBα in a PtdIns(3,4,5)$P_3$ or PtdIns(3,4)$P_2$ dependent manner. GST-PDK1 and GST-DSTPK61 both activated and phosphorylated GST-PKBα in the presence of a vesicle background containing phosphatidylcholine (PtdCho) and phosphatidylserine (PtdSer) provided that PtdIns(3,4,5)$P_3$ or PtdIns(3,4)$P_2$ were included. The extent of activation of GST-PKBα correlated with the extent of phosphorylation (FIG. 12), and no activation or phosphorylation occurred if PtdIns(3,4,5)$P_3$ or PtdIns(3,4)$P_2$ were replaced by either PtdIns(4,5)$P_2$ or PtdIns 3-P (FIG. 12). Identical results were obtained using purified PDK1 from rabbit skeletal muscle and full length GST-PDK1 (residues 1–556) expressed in 293 cells ([21] and data not shown). A catalytically inactive GST-PDK1 mutant in which Asp223 was changed to Ala did not phosphorylate or active GST-PKBα in the presence of PtdCho/PtdSer lipid vesicles containing PtdIns(3,4,5)P3 (data not shown). The specific activities of GST-PDK1 (residues 52 to 556, 78 000 U/mg) and GST-PDK1 (residues 1 to 556, 89 000 U/mg) toward GST-PKBα in the presence of PtdIns (3,4,5)P3 were similar to PDK1 purified from rabbit skeletal muscle (100 000 U/mg), being over 200 times higher than that of bacterially expressed GST-DST PK61 (280 U/mg). Further work is needed to establish whether this difference is caused by misfolding of DSTPK61 or lack of an important post-translational modification when it is expressed in *E. coli*, or whether DSTPK61 does not recognise human PKBα as well as human PDK1.

Some activation and phosphorylation of GST-PKBα was obtained using very high concentrations of GST-PDK1 or GST-DSTPK61 in the absence of PtdIns(3,4,5)$P_3$ or PtdIns (3,4)$P_2$. However, the activity of PDK1 was enhanced about 1000-fold in the presence of these inositol phospholipids. In the presence of PtdIns(3,4,5)$P_3$ lipids and at high GST-PDK1 and GST-DSTPK61 concentrations, the phosphorylation of GST-PKBα reached 0.75 mol phosphate per mol protein and was paralleled by a 35 fold increase in activity. This was similar to the maximal activation of GST-PKBα obtained using PDK1 from rabbit skeletal muscle [21].

Expressed PDK1 and DSTPK61 phosphorylate PKBα at Thr308. $^{32}$P-labelled GST-PKBα that had been maximally phosphorylated with either GST-PDK1 (FIG. 13A) or GST-DSTPK61 (FIG. 13B), was digested with trypsin and chromatographed on a $C_{18}$ column. One major $^{32}$P-labelled peptide was obtained in each case. This peptide eluted at 25% acetonitrile at the same position as the $^{32}$P-labelled tryptic phosphopeptide containing Thr308 [20,21], and contained phosphothreonine and, when subjected to solid phase sequencing, $^{32}$P-radioactivity was released after the first cycle of Edman degradation, confirming that this peptide is indeed that of PKBα phosphorylated at Thr308 (data not shown).

PKBα is activated by cotransfection with PDK1 in 293 cells and phosphorylated at Thr308. In order to determine if PDK1 was capable of activating PKBα in a cellular context, we transfected a haemaglutinnin epitope-tagged PKBα (HA-PKBα) into 293 cells, either alone or together with Myc-epitope tagged PDK1 (Myc-PDK1). As reported previously, HA-PKBα possessed a low basal activity when transfected alone into 293 cells, which was increased 40-fold after stimulation with IGF1 (FIG. 14, [20]). However, when 293 cells were transfected with both HA-PKBα and Myc-PDK1, the activity of HA-PKBα was increased 20-fold in unstimulated cells, and 70-fold after stimulation with IGF-1 (FIG. 14). When 293 cells were transfected with HA-PKBα and a catalytically inactive mutant of PDK1 (Myc-D223A-PDK1), HA-PKBα was not activated significantly (FIG. 14).

Figure 15A:
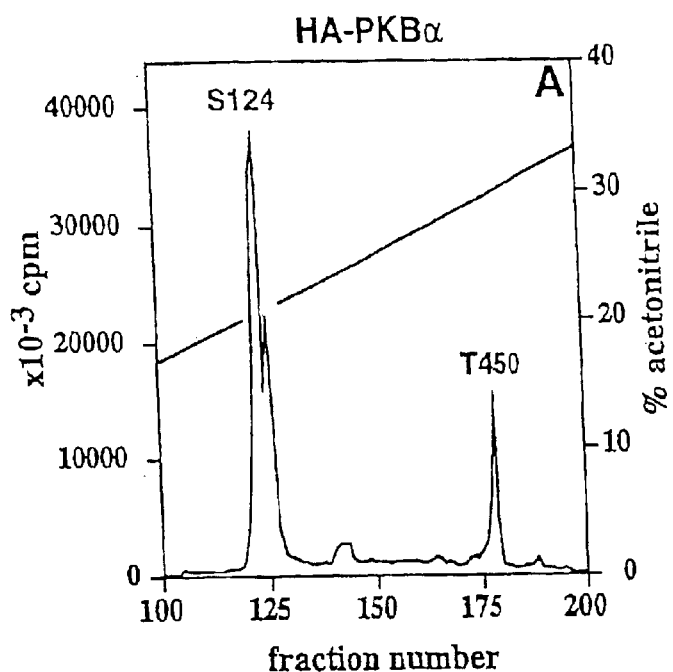
Figure 15C:
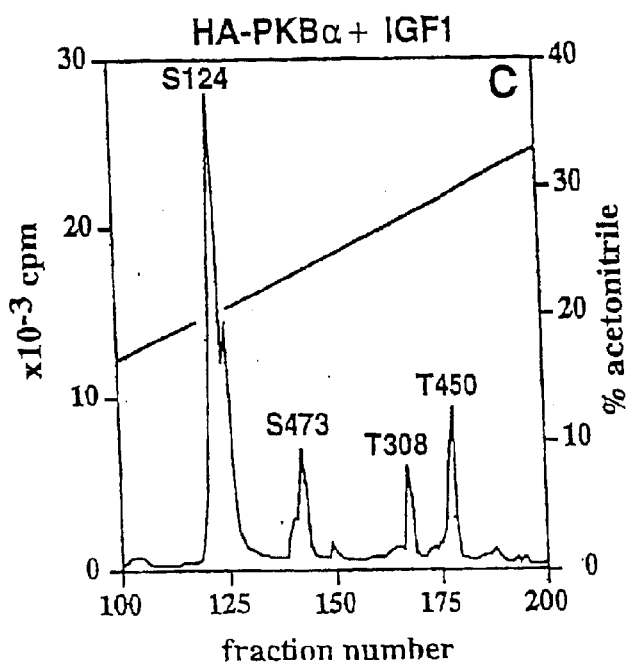
Figure 15B:
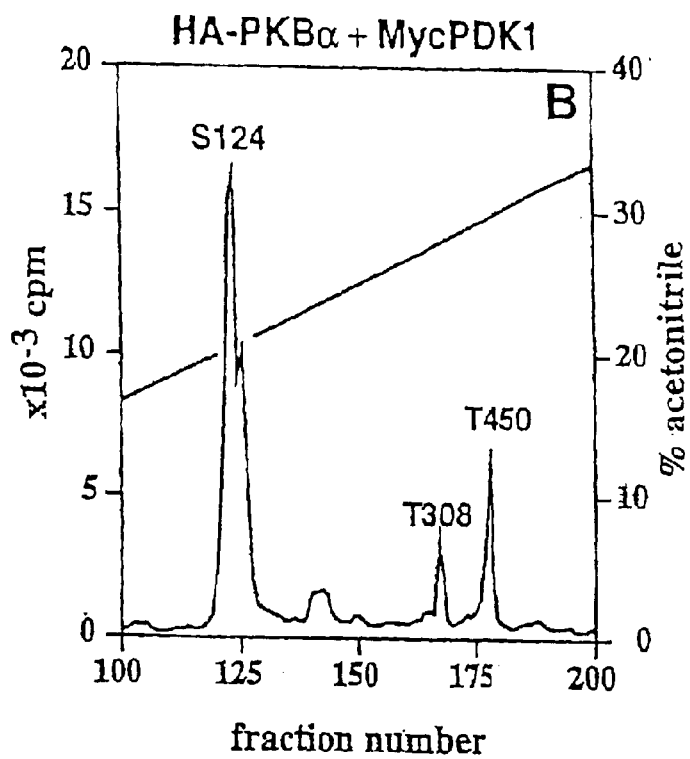
Figure 15D:
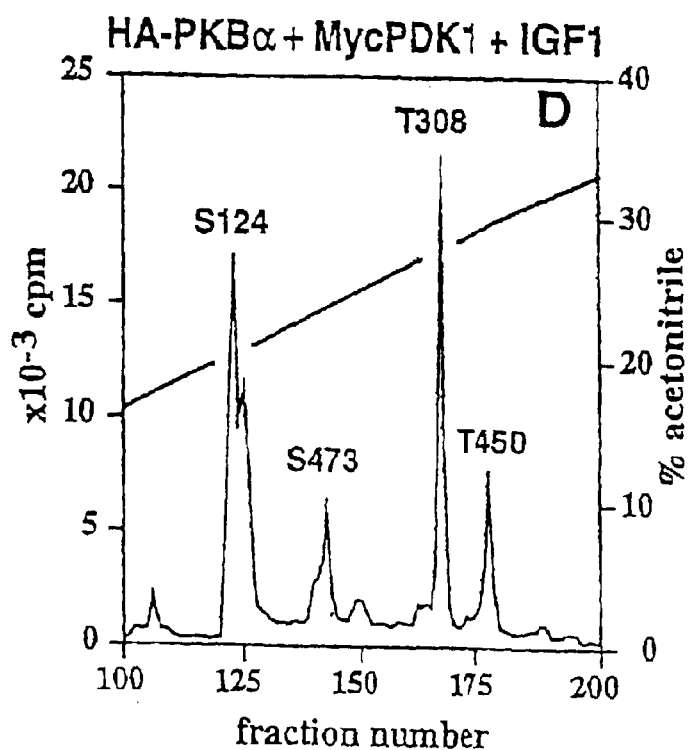

In order to establish the mechanism by which overexpression of PDK1 in 293 cells induced the activation of PKBα the cells were incubated with $^{32}$P-phosphate, stimulated with buffer or IGF1 and $^{32}$P-labelled HA-PKBα was immunoprecipitated from the lysates. After digestion with trypsin, the resulting peptides were analysed by C$_{18}$ chromatography (FIG. 15). As observed previously HA-PKBα is phosphorylated at Ser-124 and Thr-450 in unstimulated cells, and IGF1 stimulation induces the phosphorylation of Thr308 and Ser473 (FIGS. 15A and 15C). In contrast, when cotransfected with PDK1, HA-PKBα became partially phosphorylated at Thr308 in unstimulated 293 cells, to a level that was 70% of that observed in IGF1-stimulated cells transfected with HA-PKBα alone. This phosphorylation of Thr308 was increased a further 2-fold in response to IGF1 (FIG. 15). Importantly, cotransfection of Myc-PDK1 with HA-PKBα did not induce phosphorylation of HA-PKBα at Ser473 in unstimulated cells, nor did it potentiate the level of Ser473 phosphorylation following IGF1 stimulation (FIG. 15).

Role of the PH domain in the activation of PKBα by PDK1. A mutant. GST-PKBα mutant lacking the PH domain (GST-ΔPH-PKBα, residues 118–479) possessed a 3-fold higher basal activity than that of full length wild-type GST-PKBα was activated (FIG. 16A) and phosphorylated (data not shown) by PDK1 in a PtdIns(3,4,5)P3 independent manner. However, the rate of activation was reduced about 20-fold compared to wild-type GST-PKBα (FIG. 16A). PDK1 purified from rabbit skeletal muscle extracts also activated and phosphorylated GST-ΔPH-PKBα in a PtdIns (3,4,5)P3 independent manner (data not shown).

A PDK1 mutant lacking the putative C-terminal PH domain was expressed as a GST-fusion protein in 293 cells (GST-ΔPH-PDK1, residues 1–450). We found that this form of PDK1 was still able to activate GST-PKBα in a PtdIns (3,4,5)P3-dependent manner, but the rate of activation was reduced about 30-fold compared to full length wild-type GST-PDK1 (FIG. 16B). As observed with PDK1 purified from rabbit skeletal muscle (see Example 1) or full length GST-PDK1 (data not shown), GST-ΔPH-PDK1 was activated more effectively by the D-enantiomer of sn-1-stearoyl, 2-arachidonyl PtdIns(3,4,5)P3 than by the D-enantiomer of sn-1,2-dipalmitoyl D-PtdIns(3,4,5)P3, and no activation was induced by the L-enantiomer of sn-1-stearoyl, 2-arachidonyl PtdIns(3,4,5)P3 (FIG. 9B). In contrast sn-1,2-dipalmitoyl D-PtdIns(3,4)P2 was very poor at inducing the activation of GST-PKBα by GST-ΔPH-PDK1 (FIG. 9B) under conditions where this lipid was as effective as sn-1,2-dipalmitoyl D-PtdIns(3,4,5)P3 at stimulating GST-PKBα activation by either full length GST-PDK1 (data not shown) or PDK1 purified from rabbit skeletal muscle (see Example 1). PDK1 is not activated or phosphorylated by IGF1. 293 cells were serum starved for 16 h, stimulated with IGF1 lysed and the endogenous PDK1 activity present in the cell lysates was determined after chromatography on heparin-Sepharose (see Methods). IGF1 stimulation of cells for up to 10 min did not result in any activation or inhibition of PDK1 activity (data not shown).

In order to see if IGF1 stimulation was inducing the phosphorylation of PDK1,293 cells were transfected with Myc-PDK1 (encoding residues 52 to 556), incubated with $^{32}$P-phosphate, stimulated with buffer or IGF1 for 5 min and $^{32}$P-labelled Myc-PDK1 was immunoprecipitated from the lysates. After digestion with trypsin, the resulting peptides were analysed by C$_{18}$ chromatography. These experiments demonstrate that PDK1 is phosphorylated at four tryptic peptides (only on serine residues) in unstimulated cells and that IGF1 does not alter the phosphorylation of any of these peptides (data not shown). Treatment of PDK1 purified from rabbit skeletal muscle with high concentrations of the serine/threonine-specific protein phosphatase 2A and protein tyrosine phosphatase 1B also had no effect on activity (data not shown). One of the in vivo phosphorylation sites on PDK1 was identified as Ser-241 which lies in the equivalent position to Thr308 of PKB in the kinase domain.

Discussion

PDK1 purified 500,000-fold from skeletal muscle [21] contains three proteins with apparent molecular masses of 85 kDa, 67–69 kDa and 45 kDa, and in this Example we established that the 67–69 kDa component is PDK1, and is likely to be a monomeric protein since it migrates with an apparent molecular mass of 70 kDa on gel filtration (data not shown). When cloned and expressed in 293 cells, this protein activated PKBα and induced its phosphorylation at Thr308, activation and phosphorylation both being dependent on PtdIns(3,4,5)P$_3$ or PtdIns(3,4)P$_2$. PDK1 also activated PKBα in cotransfection experiments and potentiated the phosphorylation of Thr308 by IGF1. These observations and the finding that, like PKB, the mRNA encoding PDK1 is expressed in every tissue examined (Table A) are consistent with the notion that PDK1 lies "upstream" of PKB in vivo.

PKBα becomes phosphorylated at Ser473 in vivo, as well as at Thr308, in response to insulin or IGF1. Moreover the phosphorylation of Ser473 is essential for the full activation of PKBα and, like the phosphorylation of Thr308, is prevented by wortmannin [201]. Importantly, PKBα did not become phosphorylated at Ser473 when cotransfected with PDK1, and nor did transfection with PDK1 affect the level of Ser473 phosphorylation after stimulation by IGF1. These experiments demonstrate that the protein kinase which phosphorylaes PKBα at Ser473 is not activated by PDK1, that phosphorylation of T308 of PKBα in a cell does not cause PKBα to autophosphorylate at Ser-473, and that the requirement for PtdIns(3,4,5)P$_3$/PtdIns(3,4) P$_2$ to trigger the phosphorylation of Ser473 is conferred by a different mechanism.

It is of interest that PDK1 lies in the same subfamily of protein kinase as PKB. Moreover, like PKB, it also contains a PH domain although, in contrast to PKB, this is located C-terminal to the catalytic domain [13]. The PH domain in PKB is capable of binding PtdIns(3,4,5)P$_3$ and PtdIns(3,4)P$_2$ at micromolar concentrations [27,28], which may facilitate its translocation to the plasma membrane that occurs in response to IGF1 [29] or interleukin-2 stimulation of EL2-IL-2 cells [30] to form a signalling complex. However, the finding presented in this paper that PDK1 is not activated by IGF1, and that a mutant of PKBα lacking the PH domain is activated and phosphorylated independently of PtdIns(3,4,5)P3 (FIG. 16A), demonstrates that the PtdIns(3,4,5)P3-induced activation of PKBα by PDK1 is substrate directed, at least in part. It is possible that the binding of PtdIns(3,4,5)P3 to the PH domain of PKBα, alters the conformation of PKBα so that Thr308 becomes accessible for phosphorylation by PDK1. Consistent with this model, deletion of the PH domain of PDK1 resulted in an enzyme that is still able to activate and phosphorylate PKBα in a PtdIns(3,4,5)P3 dependent manner (FIG. 16B).

However, the rate of activation of PKBα by PDK1 is reduced 30-fold when the PH domain of PDK1 is deleted. Thus it remains possible that the PH domain of PDK1 binds PtdIns(3,4,5)P3 and that this greatly enhances the rate of activation of PKBα. PtdIns(3,4,5)P3 can only stimulate the activation of PKBα by PDK1 when it is presented in lipid vesicles containing phosphatidyl choline and phosphatidyl serine (Example 1), and a PDK1 mutant lacking the PH domain may not be able to interact with lipids and hence be unable to penetrate these vesicles efficiently. This may account for the greatly reduced rate at which PDK1 lacking the PH domain activates PKBα. PKBα lacking the PH domain is also presumably unable to penetrate lipid vesicles and this may explain why this mutant is phosphorylated at a 20-fold lower rate by GST-PDK1 than full length PKBα (FIG. 16A).

Although PKBα is activated by cotransfection with PDK1 in 293 cells, the overexpression of PDK1 does not potentiate the activation of PKBα by IGF1 (FIG. 14). The reason is that the activation of PKBα also requires phosphorylation of Ser473, and phosphorylation of Thr308 and Ser473 have synergistic effects on activity (Alessi et al (1996) *EMBO J.* 15, 6541–6551). An important finding made in the present study is that PKBα does not become phosphorylated at Ser473 when cotransfected with PDK1, and nor does transfection with PDK1 affect the level of Ser473 phosphorylation attained after stimulation with IFG1. These experiments demonstrate that the protein kinase which phosphorylates PKBα at Ser473 is not activated by PDK1, and that phosphorylation of PKBα at Thr308 in a cellular context does not cause PKBα to autophosphorylate at Ser473. Like the phosphorylation of Thr308, Ser473 phosphorylation is prevented by incubating cells with wortmannin prior to stimulation with insulin or IGF1. It will be interesting to know whether the Ser473 kinase is activated by PtdIns(3,4,5)P3 or whether the binding of PtdIns(3,4,5)P3 to PKBα alters its conformation to permit phosphorylation by the Ser473 kinase. PDK1 was found to be homologous to DSTPK61 a Drosophilia protein kinase which is involved in the regulation of sex differentiation, oogenesis and spermatogenesis of the fruit fly [22]. The identity between PDK1 and DSTPK1 was 54% in the catalytic domain, but even greater (61% identity) in the putative PH domain (FIG. 11), further suggesting an important functional role for the PH domain of PDK1. DSTPK61 expressed in *E.coli* also activated human PKBα and phosphorylated it specifically at Thr308 in a PtdIns(3,4,5)P$_3$/PtdIns(3,4)P$_2$-dependent manner (FIG. 12). These findings indicate that DSTPK61 is a Drosophila homologue of PDK1 and suggest that one of its roles may be to activate the Drosophila homologue of PKB (termed DPKB) that was identified several years agao [31,32]. Although it is not yet known what the physiological roles of DSTPK1 are in flies the findings presented in this paper suggest that DPKB may lie downstream of DSTPK in signalling pathways regulating sex differentiation and oogenesis [22]. Since PtdIns 3-kinases are known to play a major role in the activation of PKB in mammalian cells [4–6 and 31] it is likely that a Drosophila phosphoinositide 3-kinase (PtdIns 3-kinase) also plays an important role in the activation of DPKB. Again very little is known about the role of PtdIns 3 kinase in flies [33]. Only one study has been published to date to address this issue in which a Drosophila PtdIns 3-kinase catalytic subunit termed Dpi110 has been overexpessed in the wing and eye imaginal discs of Drosophila, in a normal, a constitutively active and a dominant negative form [34]. The results of these studies showed that PtdIns 3-kinase is likely to play a role in regulating cell growth [34]. Interestingly, loss of function mutations in the Drosophila homologue of the insulin receptor, Inr also inhibited cell growth in imaginal discs and resulted in much smaller than wild type flies [35]. Taken together these results suggest that Drosophila PtdIns 3-kinases might be important targets of the insulin receptor, perhaps by acting through DPKB may regulate cell growth.

The DSTPK61 gene is differentially spliced in male and female Drosophila [22]. This generates many different transcripts that all have the same open reading frame, and therefore produce the same protein, but differ significantly in their 5' and 3' untranslated regions. This is likely to result in different levels of expression of the DSTPK61 protein in male and female Drosophila [22]. In view of the role of PKB in regulating apoptosis in mammalian cells (see introduction) it is possible that the function of DSTPK61 during oogenesis, spermatogenesis and in female adults in relation to sex-determinants might be related to cell survival or cell death decisions. One could imagine the low level of the non-sex specific transcript of DSTPK61 being responsible for general growth function consistent with the role of overexpression of Dp110 in cells [34] and the specifically spliced forms seen in female carcasses and ovaries and male testes being controlled translationally leading to the generation of high levels of protein at specific times. It should be remembered that the extent and duration of activation of the MAP kinase cascade is critical in determining whether a signal induces the proliferation of PC12 cells or their differentiation to a sympathetic neurone like phenotype [36,37]. Similarly, different levels of expression of DSTPK611 are likely to affect the extent and duration of activation of PKB in vivo and hence may determine the precise function of this kinase cascade. There are two signalling pathways involved in sex differentiation where such a situation may operate. The first involves the development of a specific adult male muscle in the abdomen required for holding the female fly during mating [38]. This muscle only develops in males in response to an unknown signal generated by adjacent nerve cells. It is likely that a signalling pathway which causes muscle cells in that region of the female fly to apoptose, whereas in male flies the growth of these muscle cells is promoted [38]. The second pathway involves an unknown signalling mechanism that operates between the somatic cells and germ cells in the male and female gonads in which a signal derived from the somatic cells initiates a signalling pathway that promotes cell survival of germ-line cells and induces these to differentiate into sperm and oocytes [39,40]). The mediators of both of these signalling pathways are at present unknown but, in light of the findings presented in this paper it is possible that a signalling pathway may operate that the unknown signals lead to the activation of PtdIns 3-kinase, DSTPK and then DPKB and the role of this pathway could be to mediate cell survival by inhibiting apoptosis. To understand the function of these signalling pathways future work will have to concentrate in obtaining mutants of the Drosophila DSTPK61, PKB and PtdIns 3-kinase genes, as well as identifying the specific signals that switch on these pathways. It would be of considerable interest to compare the effects of expressing constitutively active and domainant negative forms of Inr, Dp110, DSTPK61 and DPKB during oogenesis, spermatogenesis and sex-specific muscle differentiation.

SUMMARY

Background. The activation of protein kinase B (PKB, also known as c-Akt) is triggered within minutes of cells being stimulated with insulin or growth factors and results from its phosphorylation at Thr308 and Ser473. The activation of PKB and its phosphorylation at both residues are prevented by inhibitors of phosphoinositide 3-kinase, and we recently identified and purified a protein kinase that phosphorylates PKB at Thr308. This enzyme only phosphorylated PKB in the presence of lipid vesicles containing phosphatidylinositol 3,4,5-trisphosphate [PtdIns(3,4,5)$P_3$] or phosphatidylinositol 3,2-bisphosphate [PtdIns(3,4)$P_2$] and was therefore termed PtdIns(3,4,5)$P_3$-dependent protein kinase-1 (PDK1).

Results. We have cloned and sequenced human PDK1. The 556 residue, 63.1 kDa enzyme comprises a catalytic domain (residues 83–344) that is most similar to the subfamily of protein kinases that include PKA, PKB and PKC, and possesses a C-terminal pleckstri homology (PH) domain (residues 450–550). The gene encoding PDK1 is located on human chromosome 16p13.3 and is ubiquitously expressed in human tissues. Human PDK1 is highly homologous to the Drosophila protein kinase DSTPK61, which has been implicated in the regulation of sex differentiation, oogenesis and spermatogenesis in the fly, with 54% identity between the catalytic domains and 61% identity between the PH domains. GST-PDK1 expressed in 293 cells and GST-DSTPK61 expressed in *E. coli* were purified to homogeneity by chromatography on glutathione-Sepharose and their properties were found to be indistinguishable from PDK1 isolated from rabbit skeletal muscle. In the presence of lipid vesicles containing PtdIns(3,4,5)$P_3$ or PtdIns(3,4)$P_2$, but not PtdIns(4,5)$P_2$ or PtdIns(3)P, GST-PDK1 and GST-DSTPK61 both phosphorylated GST-PKBα stoichiometrically at Thr308 and increased its activity 35-fold in vitro. Myc-epitope-tagged human PDK1 also activated HA-tagged PKBα 20-fold in cotransfection experiments in 293 cells, and potentiated the IGF1-induced phosphorylation of HA-tagged PKBα at Thr308.

Overexpression of PDK1 in unstimulated 293 cells resulted in a 20-fold activation of PKBα, and potentiated the IGF1-induced phosphorylation of PKBα at Thr308. Experiments in which the PH domains of either PDK1 or PKBα were deleted indicated that the binding of PtdIns(3,4,5)P3 or PtdIns(3,4)P2 to PKBα is required for phosphorylation and activation by PDK1. IGF1 stimulation of 293 cells did not affect the activity or phosphorylation state of PDK1.

Conclusions. PDK1 is likely to mediate the activation of PKB by insulin or growth factors. DSTPK61 is a Drosophila homologue of PDK1, suggesting that PtdIns(3,4,5)$P_3$ and/or PtdIns(3,4)$P_2$ are likely to play as yet unidentified roles in sex differentiation in this organism. The effect of PtdIns(3, 4,5)P3 /PtdIns(3,4)P2 in the activation of PKBα is at least partly substrate directed.

References for Examples 2 and 5 and FIGS. 11 to 15

Coffer, P. J. and Woodgett, J. R. (1991) *Eur. J. Biochem.* 201, 475–481.

2. Jones, P. F. et al (1991) *Proc. Natl. Acad. Sci. USA* 88, 4171–4175.
3. Belacossa, A. et al (1991) *Science* 254, 244–247.
4. Franke, T. F. et al (1995) *Cell* 81, 727–736.
5. Burgering, B. M. T. and Coffer, P. J. (1995) *Nature* 376, 599–602.
6. Kohn, A. D. et al (1995) *EMBO, J.* 14, 42884295.
7. Cheng, J. Q. et al (1992) *Proc. Natl. Acad. Sci. USA* 89, 9267–9271.
8. Cheng, J. Q. et al (1996) *Proc. Natl. Acad. Sci. USA* 93, 3636–3641.
9. Kulik, G. et al (1997) *Mol. Cell. Biol.* 17, 1595–1606.
10. Dudek, H. et al (1997) *Science* 275, 661–665.
11. Kauffmann-Zeh et al (1997) *Nature* 385, 544–548.
12. Khwaja, A. et al *EMBO, J.* 16, 2783–2793.
13. Marte, B. M. and Downward, J. (1997) *Trends Biochem. Sci.* (In press).
14. Cross, D. A. E. et al (1995) *Nature* 378, 785–789.
15. Welsh, G. I. et al (1994) *Biochem. J.* 303, 15–20.
16. Cohen, P. et al *FEBS Lett.* (In press).
17. Lefebvre, V. et al (1996) *J. Biol. Chem.* 271, 22289–22292.
18. Deprez, J. et al (1997) *J. Biol. Chem.* (In press).
19. Kohn, A. D. et al (1996) *J. Biol. Chem.* 271, 31372–31378.
20. Alessi, D. R. et al (1996a) *EMBO, J.* 15, 6541–6551.
21. Alessi, D. R. et al (1997) *Curr. Biol.* 7, 261–269.
22. MacDougall, C. N. et al (1997) "A novel serine/threonine kinase gene (dstpk61) encoding sex-specific transcripts in Drosophila melanogaster" (Submitted).
23. Burn, T. C. et al (1996) *Genome Res.* 6, 525–537.
24. Hanks, S. K. et al (1988) *Science* 241, 42–52.
25. Gibson, T. J. et al (1994) *Trends Biochem. Sci.* 19, 349–353.
26. Shaw, G. (1996) *Bioessays* 18, 35–46.
27. James, S. R. et al (1996) *Biochem. J.* 315, 709–713.
28. Frech, M. et al (1996) *J. Biol. Chem.* 272, 8474–8478.
29. Ahmed, N. N. et al (1997) *Proc. Natl. Acad. Sci. USA* 94, 3627–3632.
30. Andjelkovic, M. et al (1997) "Membrane targeting activates protein kinase B through a phosphoinositide 3-kinase phosphorylation on Thr308 and Ser473" (Manuscript submitted).
31. Franke, T. F. et al (1994) *Oncogene* 9, 141–148.
32. Andjelkovic, M. et al (1995) *J. Biol. Chem.* 270, 40664075.
33. Vanhaesbroeck, B. et al (1997) *Trends Biochem. Sci.* (In press).
34. Leevers, S. J. et al (1996) *EMBO, J.* 6584–6594.
35. Chen, C. et al (1996) *Endocrinology* 137, 846–856.
36. Traverse, S. et al (1994) *Biochem. J.* 288, 351–355.
37. Marshall, C. J. (1995) "Specificity of receptor tyrosine kinase signalling-transient versus sustained extracellular signal-regulated kinase activation" 80, 179–185.
38. Lawrence, P. A and Johnston, P. (1986) *Cell* 45, 505–513.
39. Nothiger, R. et al (1989) *Development* 107, 505–518.
40. Steinmann-Zwicky, M. (1992) *Bioessays* 14, 513–518.
41. Cuenda, A. et al (1996) *EMBO, J.* 15, 4156–4164.
42. Lennon, G. G. et al (1996) *Genomics* 33, 151–152.
43. Sanchez, I. et al (1994) *Nature* 372, 794–798.
44. Andersson, S. et al (1989) *J. Biol. Chem.* 264, 8222–8229.
45. Alessi, D. R. et al (1996b) *FEBS Lett.* 399, 333–338.
46. Thompson, J. D. et al (1994) *Nuc. Acid Res.* 22, 4673–4680

EXAMPLE 6

Assay for Compounds Which Activate PDK1

An assay is set up with PDK1, GST-PKBα and the PKBα substrate, RPRAATF (SEQ ID NO: 9), (as described in Example 1) but with no 3-phosphoinositide. No activation of PKBα is observed. Compounds are tested in the assay and those that give rise to activation of PKBα via PDK1 are selected for further study. Phosphatidylinositol-3,4,5-trisphosphate is used as a positive control.

EXAMPLE 7

Assay for Compounds Which Inactivate PDK1

An assay is set up as above except that it includes phosphatidyl-3,4,5-trisphosphate and therefore PDK1 is active with respect to phosphorylating PKBα.

Compounds are tested in the assay and those that lead to inactivation of PKBα via PDK1 are selected for further study.

EXAMPLE 8

The assay is the same as Example 6 except that PKBα is replaced by PKBβ.

EXAMPLE 9

The assay is the same as Example 6 except that PKBα is replaced by PKBγ.

EXAMPLE 10

The assay is the same as Example 7 except that PKBα is replaced by PKBβ.

EXAMPLE 11

The assay is the same as Example 7 except that PKBα is replaced by PKBγ.

EXAMPLE 12

Assay for Compounds which Compete for Phosphatidylinositol-3,4,5-trisphosphatebinding of PDK1

PDK1 is incubated with radiolabelled phosphatidylinositol-3,4,5-trisphosphate in the presence of a test compound. Binding of the phospholipid to PDK1 in the presence of the test compound is compared to the binding in its absence.

Compounds which reduce or enhance the binding are selected for further study.

The assay may also be carried out with non-radiolabelled PtdIns(3,4,5)P3.

EXAMPLE 13

Assay for Compounds which Activate PDK1

An assay is set up with PDK1 and p70 S6 kinase. No 3-phosphoinositide need be present. Compounds are tested in the assay and those that activate PDK1 (and lead to increased phosphorylation of p70 S6 kinase) are selected.

EXAMPLE 14

Assay for Compounds which Activate PDK1

An assay is set up with PDK1 and a PKBα lacking a functional PH domain. No 3-phosphoinositide need be present. Compounds are tested and those that activate PDK1 (and lead to increased phosphorylation of PKBα lacking a functional PH domain) are selected.

References

1. Coffer, P. J. and Woodgett, J. R. (1991) "Molecular-cloning and characterization of a novel putative protein-serine kinase related to the camp-dependent and protein-kinase-C families" *Eur. J. Biochem.* 201, 475481.
2. Jones, P. F. et al (1991) "Molecular-cloning and identification of a serine threonine protein-kinase of the 2nd-messenger subfamily" *Proc. Natl. Acad. Sci USA* 88, 4171–4175.
3. Belacossa, A. et al (1991) "A retroviral oncogene, AKT, encoding a serine-threonine kinase containing an SH2-like region" *Science* 254, 244–247.
4. Franke, T. F. et al (1995) "The protein-kinase encoded by the AKT protooncogene is a target of the PDGF-activated phosphatidylinositol 3-kinase" *Cell* 81, 727–736.
5. Burgering, B. M. T. and Coffer, P. J. (1995) "Protein-kinase-B (C-AKT) in phosphatidylinositol-3-OH kinase signal-transduction" *Nature* 376, 599–602.
6. Kohn, A. D. et al (1995) "Insulin stimulates the kinase-activity of RAC-PK, a pleckstrin homology domain-containing SER/THR kinase" *EMBO J.* 14, 4288–4295.
7. Cheng, J. Q. et al (1992) "AKT2, a putative oncogene encoding a member of a subfamily of protein-serine threonine kinases, is amplified in human ovarian carcinomas" *Proc. Natl. Acad. Sci. USA* 89, 9267–9271.
8. Cheng, J. Q. et al (1996) "Amplification of AKT2 in human pancreatic-cancer cells and inhibition of AKT2 expression and tumorigenicity by antisense RNA" Proc. *Natl. Acad. Sci. USA* 93,3636–3641. 9. Cross, D. A. E. et al (1995) "Inhibition of glycogen-synthase kinase-3 by insulin-mediated by protein-kinase-B" *Nature*, 378, 785–789.
10. Welsh, G. I. et al (1994) "Wortmannin inhibits the effects of insulin and serum on the activities of glycogen-synthase kinase-3 and the mitogen-activated protein-kinase" *Biochem J.* 303, 15–20.
11. Kohn, A. D. et al (1996) "Expression of a constitutively active AKT SER/THR kinase in 3T3-L1 adipocytes stimulates glucose-uptake and glucose-transporter-4 translocation" *J. Biol. Chem.* 271, 31372–31378.
12. Dudek, H. et al (1997) "Regulation of neuronal survival by the Serine-Threonine protein kinase AKT" *Science* 275, 661–665.
13. Kauffmann-Zeh. et al (1997) "Suppression of C-Myc-Induced apoptosis by Ras signalling through PI(3)K and PKB" *Nature* 385, 544–548.
14. Andjelkovic, M. et al (1996) "Activation and phosphorylation of a pleckstrin homology domain-containing protein-kinase (RAC-PK/PKB) promoted by serum and protein phosphatase inhibitors" *Proc. Natl. Acad. Sci. USA*, 93, 5699–5704.
15. Alessi, D. R. et al (1996a) "Mechanism of activation of protein kinase B by insulin and IGF-1" *EMBO J.* 15, 6541–6551.
16. Alessi, D. R. et al (1996b) "Molecular basis for the substrate specificity of protein kinase B; comparison with MAPKAP kinase-1 and p70 S6 kinase" *FEBS Lett.* 399, 333–338.
17. Baker, R. R. and Thompson, W. (1973) "Selective acylation of 1-acyl-glycero-phosphorylinositol by rat brain microsomes. Comparison with 1-acy-lglycero-phosphorylcholine" *J. Biol. Chem.* 248, 7060–7065.
18. James, S. R. et al (1996) "Specific binding of the AKT-1 protein-kinase to phosphatidylinositol 3,4,5-trisphosphate without subsequent activation" *Biochem. J.* 315, 709–713.
19. Klippel, A. et al (1997) "A specific product of phosphatidyinositol 3-kinase directly activates the protein kinase AKT through its pleckstrin homology domain" *Mol. Cell. Biol.* 17, 338–344.

20. Franke, T. F. et al "Direct regulation of the AKT Proto-oncogene product by phosphatidylinositol-3,2-bisphosphate" *Science* 275,5 665–668.
21. Frech, M. et at (1996) "High affinity binding of inositol phosphates and phosphoinositides to the pleckstrin homology domain of RAC/Protein kinase B and their influence on the kinase activity" *J. Biol. Chem.* In the press.
22. Krebs., E. G. et at (1964) "Purification and properties of rabbit skeletal muscle phosphorylase B kinase" *Biochemistry* 3, 1023–1033.
23. Walsh, D. A. et at (1968) "An adenosine 3'5' monophosphate-dependent protein kinase from rabbit skeletal muscle" *J. Biol. Chem.* 246, 1968–1976.
24. Kohn, A. D. et at (1995) "Insulin stimulates the kinase activity of RAC-PK, a pleckstrin homology domain containing ser/thr kinase" *EMBO J.* 14, 4288–4295.
25. Kohn, A. D. et at (1996) "AKT, a pleckstrin homology domain-containing kinase, is activated primarily by phosphorylation" *J. Biol. Chem.* 271, 21920–21926.
26. James, S. R. et at (1994) "Interfacial hydrolysis of phosphatidylinositol 2-phosphate and phosphatidylinositol 4,5-bisphosphate by turkey erythrocyte phospholipase-C. *Biochem. J.* (1994) 499–506.
27. Sanchez, I. et at (1994) "Role of SAPK/ERK kinase-1 in the stress-activated pathway regulating transcription factor C-Jun" *Nature* 372, 794–798.
28. Alessi, D. R. et al (1995) "Assay and expression of Mitogen-Activated protein kinase, MAP kinase kinase and Raf" *Methods Enzymol.* 255, 279–290.
29. Bradford, M. M. (1976) "A rapid and sensitive method for the quantitation of microgram quantities of protein utilizing the principle of protein-dye binding" *Anal Biochem*, 72, 248–254.
30. Stokoe, D. et al (1992) "Mapkap kinase-2—A novel protein-kinase activated by the mitogen-activated protein-kinase" *EMBO J.* 11,3985–3994.
31. Vanhaesbroeck, B. et al (1997) "PI 3-kinase the story so far" *Trends Biochem. Sci.* in the press.

What is claimed is:

1. A substantially pure 3-phosphoinositide-dependent protein kinase having the amino acid sequence as shown in SEQ ID NO: 1.

2. A fusion protein comprising the protein kinase according to claim 1.

3. A method of isolating the protein kinase according to claim 1, the method comprising the steps of (a) obtaining material that contains said protein kinase, (b) obtaining cell free extracts from said material which contain said protein kinase, (c) fractionating said cell free extract and (d) selecting a fraction from step (c) which is capable of phosphorylating and activating protein kinase Bα in the presence of a 3-phosphoinositide.

4. An isolated human 3-phosphoinositide-dependent protein kinase that phosphorylates and activates protein kinase Bα obtainable by the method of claim 3.

5. A method of identifying a compound that modulates the activity of the protein kinase according to claim 1, the method comprising:
   contacting a compound with said protein kinase according to claim 1 or a fusion protein comprising said protein kinase and
   determining whether, in the presence of said compound, phosphorylation and activation of a protein kinase B or phosphorylation of a p70 S6 kinase is changed compared to the phosphorylation and activation of a protein kinase B or phosphorylation of a p70 S6 kinase in the absence of said compound.

6. A method according to claim 5 wherein the compound decreases the activity of the 3-phosphoinositide-dependent protein kinase.

7. A method according to claim 5 wherein the compound increases the activity of the 3-phosphoinositide-dependent protein kinase.

8. A method according to claim 5 wherein the compound competes with a 3-phosphoinositide.

9. A method according to claim 8 wherein the compound prevents activation of protein kinase Bα in the presence of phosphatidylinositol-3,4,5-trisphosphate or phosphatidylinositol-3,2-bisphosphate.

10. A method according to claim 5 wherein the compound modulates the activity of the 3-phosphoinositide-dependent protein kinase by binding to a protein kinase Bα and preventing phosphorylation and activation of protein kinase Bα by the 3-phosphoinositide-dependent protein kinase.

11. A method of identifying a compound that mimics the effect of a 3-phosphoinositide on the protein kinase according to claim 1, the method comprising determining whether said compound activates the protein kinase according to claim 1 or a fusion protein comprising said protein kinase so that it can phosphorylate and activate a protein kinase B or phosphorylate a p70 S6 kinase, the activation by said compound being in the absence of a phosphatidylinositol-3,4,5-trisphosphate or a phosphatidyl-inositol-3,2-bisphosphate or another 3-phosphoinositide.

12. A method of screening for compounds which modulate the activity of the protein kinase according to claim 1 or a fusion protein comprising said protein kinase, or compounds which modulate their interactions with a 3-phosphoinositide or with protein kinase B, wherein said screening comprises:
   contacting a compound with the protein kinase according to claim 1 or a fusion protein comprising said protein kinase and selecting compounds which modulate the activity of said protein kinase according to claim 1 or a fusion protein comprising said protein kinase.

13. A method of activating protein kinase B, the method comprising contacting said protein kinase B with the 3-phosphoinositide-dependent protein kinase according to claim 1.

14. A kit comprising a substantially pure 3-phosphoinositide-dependent protein kinase having the amino acid sequence as shown in SEQ ID NO: 1 or a fusion protein comprising said protein kinase and a means for carrying out the method according to claim 5.

* * * * *